United States Patent
Ghazal et al.

(10) Patent No.: US 10,851,415 B2
(45) Date of Patent: Dec. 1, 2020

(54) MOLECULAR PREDICTORS OF SEPSIS

(71) Applicant: The University Court of the University of Edinburg, Edinburgh Lothian (GB)

(72) Inventors: Peter Ghazal, Edinburgh Midlothian (GB); Paul Dickinson, Edinburgh Midlothian (GB); Thorsten Forster, Edinburgh Midlothian (GB); Claire Smith, Edinburgh Midlothian (GB); Ben Stenson, Edinburgh Midlothian (GB); Mizan Khondoker, Edinburgh Midlothian (GB)

(73) Assignee: University College Cardiff Consultants Limited, Cardiff (GB)

(*) Notice: Subject to any disclaimer, the term of this patent is extended or adjusted under 35 U.S.C. 154(b) by 0 days.

(21) Appl. No.: 15/302,367

(22) PCT Filed: Apr. 7, 2015

(86) PCT No.: PCT/GB2015/051060
§ 371 (c)(1),
(2) Date: Oct. 6, 2016

(87) PCT Pub. No.: WO2015/155517
PCT Pub. Date: Oct. 15, 2015

(65) Prior Publication Data
US 2017/0022568 A1  Jan. 26, 2017

(30) Foreign Application Priority Data
Apr. 7, 2014  (GB) .................. 1406259.0

(51) Int. Cl.
*C12Q 1/6883* (2018.01)

(52) U.S. Cl.
CPC ..... *C12Q 1/6883* (2013.01); *C12Q 2600/158* (2013.01)

(58) Field of Classification Search
CPC .................. C12Q 1/6883; C12Q 2600/158
See application file for complete search history.

(56) References Cited

U.S. PATENT DOCUMENTS

| | | | |
|---|---|---|---|
| 2004/0106142 A1 | 6/2004 | Ivey et al. | |
| 2006/0019256 A1* | 1/2006 | Clarke | C12N 5/0695 435/6.14 |
| 2009/0203534 A1 | 8/2009 | Hossain et al. | |
| 2009/0264305 A1 | 10/2009 | Brandon | |
| 2011/0105350 A1* | 5/2011 | Garrett | C12Q 1/6883 506/9 |

OTHER PUBLICATIONS

GSE11755. Public on Jun. 14, 2008. Retrieved on Apr. 20, 2018 from the internet: https://www.ncbi.nlm.nih.gov/geo/query/acc.cgi?acc=GSE11755. (Year: 2008).*
Saito-Hisaminato et al. DNA Research. 2002. 9:35-45. (Year: 2002).*
Hoshikawa et al. Physical Genomics. 2003. 12: 209-219. (Year: 2003).*
The GXSIDRA webpage. Retrieved on Apr. 20, 2018 from the internet: http://monocyte.gxbsidra.org/dm3/geneBrowser/show/4000035. (Year: 2008).*
Nee et al. Emerg Med J. 2006. 23(9):713-717. (Year: 2006).*
Appendix A (Prepared by Examiner Dauner; collected on Nov. 26, 2018 from the internet: https://gemma.msl.ubc.ca/expressionExperiment/showExpressionExperiment.html?id=4785). (Year: 2012).*
Chan (G&P magazine. 2006. 6(3): 20-26) (Year: 2006).*
Chen et al. Molecular & Cellular Proteomics. 2002. 1:304-313. (Year: 2002).*
Kendrick. "A gene's mRNA level does not usually predict its protein level". Sep. 25, 2014. Kendrick Labs, Inc. (Year: 2014).*
Pascal et al. BMC Genomics. 2008. 9:246. (Year: 2008).*
Epo Examination Report, dated Feb. 28, 2018 for Application No. 15717596.9-1118.
S. Van Cromphaut et al, Glucose Metabolism and Insulin Resistance in Sepsis, Current Pharmaceutical Design, Jul. 1, 2008, vol. 14, No. 19, pp. 1887-1899.
International Search Report, dated May 20, 2015, PCT/GB2015/051060.
International Searching Authority, dated Jan. 2015, PCT/GB2015/051060.

* cited by examiner

*Primary Examiner* — Joseph G. Dauner
(74) *Attorney, Agent, or Firm* — Dickinson Wright PLLC

(57) ABSTRACT

Sepsis remains a leading cause of morbidity and mortality in neonates worldwide. There is also clinically a low threshold for suspicion of infection in neonates, in particular as presentation varies greatly from very subtle to catastrophic collapse. The lack of reliably sensitive tests and the potential life-threatening consequences of delayed treatment of infection results in the widespread use of empirical antibiotics exposing many infants without infection to broad-spectrum antibiotics. The present invention provides a series of patient-invariant biomarkers for screening neonates and other subjects for infection that predicts bacterial infection with high accuracy; and is further shown to have predictive value in identifying infection in suspected cases with blood-culture negative tests.

15 Claims, 36 Drawing Sheets

Specification includes a Sequence Listing.

Figure 1

Figure 1A. Demographics of samples used

| Sample Set | Classifier Training Set | | Technical Validation Set | | Classifier Test Set | |
| --- | --- | --- | --- | --- | --- | --- |
| Infection Status | Infected (n=28) | Control (n=35) | Infected (n=18) | Control (n=24) | Infected (n=16) | Control (n=10) |
| Male | 15 (54%) | 22 (63%) | 10 (56%) | 15 (63%) | 10 (63%) | 9 (90%) |
| Gestation completed at birth (wk): range (mean) | 24-38 (28.5) | 26-42 (37.9) | 24-38 (28.8) | 26-42 (37.3) | 23-40 (28.3) | 24-41 (31) |
| Gestation completed at sampling (wk): range (mean) | 26-39 (31.1) | 31-44 (39.4) | 26-39 (30.8) | 31-44 (39.1) | 25-41 (33.8) | 29-42 (34.9) |
| Birthweight (g): range (mean) | 430-3380 (1126) | 650-4570 (3080) | 430-3380 (1236) | 650-4350 (2941) | 635-3160 (1134) | 800-4220 (1932) |

Figure 1B. Microorganisms isolated from infected groups

| Organism | Classifier Training Set | Technical Validation Set | Classifier Test Set |
| --- | --- | --- | --- |
| Coagulase negative staphylococcus | 15 | 8 | 7 |
| Enterococcus species | 4 | 3 | 1 |
| Group B Streptococcus | 2 | 2 | 1 |
| Klebsiella species | 2 | 1 | 2 |
| Candida albicans and Klebsiella species | 1 | 1 | - |
| Escherichia Coli | 1 | 1 | 1 |
| Enterobacter cloacae | 1 | 1 | - |
| Pseudomonas aeruginosa | 1 | 1 | 1 |
| CMV | 1 | - | - |
| Listeria monocytogenes | - | - | 1 |
| Serratia marcescens | - | - | 2 |

Table S1 C. Reasons for blood sampling in control group

| Reason | Classifier Training Set | Technical Validation Set | Classifier Test Set |
| --- | --- | --- | --- |
| Screening test: maternal thyroid disease | 17 | 9 | - |
| Bilirubin check due to jaundice | 5 | 4 | 1 |
| "Routine" neonatal screening (preterms) | 5 | 4 | 6 |
| Electrolyte check: previous deranged Na | 3 | 3 | - |
| Screening test: pigmented scrotum | 2 | 1 | 3 |
| Blood count check: Coomb's positive | 1 | 1 | - |
| Screening test: newborn bloodspot | 1 | 1 | - |
| Neonatal encephalopathy | 1 | 1 | - |

Figure 11 continued
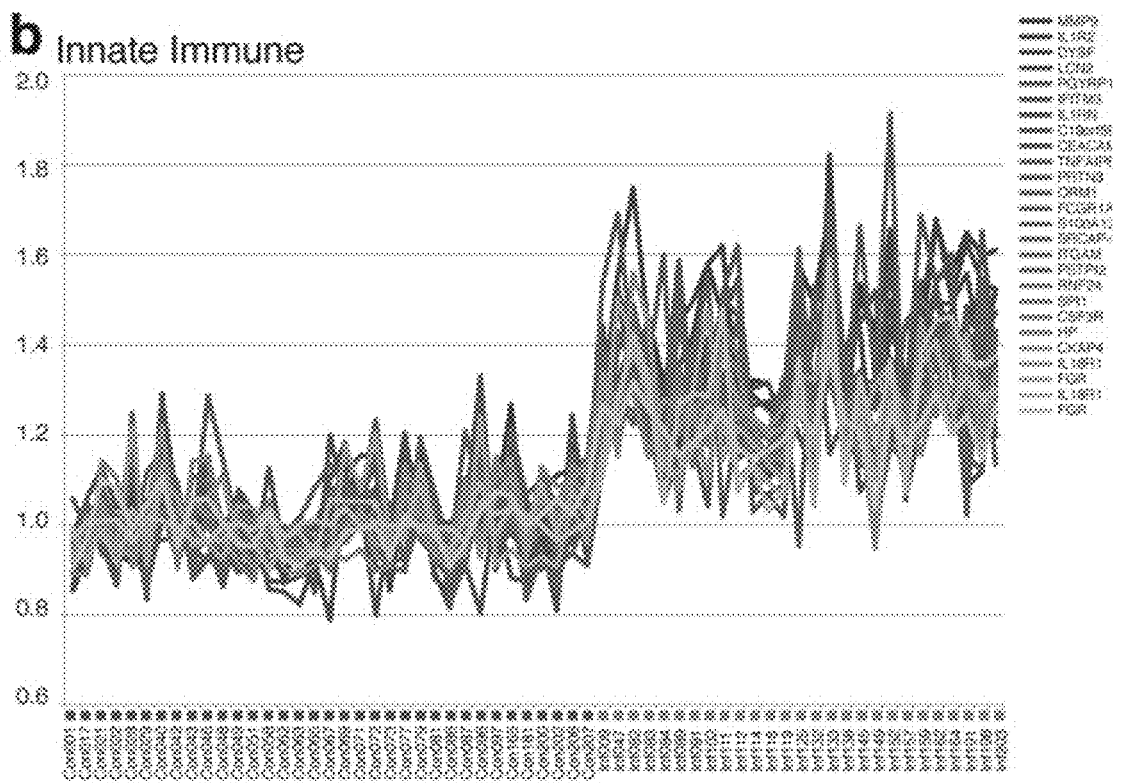
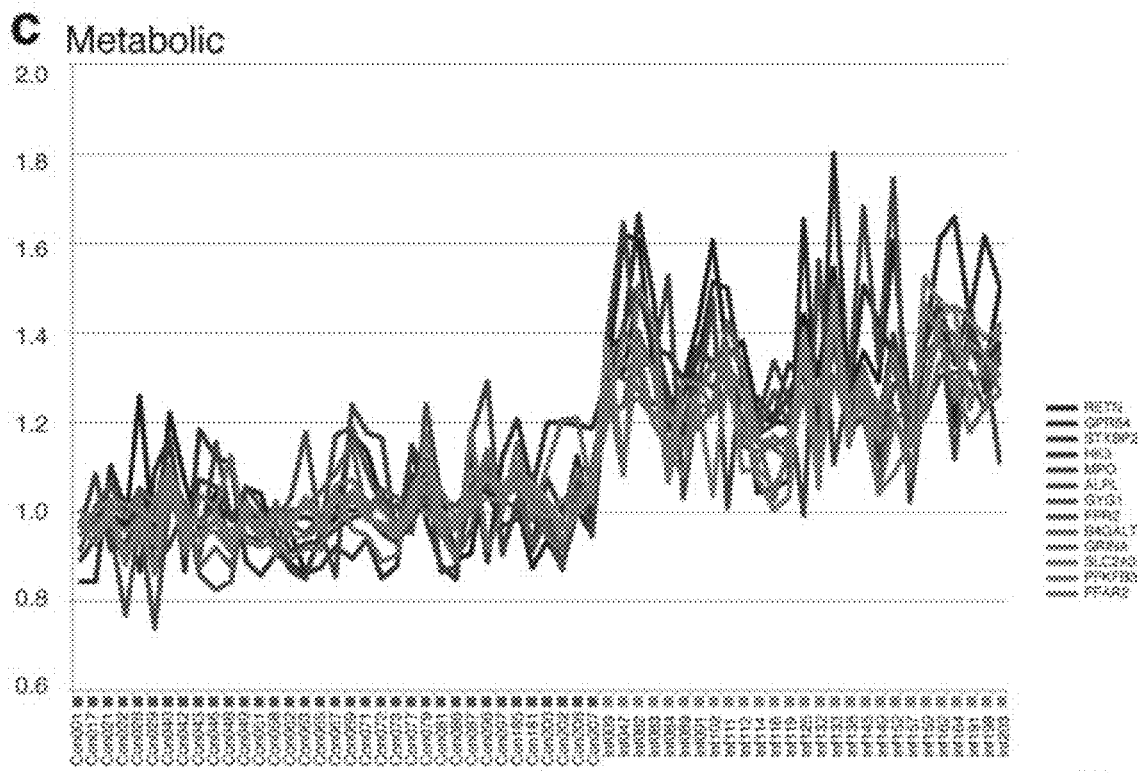

D i

D ii

D iii

| Demographics | Bacterial pneumonia | Healthy controls |
|---|---|---|
| Number in group | 16 | 18 |
| Age (years) | 62 ± 13 | 43 ± 16 |
| Male/Female | 7/9 | 6/12 |
| Comorbidities (%) | | |
| Hypertension | 31.3 | 16.6 |
| Heart disease | 37.5 | 0 |
| Diabetes | 12.5 | 0 |
| COPD | 37.5 | 0 |
| Cancer | 12.5 | 0 |
| Trauma | 0 | 0 |
| Recent surgery (last 7 days) | 6.25 | 0 |
| Severity of disease | | |
| Mortality (%) | 31.3 | NA |
| APACHE II | 18 ± 6.6 | NA |
| Treatment (%) | | |
| Mechanical ventilation | 93.8 | NA |
| Renal dialysis | 6.3 | NA |
| Vasopressor therapy | 56.3 | NA |

MOLECULAR PREDICTORS OF SEPSIS

CROSS-REFERENCE TO RELATED APPLICATIONS

The present application is a 35 U.S.C. Section 371 national stage filing of International Patent Application No. PCT/GB2015/051060, filed 7 Apr. 2015, and through which priority is claimed to United Kingdom Patent Application 1406259.0, filed 7 Apr. 2014, the disclosures of which are incorporated herein by reference in their entireties.

SEQUENCE LISTING

This disclosure incorporates by reference in its entirety the material in the accompanying ASCII text file designated P215858WO, created 15 Apr. 2015, and having a file size of 10,485 bytes.

FIELD OF THE INVENTION

The present invention relates to the identification of a network of 52 genes which are differentially expressed in blood samples taken from infected neonates. The inventors have developed a novel diagnostic assay which is capable of identifying sepsis.

BACKGROUND TO THE INVENTION

Despite advances in neonatal care, infection remains a leading cause of morbidity and mortality in neonates worldwide. Although some progress towards survival of children under the age of 5 has been made as one of the Millennium Development Goals, neonatal morbidity and mortality remains a major issue in resource rich and poor settings (Liu et al., *Lancet* doi:10.1016/S0140-6736(12)60560-1 (2012)). Of 7.6 million deaths in children younger than 5 years in 2010, 64.0% (4.879 million) were attributable to infectious causes and 40.3% (3.072 million) occurred in neonates (Liu et al., 2012 ibid.). Up to 65% of extremely low birth weight infants develop presumed sepsis in the neonatal period (Stoll, B. J. et al., *JAMA* 292, 2357-2365 (2004)). Accordingly there is a low threshold for clinical suspicion of infection in neonates, particularly as presentation varies greatly from very subtle signs to catastrophic collapse. Currently, empirical antibiotics are widely used because of the lack of reliably sensitive tests and the potential life-threatening consequences of delayed treatment of infection. Consequently, many infants without infection are exposed to broad-spectrum antibiotics. To date our understanding of how a newborn responds to infection remains largely under-investigated.

Clinical investigation of neonates is problematic and our understanding of neonatal sepsis is also hampered by a lack of appropriate animal models and species-specific differences in response to infection. The immaturity of neonatal immune systems renders them more susceptible to infection than older individuals, yet neonatal immunity is not well characterized (Sharma et al., *Clin Immunol*145, 61-68 (2012)). Moreover, host immune responses are known to play a significant role in the pathophysiology of sepsis; yet it is not known how humans respond at the systemic pathway level to infection in early life.

Several studies have shown that changes in host gene expression may occur pre-symptomatically in response to infection in any part of the body, with the continuous interaction between blood and tissue allowing blood cells to act as biosensors for the changes (Manger & Relman, *Curr Opin Immunol* 12, 215-218 (2000); Liew et al., *J Lab Clin Med* 147, 126-132 (2006)).

A number of groups have investigated host-pathogen interactions using genomic approaches (Berry et al., *Nature* 466, 973-977 (2010); Hyatt et al., *Nat Immunol* 7, 686-691 (2006); Manger & Relman, *Curr Opin Immunol* 12, 215-218 (2000)). Similarly, transcriptional profiles of blood from adults and children with infection have been examined, but data from infected neonates are lacking (Berry et al., *Nature* 466, 973-977 (2010); Ardura et al., *PLoS One* 4, e5446 (2009); Fjaerli et al., *BMC Infect Dis* 6, 175 (2006); Madsen-Bouterse et al., *Am J Reprod Immunol* 63, 73-92 (2010); Ramilo et al., *Blood* 109, 2066-2077 (2007); Tang et al. *Am J Respir Crit Care Med* 176, 676-684 (2007). However, a limited number of host markers at the protein level have also been investigated in neonates (Layseca-Espinosa et al., *Pediatric allergy and immunology: official publication of the European Society of Pediatric Allergy and Immunology* 13, 319-327 (2002); Ng et al., *Arch Dis Child Fetal Neonatal Ed* 77, F221-227 (1997); Ng & Lam, *Curr Opin Pediatr* 18, 125-131 (2006); Labib et al., *International Journal of Microbiological Research* 4, 77-85 (2013); Hodge et al., *Clin Exp Immunol* 135, 125-129 (2004).

Despite the prevalence of the condition and the intensity of research in this area, substantial progress in understanding the molecular basis of neonatal sepsis has not been forthcoming and it continues to be a major clinical problem worldwide. Furthermore, although many tests are informative regarding the risk of infection, no current biomarker or group of biomarkers is sufficient to confidently exclude infection at the time of suspicion (Ng & Lam, *Curr Opin Pediatr* 18, 125-131 (2006). A pressing need therefore exists for novel, sensitive and specific diagnostic tools which specifically detect biomarkers associated with the early stages of neonatal infection. The discovery of specific biomarkers for neonatal sepsis would enable the administration of empirical antibiotics to be avoided in all but the most critically ill newborns. This is particularly important given concerns that empirical antibiotics may increase the risks of developing necrotising enterocolitis and mortality in premature infants (Cotton, *Arch Dis Child Educ Pract Ed* 95, 94, (2010)).

The inventors have surprisingly uncovered the pathway biology underlying neonatal sepsis at the first clinical signs of infection and thereby identified and validated a panel of biologically connected network modules. The inventors have unexpectedly discovered that analysis of the expression levels of particular combinations of biomarkers, and specifically those of a pathway previously unconnected to immune responses, gives an unusually high diagnostic quality. Despite patient heterogeneity, the 52-node dual biomarker network had greater than 98% accuracy for detecting bacterial infection with 100% sensitivity showing superior performance to previously characterised markers. Furthermore, these specific combinations of biomarkers allowed the detection of neonatal sepsis in samples which had displayed blood-culture negative results, illustrating the specific diagnostic benefits of the particular combinations of biomarkers of the invention. The unexpectedly high accuracy and sensitivity values could not have resulted from the investigation of any of the individual biomarkers alone, nor could they have been predicted from the prior art.

SUMMARY OF THE INVENTION

Accordingly, the present invention provides a method for diagnosing sepsis. The invention also provides a device for use in the diagnosis of sepsis and a kit of parts for use in the diagnosis of sepsis.

Accordingly, in a first aspect the present invention provides a method of diagnosing sepsis, comprising the steps of:
a) analysing a biological sample obtained from a subject to determine the levels of two or more biomarkers listed in Table 1, wherein the biomarkers are selected from any of groups A, B or C; and
b) comparing the levels of the biomarkers determined in (a) with one or more reference values, wherein a difference in the expression levels of the two or more biomarkers in the sample(s) from the subject compared to the one or more reference values is indicative of sepsis.

Throughout the term "diagnosing" or "diagnosis" in relation to sepsis is used to mean both the indication of the presence of ongoing sepsis and the indication of the initial stages of sepsis where other physical or biological measurements may be taken in conjunction with the measurement of biomarker expression levels. In particular, the invention is intended to cover the detection of the presence of active sepsis in a biological sample.

In embodiments of the invention it will be appreciated that given the surprising power of the combination of biomarkers of the present invention to differentiate between sepsis and non-sepsis, any two biomarkers from groups A, B or C may be selected for analysis. In accordance with the present invention, it would be routine for a person skilled in the art to select any combination of biomarkers from the list disclosed in Table 1. The following combinations represent preferred combinations of biomarkers:

SLC2A3 and LRRN3; SLC2A3, GPR84 and LRRN3; SLC2A3, GPR84, RETN, and LRRN3; SLC2A3, LRRN3 and TRAJ17; SLC2A3, GPR84, LRRN3 and TRAJ17; SLC2A3, GPR84, RETN, LRRN3 and TRAJ17; SLC2A3, LRRN3, TRAJ17 and CD3D; SLC2A3, GPR84, LRRN3, TRAJ17 and CD3D; SLC2A3, GPR84, RETN, LRRN3, TRAJ17 and CD3D; LRRN3 and BASP1; LRRN3, TRAJ17 and BASP1; LRRN3, TRAJ17, CD3D and BASP1; LRRN3, BASP1 and CKAP4; LRRN3, TRAJ17, BASP1 and CKAP4; LRRN3, TRAJ17, CD3D, BASP1 and CKAP4; LRRN3, BASP1, CKAP4 and C19orf59; LRRN3, TRAJ17, BASP1, CKAP4 and C19orf59; LRRN3, TRAJ17, CD3D, BASP1, CKAP4 and C19orf59; SLC2A3 and BASP1; SLC2A3, GPR84 and BASP1; SLC2A3, GPR84, RETN and BASP1; SLC2A3, BASP1 and CKAP4; SLC2A3, GPR84, BASP1 and CKAP4; SLC2A3, GPR84, RETN, BASP1 and CKAP4; SLC2A3, BASP1, CKAP4 and C19orf59; SLC2A3, GPR84, BASP1, CKAP4 and C19orf59; SLC2A3, GPR84, RETN, BASP1, CKAP4 and C19orf59.

In a particularly preferred embodiment the invention provides a method of diagnosing sepsis, comprising the steps of:
a) analysing a biological sample obtained from a subject to determine the levels of two or more biomarkers listed in Table 1, wherein the biomarkers are;
SLC2A3, GPR84, RETN, LRRN3, TRAJ17, CD3D, BASP1, CKAP4 and C19orf59; and
b) comparing the levels of the biomarkers determined in (a) with one or more reference values, wherein a difference in the expression levels of the two or more biomarkers in the sample(s) from the subject compared to the one or more reference values is indicative of sepsis.

The present invention also provides a method of diagnosing sepsis, comprising the steps of:
a) analysing a biological sample obtained from a subject to determine the levels of two or more biomarkers listed in Table 1, wherein at least one biomarker is selected from group A and at least one other biomarker is selected from any of groups A, B or C; and
b) comparing the levels of the biomarkers determined in (a) with one or more reference values, wherein a difference in the expression levels of the two or more biomarkers in the sample(s) from the subject compared to the one or more reference values is indicative of sepsis.

In one embodiment the at least one biomarker selected from group A may be GYG1, B4GALT5, SLC2A3, HK3, GPR84, PFKFB3, RETN, STXBP2, FPR2, ALPL, GRINA, FFAR2 and MPO. Preferably the at least one biomarker selected from group A will comprise SLC2A3. More preferably the at least one biomarker selected from group A will comprise SLC2A3 and GPR84. Even more preferably the at least one biomarker will comprise SLC2A3, GPR84 and RETN.

In another embodiment the at least one biomarker selected from group B or C may be selected from the group IL1RN, BASP1, PSTPIP2, CKAP4, DYSF, C19orf59, IL18R1, MMP9, FGR, SPI1, PGLYRP1, RNF24, ANKRD22, CEBPD, IL1R2, LOC729021 (SRCAP-like helicase), S100A12, ITGAM, FCGR1A, IFITM3, CSF3R, LCN2, TNFAIP6, HP, ORM1, CEACAM1, PRTN3, LRRN3, GRAP, TRAJ17, CD3D, CD247, ITM2A, LIME1, HLA-DMB, CD7, MAL, TRBV28 and RPS29. In a preferred embodiment the at least one biomarker selected from group B or C will comprise LRRN3. More preferably, the at least one biomarker selected from group B or C will comprise LRRN3 and TRAJ17. Even more preferably the at least one biomarker selected from group B or C will comprise LRRN3, TRAJ17 and CD3D. In a preferred embodiment the at least one biomarker selected from group B or C will comprise BASP1. More preferably the at least one biomarker will comprise BASP1 and CKAP4. Even more preferably the at least one biomarker will comprise BASP1 CKAP4, and C19orf59.

The present invention also provides a method of diagnosing sepsis, comprising the steps of:
a) analysing a biological sample obtained from a subject to determine the levels of three or more biomarkers listed in Table 1, wherein at least one biomarker is selected from each of groups A, B and C; and
b) comparing the levels of the biomarkers determined in (a) with one or more reference values, wherein a difference in the expression levels of the two or more biomarkers in the sample(s) from the subject compared to the one or more reference values is indicative of sepsis.

Commonly, the at least one biomarker selected from group A may be any member of group A. However, suitably the at least one biomarker selected from group A will be selected from the group SLC2A3, GPR84 and RETN. Similarly, the at least one biomarker selected from group B may be any member of group B. However, suitably the at least one biomarker selected from group B will be selected from the group BASP1, CKAP4, and C19orf59. Finally, the at least one biomarker selected from group C may be any member of group C. However, suitably the at least one biomarker selected from group C will be selected from the group LRRN3, TRAJ17 and CD3D. In a preferred embodiment the biomarkers selected will comprise SLC2A3, BASP1 and LRRN3 and more preferably, the biomarkers selected will further comprise GPR84, CKAP4 and TRAJ17.

In the present invention group A consists of the following biomarkers associated with the glycolytic, glucose transport and sterol metabolism pathways;
GYG1, B4GALT5, SLC2A3, HK3, GPR84, PFKFB3, RETN, STXBP2, FPR2, ALPL, GRINA, FFAR2 and MPO. It will be appreciated that any one of these biomarkers may be used in combination with any biomarker or combination of biomarkers selected from group A, group B or group C.

In the present invention group B consists of the following biomarkers associated with the innate immune response pathway;

IL1RN, BASP1, PSTPIP2, CKAP4, DYSF, C19orf59, IL18R1, MMP9, FGR, SPI1, PGLYRP1, RNF24, ANKRD22, CEBPD, IL1R2, LOC729021 (SRCAP-like helicase), S100A12, ITGAM, FCGR1A, IFITM3, CSF3R, LCN2, TNFAIP6, HP, ORM1, CEACAM1 and PRTN3. It will be appreciated that any one of these biomarkers may be used in combination with any biomarker or combination of biomarkers selected from group A, group B or group C.

In the present invention group C consists of the following biomarkers associated with the adaptive immune response pathway;

LRRN3, GRAP, TRAJ17, CD3D, CD247, ITM2A, LIME1, HLA-DMB, CD7, MAL, TRBV28 and RPS29. It will be appreciated that any one of these biomarkers may be used in combination with any biomarker or combination of biomarkers selected from group A, group B or group C.

Typically more than one biomarker may be selected from each group of biomarkers and their levels in a biological sample investigated in combination. In accordance with the present invention, a person skilled in the art would appreciate that any combination of biomarkers may be selected from the list disclosed in Table 1. In one embodiment at least one biomarker is selected for analysis from group A and at least one other biomarker is selected from groups A, B or C. Preferably at least one biomarker is selected from group A and at least one other biomarker is selected from group C. Normally more than one biomarker will be selected from group A.

Embodiments of the present invention include a method of diagnosing sepsis comprising assaying a biological sample to determine the levels of combinations of biomarkers and comparing the levels of said biomarkers with reference values and/or the levels of the corresponding biomarkers from one or more control samples, wherein the combination of biomarkers comprises the following:

GYG1 and B4GALT5, or GYG1 and SLC2A3, or GYG1 and HK3, or GYG1 and GPR84, or GYG1 and PFKFB3, or GYG1 and RETN, or GYG1 and STXBP2, or GYG1 and FPR2, or GYG1 and ALPL, or GYG1 and GRINA, or GYG1 and FFAR2, or GYG1 and MPO, or B4GALT5 and GYG1, or B4GALT5 and SLC2A3, or B4GALT5 and HK3, or B4GALT5 and GPR84, or B4GALT5 and PFKFB3, or B4GALT5 and RETN, or B4GALT5 and STXBP2, or B4GALT5 and FPR2, or B4GALT5 and ALPL, or B4GALT5 and GRINA, or B4GALT5 and FFAR2, or B4GALT5 and MPO, or SLC2A3 and GYG1, or SLC2A3 and B4GALT5, or SLC2A3 and HK3, or SLC2A3 and GPR84, or SLC2A3 and PFKFB3, or SLC2A3 and RETN, or SLC2A3 and STXBP2, or SLC2A3 and FPR2, or SLC2A3 and ALPL, or SLC2A3 and GRINA, or SLC2A3 and FFAR2, or SLC2A3 and MPO, or HK3 and GYG1, or HK3 and B4GALT5, or HK3 and SLC2A3, or HK3 and GPR84, or HK3 and PFKFB3, or HK3 and RETN, or HK3 and STXBP2, or HK3 and FPR2, or HK3 and ALPL, or HK3 and GRINA, or HK3 and FFAR2, or HK3 and MPO, or GPR84 and GYG1, or GPR84 and B4GALT5, or GPR84 and SLC2A3, or GPR84 and HK3, or GPR84 and PFKFB3, or GPR84 and RETN, or GPR84 and STXBP2, or GPR84 and FPR2, or GPR84 and ALPL, or GPR84 and GRINA, or GPR84 and FFAR2, or GPR84 and MPO, or PFKFB3 and GYG1, or PFKFB3 and B4GALT5, or PFKFB3 and SLC2A3, or PFKFB3 and HK3, or PFKFB3 and GPR84, or PFKFB3 and RETN, or PFKFB3 and STXBP2, or PFKFB3 and FPR2, or PFKFB3 and ALPL, or PFKFB3 and GRINA, or PFKFB3 and FFAR2, or PFKFB3 and MPO, or RETN and GYG1, or RETN and B4GALT5, or RETN and SLC2A3, or RETN and HK3, or RETN and GPR84, or RETN and PFKFB3, or RETN and STXBP2, or RETN and FPR2, or RETN and ALPL, or RETN and GRINA, or RETN and FFAR2, or RETN and MPO, or STXBP2 and GYG1, or STXBP2 and B4GALT5, or STXBP2 and SLC2A3, or STXBP2 and HK3, or STXBP2 and GPR84, or STXBP2 and PFKFB3, or STXBP2 and RETN, or STXBP2 and FPR2, or STXBP2 and ALPL, or STXBP2 and GRINA, or STXBP2 and FFAR2, or STXBP2 and MPO, or FPR2 and GYG1, or FPR2 and B4GALT5, or FPR2 and SLC2A3, or FPR2 and HK3, or FPR2 and GPR84, or FPR2 and PFKFB3, or FPR2 and RETN, or FPR2 and STXBP2, or FPR2 and ALPL, or FPR2 and GRINA, or FPR2 and FFAR2, or FPR2 and MPO, or ALPL and GYG1, or ALPL and B4GALT5, or ALPL and SLC2A3, or ALPL and HK3, or ALPL and GPR84, or ALPL and PFKFB3, or ALPL and RETN, or ALPL and STXBP2, or ALPL and FPR2, or ALPL and GRINA, or ALPL and FFAR2, or ALPL and MPO, or GRINA and GYG1, or GRINA and B4GALT5, or GRINA and SLC2A3, or GRINA and HK3, or GRINA and GPR84, or GRINA and PFKFB3, or GRINA and RETN, or GRINA and STXBP2, or GRINA and FPR2, or GRINA and ALPL, or GRINA and FFAR2, or GRINA and MPO, or FFAR2 and GYG1, or FFAR2 and B4GALT5, or FFAR2 and SLC2A3, or FFAR2 and HK3, or FFAR2 and GPR84, or FFAR2 and PFKFB3, or FFAR2 and RETN, or FFAR2 and STXBP2, or FFAR2 and FPR2, or FFAR2 and ALPL, or FFAR2 and GRINA, or FFAR2 and MPO, or MPO and GYG1, or MPO and B4GALT5, or MPO and SLC2A3, or MPO and HK3, or MPO and GPR84, or MPO and PFKFB3, or MPO and RETN, or MPO and STXBP2, or MPO and FPR2, or MPO and ALPL, or MPO and GRINA, or MPO and FFAR2, or GYG1 and IL1RN, or GYG1 and BASP1, or GYG1 and PSTPIP2, or GYG1 and CKAP4, or GYG1 and DYSF, or GYG1 and C19orf59, or GYG1 and IL18R1, or GYG1 and MMP9, or GYG1 and FGR, or GYG1 and SPI1, or GYG1 and PGLYRP1, or GYG1 and RNF24, or GYG1 and ANKRD22, or GYG1 and CEBPD, or GYG1 and IL1R2, or GYG1 and LOC729021 (SRCAP-like helicase), or GYG1 and S100A12, or GYG1 and ITGAM, or GYG1 and FCGR1A, or GYG1 and IFITM3, or GYG1 and CSF3R, or GYG1 and LCN2, or GYG1 and TNFAIP6, or GYG1 and HP, or GYG1 and ORM1, or GYG1 and CEACAM1, or GYG1 and PRTN3, or GYG1 and LRRN3, or GYG1 and GRAP, or GYG1 and TRAJ17, or GYG1 and CD3D, or GYG1 and CD247, or GYG1 and ITM2A, or GYG1 and LIME1, or GYG1 and HLA-DMB, or GYG1 and CD7, or GYG1 and MAL, or GYG1 and TRBV28, or GYG1 and RPS29, or B4GALT5 and IL1RN, or B4GALT5 and BASP1, or B4GALT5 and PSTPIP2, or B4GALT5 and CKAP4, or B4GALT5 and DYSF, or B4GALT5 and C19orf59, or B4GALT5 and IL18R1, or B4GALT5 and MMP9, or B4GALT5 and FGR, or B4GALT5 and SPI1, or B4GALT5 and PGLYRP1, or B4GALT5 and RNF24, or B4GALT5 and ANKRD22, or B4GALT5 and CEBPD, or B4GALT5 and IL1R2, or B4GALT5 and LOC729021 (SRCAP-like helicase), or B4GALT5 and S100A12, or B4GALT5 and ITGAM, or B4GALT5 and FCGR1A, or B4GALT5 and IFITM3, or B4GALT5 and CSF3R, or B4GALT5 and LCN2, or B4GALT5 and TNFAIP6, or B4GALT5 and HP, or B4GALT5 and ORM1, or B4GALT5 and CEACAM1, or B4GALT5 and PRTN3, or B4GALT5 and LRRN3, or B4GALT5 and GRAP, or B4GALT5 and TRAJ17, or B4GALT5 and CD3D, or B4GALT5 and CD247, or B4GALT5 and ITM2A, or B4GALT5 and LIME1, or B4GALT5 and HLA-DMB, or B4GALT5 and CD7, or B4GALT5 and MAL, or B4GALT5 and TRBV28, or B4GALT5 and RPS29, or SLC2A3 and IL1RN, or SLC2A3 and BASP1, or SLC2A3 and PSTPIP2, or SLC2A3 and CKAP4, or SLC2A3 and DYSF, or SLC2A3 and C19orf59, or SLC2A3 and IL18R1, or SLC2A3 and MMP9, or SLC2A3 and FGR, or SLC2A3 and SPI1, or SLC2A3 and PGLYRP1, or SLC2A3 and RNF24, or SLC2A3 and ANKRD22, or SLC2A3 and CEBPD, or SLC2A3 and IL1R2, or SLC2A3 and LOC729021 (SRCAP-like helicase), or SLC2A3 and S100A12, or SLC2A3 and ITGAM, or SLC2A3 and FCGR1A, or SLC2A3 and IFITM3, or SLC2A3 and CSF3R, or SLC2A3 and LCN2, or SLC2A3 and TNFAIP6, or SLC2A3 and HP, or SLC2A3 and ORM1, or SLC2A3 and CEACAM1, or SLC2A3 and PRTN3, or SLC2A3 and LRRN3, or SLC2A3 and GRAP, or SLC2A3 and TRAJ17, or SLC2A3 and CD3D, or SLC2A3 and CD247, or SLC2A3 and ITM2A, or SLC2A3 and LIME1, or SLC2A3 and HLA-DMB, or SLC2A3 and CD7, or SLC2A3 and MAL, or SLC2A3 and TRBV28, or SLC2A3 and RPS29, or HK3 and IL1RN, or HK3 and BASP1, or HK3 and PSTPIP2, or HK3 and CKAP4, or HK3 and DYSF, or HK3 and C19orf59, or HK3 and IL18R1, or HK3 and MMP9, or HK3 and FGR, or HK3 and SP11, or HK3 and PGLYRP1, or HK3 and RNF24, or HK3 and ANKRD22, or HK3 and CEBPD, or HK3 and IL1R2, or HK3 and LOC729021 (SRCAP-like helicase), or HK3 and S100A12, or HK3 and ITGAM, or HK3 and FCGR1A, or HK3 and IFITM3, or HK3 and CSF3R, or HK3 and LCN2, or HK3 and TNFAIP6, or HK3 and HP, or HK3 and ORM1, or HK3 and CEACAM1, or HK3 and PRTN3, or HK3 and LRRN3, or HK3 and GRAP, or HK3 and TRAJ17, or HK3 and CD3D, or HK3 and CD247, or HK3 and ITM2A, or HK3 and LIME1, or HK3 and HLA-DMB, or HK3 and CD7, or HK3 and MAL, or HK3 and TRBV28, or HK3 and RPS29, or GPR84 and IL1RN, or GPR84 and BASP1, or GPR84 and PSTPIP2, or GPR84 and CKAP4, or GPR84 and DYSF, or GPR84 and C19orf59, or GPR84 and IL18R1, or GPR84 and MMP9, or GPR84 and FGR, or GPR84 and SPI1, or GPR84 and PGLYRP1, or GPR84 and RNF24, or GPR84 and ANKRD22, or GPR84 and CEBPD, or GPR84 and IL1R2, or GPR84 and LOC729021 (SRCAP-like helicase), or GPR84 and S100A12, or GPR84 and ITGAM, or GPR84 and FCGR1A, or GPR84 and IFITM3, or GPR84 and CSF3R, or GPR84 and LCN2, or GPR84 and TNFAIP6, or GPR84 and HP, or GPR84 and ORM1, or GPR84 and CEACAM1, or GPR84 and PRTN3, or GPR84 and LRRN3, or GPR84 and GRAP, or GPR84 and TRAJ17, or GPR84 and CD3D, or GPR84 and CD247, or GPR84 and ITM2A, or GPR84 and LIME1, or GPR84 and HLA-DMB, or GPR84 and CD7, or GPR84 and MAL, or GPR84 and TRBV28, or GPR84 and RPS29, or PFKFB3 and IL1RN, or PFKFB3 and BASP1, or PFKFB3 and PSTPIP2, or PFKFB3 and CKAP4, or PFKFB3 and DYSF, or PFKFB3 and C19orf59, or PFKFB3 and IL18R1, or PFKFB3 and MMP9, or PFKFB3 and FGR, or PFKFB3 and SPI1, or PFKFB3 and PGLYRP1, or PFKFB3 and RNF24, or PFKFB3 and ANKRD22, or PFKFB3 and CEBPD, or PFKFB3 and IL1R2, or PFKFB3 and LOC729021 (SRCAP-like helicase), or PFKFB3 and S100A12, or PFKFB3 and ITGAM, or PFKFB3 and FCGR1A, or PFKFB3 and IFITM3, or PFKFB3 and CSF3R, or PFKFB3 and LCN2, or PFKFB3 and TNFAIP6, or PFKFB3 and HP, or PFKFB3 and ORM1, or PFKFB3 and CEACAM1, or PFKFB3 and PRTN3, or PFKFB3 and LRRN3, or PFKFB3 and GRAP, or PFKFB3 and TRAJ17, or PFKFB3 and CD3D, or PFKFB3 and CD247, or PFKFB3 and ITM2A, or PFKFB3 and LIME1, or PFKFB3 and HLA-DMB, or PFKFB3 and CD7, or PFKFB3 and MAL, or PFKFB3 and TRBV28, or PFKFB3 and RPS29, or RETN and IL1RN, or RETN and BASP1, or RETN and PSTPIP2, or RETN and CKAP4, or RETN and DYSF, or RETN and C19orf59, or RETN and IL18R1, or RETN and MMP9, or RETN and FGR, or RETN and SPI1, or RETN and PGLYRP1, or RETN and RNF24, or RETN and ANKRD22, or RETN and CEBPD, or RETN and IL1R2, or RETN and LOC729021 (SRCAP-like helicase), or RETN and S100A12, or RETN and ITGAM, or RETN and FCGR1A, or RETN and IFITM3, or RETN and CSF3R, or RETN and LCN2, or RETN and TNFAIP6, or RETN and HP, or RETN and ORM1, or RETN and CEACAM1, or RETN and PRTN3, or RETN and LRRN3, or RETN and GRAP, or RETN and TRAJ17, or RETN and CD3D, or RETN and CD247, or RETN and ITM2A, or RETN and LIME1, or RETN and HLA-DMB, or RETN and CD7, or RETN and MAL, or RETN and TRBV28, or RETN and RPS29, or STXBP2 and IL1RN, or STXBP2 and BASP1, or STXBP2 and PSTPIP2, or STXBP2 and CKAP4, or STXBP2 and DYSF, or STXBP2 and C19orf59, or STXBP2 and IL18R1, or STXBP2 and MMP9, or STXBP2 and FGR, or STXBP2 and SPI1, or STXBP2 and PGLYRP1, or STXBP2 and RNF24, or STXBP2 and ANKRD22, or STXBP2 and CEBPD, or STXBP2 and IL1R2, or STXBP2 and LOC729021 (SRCAP-like helicase), or STXBP2 and S100A12, or STXBP2 and ITGAM, or STXBP2 and FCGR1A, or STXBP2 and IFITM3, or STXBP2 and CSF3R, or STXBP2 and LCN2, or STXBP2 and TNFAIP6, or STXBP2 and HP, or STXBP2 and ORM1, or STXBP2 and CEACAM1, or STXBP2 and PRTN3, or STXBP2 and LRRN3, or STXBP2 and GRAP, or STXBP2 and TRAJ17, or STXBP2 and CD3D, or STXBP2 and CD247, or STXBP2 and ITM2A, or STXBP2 and LIME1, or STXBP2 and HLA-DMB, or STXBP2 and CD7, or STXBP2 and MAL, or STXBP2 and TRBV28, or STXBP2 and RPS29, or FPR2 and IL1RN, or FPR2 and BASP1, or FPR2 and PSTPIP2, or FPR2 and CKAP4, or FPR2 and DYSF, or FPR2 and C19orf59, or FPR2 and IL18R1, or FPR2 and MMP9, or FPR2 and FGR, or FPR2 and SPI1, or FPR2 and PGLYRP1, or FPR2 and RNF24, or FPR2 and ANKRD22, or FPR2 and CEBPD, or FPR2 and IL1R2, or FPR2 and LOC729021 (SRCAP-like helicase), or FPR2 and S100A12, or FPR2 and ITGAM, or FPR2 and FCGR1A, or FPR2 and IFITM3, or FPR2 and CSF3R, or FPR2 and LCN2, or FPR2 and TNFAIP6, or FPR2 and HP, or FPR2 and ORM1, or FPR2 and CEACAM1, or FPR2 and PRTN3, or FPR2 and LRRN3, or FPR2 and GRAP, or FPR2 and TRAJ17, or FPR2 and CD3D, or FPR2 and CD247, or FPR2 and ITM2A, or FPR2 and LIME1, or FPR2 and HLA-DMB, or FPR2 and CD7, or FPR2 and MAL, or FPR2 and TRBV28, or FPR2 and RPS29, or ALPL and IL1RN, or ALPL and BASP1, or ALPL and PSTPIP2, or ALPL and CKAP4, or ALPL and DYSF, or ALPL and C19orf59, or ALPL and IL18R1, or ALPL and MMP9, or ALPL and FGR, or ALPL and SPI1, or ALPL and PGLYRP1, or ALPL and RNF24, or ALPL and ANKRD22, or ALPL and CEBPD, or ALPL and IL1R2, or ALPL and LOC729021 (SRCAP-like helicase), or ALPL and S100A12, or ALPL and ITGAM, or ALPL and FCGR1A, or ALPL and IFITM3, or ALPL and CSF3R, or ALPL and LCN2, or ALPL and TNFAIP6, or ALPL and HP, or ALPL and ORM1, or ALPL and CEACAM1, or ALPL and PRTN3, or ALPL and LRRN3, or ALPL and GRAP, or ALPL and TRAJ17, or ALPL and CD3D, or ALPL and CD247, or ALPL and ITM2A, or ALPL and LIME1, or ALPL and HLA-DMB, or ALPL and CD7, or ALPL and MAL, or ALPL and TRBV28, or ALPL and RPS29, or GRINA and IL1RN, or GRINA and BASP1, or GRINA and PSTPIP2, or GRINA and CKAP4, or GRINA and DYSF, or GRINA and C19orf59, or GRINA and IL18R1, or GRINA and MMP9, or GRINA and FGR, or GRINA and SPI1, or GRINA and PGLYRP1, or GRINA and RNF24, or GRINA and ANKRD22, or GRINA and CEBPD, or GRINA and IL1R2, or GRINA and LOC729021 (SRCAP-like helicase), or GRINA and S100A12, or GRINA and ITGAM, or GRINA and FCGR1A, or GRINA and IFITM3, or GRINA and CSF3R, or GRINA and LCN2, or GRINA and TNFAIP6, or GRINA and HP, or GRINA and ORM1, or GRINA and CEACAM1, or GRINA and PRTN3, or GRINA and LRRN3, or GRINA and GRAP, or GRINA and TRAJ17, or GRINA and CD3D, or GRINA and CD247, or GRINA and ITM2A, or GRINA and LIME1, or GRINA and HLA-DMB, or GRINA and CD7, or GRINA and MAL, or GRINA and TRBV28, or GRINA and RPS29, or FFAR2 and IL1RN, or FFAR2 and BASP1, or FFAR2 and PSTPIP2, or FFAR2 and CKAP4, or FFAR2 and DYSF, or FFAR2 and C19orf59, or FFAR2 and IL18R1, or FFAR2 and MMP9, or FFAR2 and FGR, or FFAR2 and SPI1, or FFAR2 and PGLYRP1, or FFAR2 and RNF24, or FFAR2 and ANKRD22, or FFAR2 and CEBPD, or FFAR2 and IL1R2, or FFAR2 and LOC729021 (SRCAP-like helicase), or FFAR2 and S100A12, or FFAR2 and ITGAM, or FFAR2 and FCGR1A, or FFAR2 and IFITM3, or FFAR2 and CSF3R, or FFAR2 and LCN2, or FFAR2 and TNFAIP6, or FFAR2 and HP, or FFAR2 and ORM1, or FFAR2 and CEACAM1, or FFAR2 and PRTN3, or FFAR2 and LRRN3, or FFAR2 and GRAP, or FFAR2 and TRAJ17, or FFAR2 and CD3D, or FFAR2 and CD247, or FFAR2 and ITM2A, or FFAR2 and LIME1, or FFAR2 and HLA-DMB, or FFAR2 and CD7, or FFAR2 and MAL, or FFAR2 and TRBV28, or FFAR2 and RPS29, or MPO and IL1RN, or MPO and BASP1, or MPO and PSTPIP2, or MPO and CKAP4, or MPO and DYSF, or MPO and C19orf59, or MPO and IL18R1, or MPO and MMP9, or MPO and FGR, or MPO and SPI1, or MPO and PGLYRP1, or MPO and RNF24, or MPO and ANKRD22, or MPO and CEBPD, or MPO and IL1R2, or MPO and LOC729021 (SRCAP-like helicase), or MPO and S100A12, or MPO and ITGAM, or MPO and FCGR1A, or MPO and IFITM3, or MPO and CSF3R, or MPO and LCN2, or MPO and TNFAIP6, or MPO and HP, or MPO and ORM1, or MPO and CEACAM1, or MPO and PRTN3, or MPO and LRRN3, or MPO and GRAP, or MPO and TRAJ17, or MPO and CD3D, or MPO and CD247, or MPO and ITM2A, or MPO and LIME1, or MPO and HLA-DMB, or MPO and CD7, or MPO and MAL, or MPO and TRBV28, or MPO and RPS29; or IL1RN and BASP1, or IL1RN and PSTPIP2, or IL1RN and CKAP4, or IL1RN and DYSF, or IL1RN and C19orf59, or IL1RN and IL18R1, or IL1RN and MMP9, or IL1RN and FGR, or IL1RN and SPI1, or IL1RN and PGLYRP1, or IL1RN and RNF24, or IL1RN and ANKRD22, or IL1RN and CEBPD, or IL1RN and IL1R2, or IL1RN and LOC729021 (SRCAP-like helicase), or IL1RN and S100A12, or IL1RN and ITGAM, or IL1RN and FCGR1A, or IL1RN and IFITM3, or IL1RN and CSF3R, or IL1RN and LCN2, or IL1RN and TNFAIP6, or IL1RN and HP, or IL1RN and ORM1, or IL1RN and CEACAM1, or IL1RN and PRTN3, or BASP1 and PSTPIP2, or BASP1 and CKAP4, or BASP1 and DYSF, or BASP1 and C19orf59, or BASP1 and IL18R1, or BASP1 and MMP9, or BASP1 and FGR, or BASP1 and SPI1, or BASP1 and PGLYRP1, or BASP1 and RNF24, or BASP1 and ANKRD22, or BASP1 and CEBPD, or BASP1 and IL1R2, or BASP1 and LOC729021 (SRCAP-like helicase), or BASP1 and S100A12, or BASP1 and ITGAM, or BASP1 and FCGR1A, or BASP1 and IFITM3, or BASP1 and CSF3R, or BASP1 and LCN2, or BASP1 and TNFAIP6, or BASP1 and HP, or BASP1 and ORM1, or BASP1 and CEACAM1, or BASP1 and PRTN3, or PSTPIP2 and CKAP4, or PSTPIP2 and DYSF, or PSTPIP2 and C19orf59, or PSTPIP2 and IL18R1, or PSTPIP2 and MMP9, or PSTPIP2 and FGR, or PSTPIP2 and SPI1, or PSTPIP2 and PGLYRP1, or PSTPIP2 and RNF24, or PSTPIP2 and ANKRD22, or PSTPIP2 and CEBPD, or PSTPIP2 and IL1R2, or PSTPIP2 and LOC729021 (SRCAP-like helicase), or PSTPIP2 and S100A12, or PSTPIP2 and ITGAM, or PSTPIP2 and FCGR1A, or PSTPIP2 and IFITM3, or PSTPIP2 and CSF3R, or PSTPIP2 and LCN2, or PSTPIP2 and TNFAIP6, or PSTPIP2 and HP, or PSTPIP2 and ORM1, or PSTPIP2 and CEACAM1, or PSTPIP2 and PRTN3, or CKAP4 and DYSF, or CKAP4 and C19orf59, or CKAP4 and IL18R1, or CKAP4 and MMP9, or CKAP4 and FGR, or CKAP4 and SPI1, or CKAP4 and PGLYRP1, or CKAP4 and RNF24, or CKAP4 and ANKRD22, or CKAP4 and CEBPD, or CKAP4 and IL1R2, or CKAP4 and LOC729021 (SRCAP-like helicase), or CKAP4 and S100A12, or CKAP4 and ITGAM, or CKAP4 and FCGR1A, or CKAP4 and IFITM3, or CKAP4 and CSF3R, or CKAP4 and LCN2, or CKAP4 and TNFAIP6, or CKAP4 and HP, or CKAP4 and ORM1, or CKAP4 and CEACAM1, or CKAP4 and PRTN3, or DYSF and C19orf59, or DYSF and IL18R1, or DYSF and MMP9, or DYSF and FGR, or DYSF and SPI1, or DYSF and PGLYRP1, or DYSF and RNF24, or DYSF and ANKRD22, or DYSF and CEBPD, or DYSF and IL1R2, or DYSF and LOC729021 (SRCAP-like helicase), or DYSF and S100A12, or DYSF and ITGAM, or DYSF and FCGR1A, or DYSF and IFITM3, or DYSF and CSF3R, or DYSF and LCN2, or DYSF and TNFAIP6, or DYSF and HP, or DYSF and ORM1, or DYSF and CEACAM1, or DYSF and PRTN3, or C19orf59 and IL18R1, or C19orf59 and MMP9, or C19orf59 and FGR, or C19orf59 and SPI1, or C19orf59 and PGLYRP1, or C19orf59 and RNF24, or C19orf59 and ANKRD22, or C19orf59 and CEBPD, or C19orf59 and IL1R2, or C19orf59 and LOC729021 (SRCAP-like helicase), or C19orf59 and S100A12, or C19orf59 and ITGAM, or C19orf59 and FCGR1A, or C19orf59 and IFITM3, or C19orf59 and CSF3R, or C19orf59 and LCN2, or C19orf59 and TNFAIP6, or C19orf59 and HP, or C19orf59 and ORM1, or C19orf59 and CEACAM1, or C19orf59 and PRTN3, or IL18R1 and MMP9, or IL18R1 and FGR, or IL18R1 and SPI1, or IL18R1 and PGLYRP1, or IL18R1 and RNF24, or IL18R1 and ANKRD22, or IL18R1 and CEBPD, or IL18R1 and IL1R2, or IL18R1 and LOC729021 (SRCAP-like helicase), or IL18R1 and S100A12, or IL18R1 and ITGAM, or IL18R1 and FCGR1A, or IL18R1 and IFITM3, or IL18R1 and CSF3R, or IL18R1 and LCN2, or IL18R1 and TNFAIP6, or IL18R1 and HP, or IL18R1 and ORM1, or IL18R1 and CEACAM1, or IL18R1 and PRTN3, or MMP9 and FGR, or MMP9 and SPI1, or MMP9 and PGLYRP1, or MMP9 and RNF24, or MMP9 and ANKRD22, or MMP9 and CEBPD, or MMP9 and IL1R2, or MMP9 and LOC729021 (SRCAP-like helicase), or MMP9 and S100A12, or MMP9 and ITGAM, or MMP9 and FCGR1A, or MMP9 and IFITM3, or MMP9 and CSF3R, or MMP9 and LCN2, or MMP9 and TNFAIP6, or MMP9 and HP, or MMP9 and ORM1, or MMP9 and CEACAM1, or MMP9 and PRTN3, or FGR and SPI1, or FGR and PGLYRP1, or FGR and RNF24, or FGR and ANKRD22, or FGR and CEBPD, or FGR and IL1R2, or FGR and LOC729021 (SRCAP-like helicase), or FGR and S100A12, or FGR and ITGAM, or FGR and FCGR1A, or FGR and IFITM3, or FGR and CSF3R, or FGR and LCN2, or FGR and TNFAIP6, or FGR and HP, or FGR and ORM1, or FGR and CEACAM1, or FGR and PRTN3, or SPI1 and PGLYRP1, or SPI1 and RNF24, or SPI1 and ANKRD22, or SPI1 and CEBPD, or SPI1 and IL1R2, or SPI1 and LOC729021 (SRCAP-like helicase), or SPI1 and S100A12, or SPI1 and ITGAM, or SPI1 and FCGR1A, or SPI1 and IFITM3, or SPI1 and CSF3R, or SPI1 and LCN2, or SPI1 and TNFAIP6, or SPI1 and HP, or SPI1 and ORM1, or SPI1 and CEACAM1, or SPI1 and PRTN3, or PGLYRP1 and RNF24, or PGLYRP1 and ANKRD22, or PGLYRP1 and CEBPD, or PGLYRP1 and IL1R2, or PGLYRP1 and LOC729021 (SR-CAP-like helicase), or PGLYRP1 and S100A12, or PGLYRP1 and ITGAM, or PGLYRP1 and FCGR1A, or PGLYRP1 and IFITM3, or PGLYRP1 and CSF3R, or PGLYRP1 and LCN2, or PGLYRP1 and TNFAIP6, or PGLYRP1 and HP, or PGLYRP1 and ORM1, or PGLYRP1 and CEACAM1, or PGLYRP1 and PRTN3, or RNF24 and ANKRD22, or RNF24 and CEBPD, or RNF24 and IL1R2, or RNF24 and LOC729021 (SRCAP-like helicase), or RNF24 and S100A12, or RNF24 and ITGAM, or RNF24 and FCGR1A, or RNF24 and IFITM3, or RNF24 and CSF3R, or RNF24 and LCN2, or RNF24 and TNFAIP6, or RNF24 and HP, or RNF24 and ORM1, or RNF24 and CEACAM1, or RNF24 and PRTN3, or ANKRD22 and CEBPD, or ANKRD22 and IL1R2, or ANKRD22 and LOC729021 (SRCAP-like helicase), or ANKRD22 and S100A12, or ANKRD22 and ITGAM, or ANKRD22 and FCGR1A, or ANKRD22 and IFITM3, or ANKRD22 and CSF3R, or ANKRD22 and LCN2, or ANKRD22 and TNFAIP6, or ANKRD22 and HP, or ANKRD22 and ORM1, or ANKRD22 and CEACAM1, or ANKRD22 and PRTN3, or CEBPD and IL1R2, or CEBPD and LOC729021 (SR-CAP-like helicase), or CEBPD and S100A12, or CEBPD and ITGAM, or CEBPD and FCGR1A, or CEBPD and IFITM3, or CEBPD and CSF3R, or CEBPD and LCN2, or CEBPD and TNFAIP6, or CEBPD and HP, or CEBPD and ORM1, or CEBPD and CEACAM1, or CEBPD and PRTN3, or IL1R2 and LOC729021 (SRCAP-like helicase), or IL1R2 and S100A12, or IL1R2 and ITGAM, or IL1R2 and FCGR1A, or IL1R2 and IFITM3, or IL1R2 and CSF3R, or IL1R2 and LCN2, or IL1R2 and TNFAIP6, or IL1R2 and HP, or IL1R2 and ORM1, or IL1R2 and CEACAM1, or IL1R2 and PRTN3, or LOC729021 (SRCAP-like helicase) and S100A12, or LOC729021 (SRCAP-like helicase) and ITGAM, or LOC729021 (SRCAP-like helicase) and FCGR1A, or LOC729021 (SRCAP-like helicase) and IFITM3, or LOC729021 (SRCAP-like helicase) and CSF3R, or LOC729021 (SRCAP-like helicase) and LCN2, or LOC729021 (SRCAP-like helicase) and TNFAIP6, or LOC729021 (SRCAP-like helicase) and HP, or LOC729021 (SRCAP-like helicase) and ORM1, or LOC729021 (SRCAP-like helicase) and CEACAM1, or LOC729021 (SR-CAP-like helicase) and PRTN3, or S100A12 and ITGAM, or S100A12 and FCGR1A, or S100A12 and IFITM3, or S100A12 and CSF3R, or S100A12 and LCN2, or S100A12 and TNFAIP6, or S100A12 and HP, or S100A12 and ORM1, or S100A12 and CEACAM1, or S100A12 and PRTN3, or ITGAM and FCGR1A, or ITGAM and IFITM3, or ITGAM and CSF3R, or ITGAM and LCN2, or ITGAM and TNFAIP6, or ITGAM and HP, or ITGAM and ORM1, or ITGAM and CEACAM1, or ITGAM and PRTN3, or FCGR1A and IFITM3, or FCGR1A and CSF3R, or FCGR1A and LCN2, or FCGR1A and TNFAIP6, or FCGR1A and HP, or FCGR1A and ORM1, or FCGR1A and CEACAM1, or FCGR1A and PRTN3, or IFITM3 and CSF3R, or IFITM3 and LCN2, or IFITM3 and TNFAIP6, or IFITM3 and HP, or IFITM3 and ORM1, or IFITM3 and CEACAM1, or IFITM3 and PRTN3, or CSF3R and LCN2, or CSF3R and TNFAIP6, or CSF3R and HP, or CSF3R and ORM1, or CSF3R and CEACAM1, or CSF3R and PRTN3, or LCN2 and TNFAIP6, or LCN2 and HP, or LCN2 and ORM1, or LCN2 and CEACAM1, or LCN2 and PRTN3, or TNFAIP6 and HP, or TNFAIP6 and ORM1, or TNFAIP6 and CEACAM1, or TNFAIP6 and PRTN3, or HP and ORM1, or HP and CEACAM1, or HP and PRTN3, or ORM1 and CEACAM1, or ORM1 and PRTN3, or CEACAM1 and PRTN3; or IL1RN and LRRN3, or IL1RN and GRAP, or IL1RN and TRAJ17, or IL1RN and CD3D, or IL1RN and CD247, or IL1RN and ITM2A, or IL1RN and LIME1, or IL1RN and HLA-DMB, or IL1RN and CD7, or IL1RN and MAL, or IL1RN and TRBV28, or IL1RN and RPS29, or BASP1 and LRRN3, or BASP1 and GRAP, or BASP1 and TRAJ17, or BASP1 and CD3D, or BASP1 and CD247, or BASP1 and ITM2A, or BASP1 and LIME1, or BASP1 and HLA-DMB, or BASP1 and CD7, or BASP1 and MAL, or BASP1 and TRBV28, or BASP1 and RPS29, or PSTPIP2 and LRRN3, or PSTPIP2 and GRAP, or PSTPIP2 and TRAJ17, or PSTPIP2 and CD3D, or PSTPIP2 and CD247, or PSTPIP2 and ITM2A, or PSTPIP2 and LIME1, or PSTPIP2 and HLA-DMB, or PSTPIP2 and CD7, or PSTPIP2 and MAL, or PSTPIP2 and TRBV28, or PSTPIP2 and RPS29, or CKAP4 and LRRN3, or CKAP4 and GRAP, or CKAP4 and TRAJ17, or CKAP4 and CD3D, or CKAP4 and CD247, or CKAP4 and ITM2A, or CKAP4 and LIME1, or CKAP4 and HLA-DMB, or CKAP4 and CD7, or CKAP4 and MAL, or CKAP4 and TRBV28, or CKAP4 and RPS29, or DYSF and LRRN3, or DYSF and GRAP, or DYSF and TRAJ17, or DYSF and CD3D, or DYSF and CD247, or DYSF and ITM2A, or DYSF and LIME1, or DYSF and HLA-DMB, or DYSF and CD7, or DYSF and MAL, or DYSF and TRBV28, or DYSF and RPS29, or C19orf59 and LRRN3, or C19orf59 and GRAP, or C19orf59 and TRAJ17, or C19orf59 and CD3D, or C19orf59 and CD247, or C19orf59 and ITM2A, or C19orf59 and LIME1, or C19orf59 and HLA-DMB, or C19orf59 and CD7, or C19orf59 and MAL, or C19orf59 and TRBV28, or C19orf59 and RPS29, or IL18R1 and LRRN3, or IL18R1 and GRAP, or IL18R1 and TRAJ17, or IL18R1 and CD3D, or IL18R1 and CD247, or IL18R1 and ITM2A, or IL18R1 and LIME1, or IL18R1 and HLA-DMB, or IL18R1 and CD7, or IL18R1 and MAL, or IL18R1 and TRBV28, or IL18R1 and RPS29, or MMP9 and LRRN3, or MMP9 and GRAP, or MMP9 and TRAJ17, or MMP9 and CD3D, or MMP9 and CD247, or MMP9 and ITM2A, or MMP9 and LIME1, or MMP9 and HLA-DMB, or MMP9 and CD7, or MMP9 and MAL, or MMP9 and TRBV28, or MMP9 and RPS29, or FGR and LRRN3, or FGR and GRAP, or FGR and TRAJ17, or FGR and CD3D, or FGR and CD247, or FGR and ITM2A, or FGR and LIME1, or FGR and HLA-DMB, or FGR and CD7, or FGR and MAL, or FGR and TRBV28, or FGR and RPS29, or SPI1 and LRRN3, or SPI1 and GRAP, or SPI1 and TRAJ17, or SPI1 and CD3D, or SPI1 and CD247, or SPI1 and ITM2A, or SPI1 and LIME1, or SPI1 and HLA-DMB, or SPI1 and CD7, or SPI1 and MAL, or SPI1 and TRBV28, or SPI1 and RPS29, or PGLYRP1 and LRRN3, or PGLYRP1 and GRAP, or PGLYRP1 and TRAJ17, or PGLYRP1 and CD3D, or PGLYRP1 and CD247, or PGLYRP1 and ITM2A, or PGLYRP1 and LIME1, or PGLYRP1 and HLA-DMB, or PGLYRP1 and CD7, or PGLYRP1 and MAL, or PGLYRP1 and TRBV28, or PGLYRP1 and RPS29, or RNF24 and LRRN3, or RNF24 and GRAP, or RNF24 and TRAJ17, or RNF24 and CD3D, or RNF24 and CD247, or RNF24 and ITM2A, or RNF24 and LIME1, or RNF24 and HLA-DMB, or RNF24 and CD7, or RNF24 and MAL, or RNF24 and TRBV28, or RNF24 and RPS29, or ANKRD22 and LRRN3, or ANKRD22 and GRAP, or ANKRD22 and TRAJ17, or ANKRD22 and CD3D, or ANKRD22 and CD247, or ANKRD22 and ITM2A, or ANKRD22 and LIME1, or ANKRD22 and HLA-DMB, or ANKRD22 and CD7, or ANKRD22 and MAL, or ANKRD22 and TRBV28, or ANKRD22 and RPS29, or CEBPD and LRRN3, or CEBPD and GRAP, or CEBPD and TRAJ17, or CEBPD and CD3D, or CEBPD and CD247, or CEBPD and ITM2A, or CEBPD and LIME1, or CEBPD and HLA-DMB, or CEBPD and CD7, or CEBPD and MAL, or CEBPD and TRBV28, or CEBPD and RPS29, or IL1R2 and LRRN3, or IL1R2 and GRAP, or IL1R2 and TRAJ17, or IL1R2 and CD3D, or IL1R2 and CD247, or IL1R2 and ITM2A, or IL1R2 and LIME1, or IL1R2 and HLA-DMB, or IL1R2 and CD7, or IL1R2 and MAL, or IL1R2 and TRBV28, or IL1R2 and RPS29, or LOC729021 (SRCAP-like helicase) and LRRN3, or LOC729021 (SRCAP-like helicase) and GRAP, or LOC729021 (SRCAP-like helicase) and TRAJ17, or LOC729021 (SRCAP-like helicase) and CD3D, or LOC729021 (SRCAP-like helicase) and CD247, or LOC729021 (SRCAP-like helicase) and ITM2A, or LOC729021 (SRCAP-like helicase) and LIME1, or LOC729021 (SRCAP-like helicase) and HLA-DMB, or LOC729021 (SRCAP-like helicase) and CD7, or LOC729021 (SRCAP-like helicase) and MAL, or LOC729021 (SRCAP-like helicase) and TRBV28, or LOC729021 (SRCAP-like helicase) and RPS29, or S100A12 and LRRN3, or S100A12 and GRAP, or S100A12 and TRAJ17, or S100A12 and CD3D, or S100A12 and CD247, or S100A12 and ITM2A, or S100A12 and LIME1, or S100A12 and HLA-DMB, or S100A12 and CD7, or S100A12 and MAL, or S100A12 and TRBV28, or S100A12 and RPS29, or ITGAM and LRRN3, or ITGAM and GRAP, or ITGAM and TRAJ17, or ITGAM and CD3D, or ITGAM and CD247, or ITGAM and ITM2A, or ITGAM and LIME1, or ITGAM and HLA-DMB, or ITGAM and CD7, or ITGAM and MAL, or ITGAM and TRBV28, or ITGAM and RPS29, or FCGR1A and LRRN3, or FCGR1A and GRAP, or FCGR1A and TRAJ17, or FCGR1A and CD3D, or FCGR1A and CD247, or FCGR1A and ITM2A, or FCGR1A and LIME1, or FCGR1A and HLA-DMB, or FCGR1A and CD7, or FCGR1A and MAL, or FCGR1A and TRBV28, or FCGR1A and RPS29, or IFITM3 and LRRN3, or IFITM3 and GRAP, or IFITM3 and TRAJ17, or IFITM3 and CD3D, or IFITM3 and CD247, or IFITM3 and ITM2A, or IFITM3 and LIME1, or IFITM3 and HLA-DMB, or IFITM3 and CD7, or IFITM3 and MAL, or IFITM3 and TRBV28, or IFITM3 and RPS29, or CSF3R and LRRN3, or CSF3R and GRAP, or CSF3R and TRAJ17, or CSF3R and CD3D, or CSF3R and CD247, or CSF3R and ITM2A, or CSF3R and LIME1, or CSF3R and HLA-DMB, or CSF3R and CD7, or CSF3R and MAL, or CSF3R and TRBV28, or CSF3R and RPS29, or LCN2 and LRRN3, or LCN2 and GRAP, or LCN2 and TRAJ17, or LCN2 and CD3D, or LCN2 and CD247, or LCN2 and ITM2A, or LCN2 and LIME1, or LCN2 and HLA-DMB, or LCN2 and CD7, or LCN2 and MAL, or LCN2 and TRBV28, or LCN2 and RPS29, or TNFAIP6 and LRRN3, or TNFAIP6 and GRAP, or TNFAIP6 and TRAJ17, or TNFAIP6 and CD3D, or TNFAIP6 and CD247, or TNFAIP6 and ITM2A, or TNFAIP6 and LIME1, or TNFAIP6 and HLA-DMB, or TNFAIP6 and CD7, or TNFAIP6 and MAL, or TNFAIP6 and TRBV28, or TNFAIP6 and RPS29, or HP and LRRN3, or HP and GRAP, or HP and TRAJ17, or HP and CD3D, or HP and CD247, or HP and ITM2A, or HP and LIME1, or HP and HLA-DMB, or HP and CD7, or HP and MAL, or HP and TRBV28, or HP and RPS29, or ORM1 and LRRN3, or ORM1 and GRAP, or ORM1 and TRAJ17, or ORM1 and CD3D, or ORM1 and CD247, or ORM1 and ITM2A, or ORM1 and LIME1, or ORM1 and HLA-DMB, or ORM1 and CD7, or ORM1 and MAL, or ORM1 and TRBV28, or ORM1 and RPS29, or CEACAM1 and LRRN3, or CEACAM1 and GRAP, or CEACAM1 and TRAJ17, or CEACAM1 and CD3D, or CEACAM1 and CD247, or CEACAM1 and ITM2A, or CEACAM1 and LIME1, or CEACAM1 and HLA-DMB, or CEACAM1 and CD7, or CEACAM1 and MAL, or CEACAM1 and TRBV28, or CEACAM1 and RPS29, or PRTN3 and LRRN3, or PRTN3 and GRAP, or PRTN3 and TRAJ17, or PRTN3 and CD3D, or PRTN3 and CD247, or PRTN3 and ITM2A, or PRTN3 and LIME1, or PRTN3 and HLA-DMB, or PRTN3 and CD7, or PRTN3 and MAL, or PRTN3 and TRBV28, or PRTN3 and RPS29; or LRRN3 and GRAP, or LRRN3 and TRAJ17, or LRRN3 and CD3D, or LRRN3 and CD247, or LRRN3 and ITM2A, or LRRN3 and LIME1, or LRRN3 and HLA-DMB, or LRRN3 and CD7, or LRRN3 and MAL, or LRRN3 and TRBV28, or LRRN3 and RPS29, or GRAP and TRAJ17, or GRAP and CD3D, or GRAP and CD247, or GRAP and ITM2A, or GRAP and LIME1, or GRAP and HLA-DMB, or GRAP and CD7, or GRAP and MAL, or GRAP and TRBV28, or GRAP and RPS29, or TRAJ17 and CD3D, or TRAJ17 and CD247, or TRAJ17 and ITM2A, or TRAJ17 and LIME1, or TRAJ17 and HLA-DMB, or TRAJ17 and CD7, or TRAJ17 and MAL, or TRAJ17 and TRBV28, or TRAJ17 and RPS29, or CD3D and CD247, or CD3D and ITM2A, or CD3D and LIME1, or CD3D and HLA-DMB, or CD3D and CD7, or CD3D and MAL, or CD3D and TRBV28, or CD3D and RPS29, or CD247 and ITM2A, or CD247 and LIME1, or CD247 and HLA-DMB, or CD247 and CD7, or CD247 and MAL, or CD247 and TRBV28, or CD247 and RPS29, or ITM2A and LIME1, or ITM2A and HLA-DMB, or ITM2A and CD7, or ITM2A and MAL, or ITM2A and TRBV28, or ITM2A and RPS29, or LIME1 and HLA-DMB, or LIME1 and CD7, or LIME1 and MAL, or LIME1 and TRBV28, or LIME1 and RPS29, or HLA-DMB and CD7, or HLA-DMB and MAL, or HLA-DMB and TRBV28, or HLA-DMB and RPS29, or CD7 and MAL, or CD7 and TRBV28, or CD7 and RPS29, or MAL and TRBV28, or MAL and RPS29, or RPS29 and TRBV28.

In another embodiment the present invention provides a method of diagnosing sepsis as set out above, wherein at least one biomarker listed in Table 1 is selected from each of groups A, B and C. Preferably the levels of at least one biomarker from each of the three biomarker groups will be analysed. Preferably at least two biomarkers from each group will be analysed. More preferably at least 3 biomarkers from each group will be analysed. Suitably the levels of all biomarkers from each of the three groups will be analysed.

TABLE 1

Differentially expressed biomarkers which make up the network categorised by pathway.

| Group A: Metabolic | Group B: Innate Immune | Group C: Adaptive Immune |
|---|---|---|
| GYG1 | IL1RN | LRRN3 |
| B4GALT5 | BASP1 | GRAP |
| SLC2A3 | PSTPIP2 | TRAJ17 |
| HK3 | CKAP4 | CD3D |
| GPR84 | DYSF | CD247 |
| PFKFB3 | C19orf59 | ITM2A |
| RETN | IL18R1 | LIME1 |
| STXBP2 | MMP9 | HLA-DMB |
| FPR2 | FGR | CD7 |
| ALPL | SPI1 | MAL |
| GRINA | PGLYRP1 | TRBV28 |
| FFAR2 | RNF24 | RPS29 |
| MPO | ANKRD22 | |
| | CEBPD | |
| | IL1R2 | |
| | LOC729021 (SRCAP-like helicase) | |
| | S100A12 | |
| | ITGAM | |
| | FCGR1A | |
| | IFITM3 | |
| | CSF3R | |
| | LCN2 | |
| | TNFAIP6 | |
| | HP | |
| | ORM1 | |
| | CEACAM1 | |
| | PRTN3 | |

(Sequences for all of these biomarkers can be obtained from NCBI RefSeq Release 38, and these reference sequences were used in preparation of the arrays discussed in the experimental work below).

TABLE 2

Biomarkers which make up the network categorised by pathway and ranked by individual ability to differentiate between sepsis and non-sepsis as obtained through Receiver-Operating-Characteristics (ROC).

| Group | Symbol | Pathway | AUC | Sens (%) | Spec (%) |
|---|---|---|---|---|---|
| Metabolic | GYG1 | Metabolic | 1 | 100 | 100 |
| | B4GALT5 | Metabolic | 1 | 100 | 100 |
| | SLC2A3 | Metabolic | 1 | 100 | 100 |
| | HK3 | Metabolic | 0.999 | 100 | 97.1 |
| | GPR84 | Metabolic | 0.995 | 96.3 | 97.1 |
| | PFKFB3 | Metabolic | 0.993 | 100 | 91.4 |
| | RETN | Metabolic | 0.988 | 100 | 94.3 |
| | STXBP2 | Metabolic | 0.988 | 92.6 | 97.1 |
| | FPR2 | Metabolic | 0.985 | 96.3 | 91.4 |
| | ALPL | Metabolic | 0.974 | 96.3 | 88.6 |
| | GRINA | Metabolic | 0.937 | 85.2 | 85.7 |
| | FFAR2 | Metabolic | 0.933 | 96.3 | 74.3 |
| | MPO | Metabolic | 0.914 | 74.1 | 94.3 |
| Innate Immune | IL1RN | Innate | 1 | 100 | 100 |
| | BASP1 | Innate | 0.999 | 100 | 97.1 |
| | PSTPIP2 | Innate | 0.999 | 100 | 97.1 |
| | CKAP4 | Innate | 0.995 | 96.3 | 100 |
| | DYSF | Innate | 0.994 | 96.3 | 100 |
| | C19orf59 | Innate | 0.994 | 100 | 94.3 |
| | IL18R1 | Innate | 0.994 | 96.3 | 97.1 |

TABLE 2-continued

Biomarkers which make up the network categorised by pathway and ranked by individual ability to differentiate between sepsis and non-sepsis as obtained through Receiver-Operating-Characteristics (ROC).

| Group | Symbol | Pathway | AUC | Sens (%) | Spec (%) |
|---|---|---|---|---|---|
| | MMP9 | Innate | 0.989 | 88.9 | 100 |
| | FGR | Innate | 0.989 | 96.3 | 100 |
| | SPI1 | Innate | 0.989 | 100 | 94.3 |
| | PGLYRP1 | Innate | 0.987 | 100 | 94.3 |
| | RNF24 | Innate | 0.985 | 96.3 | 97.1 |
| | ANKRD22 | Innate | 0.984 | 92.6 | 94.3 |
| | CEBPD | Innate | 0.984 | 96.3 | 97.1 |
| | IL1R2 | Innate | 0.983 | 96.3 | 91.4 |
| | LOC729021 (SRCAP-like helicase) | Innate | 0.979 | 92.6 | 97.1 |
| | S100A12 | Innate | 0.978 | 92.6 | 94.3 |
| | ITGAM | Innate | 0.976 | 92.6 | 100 |
| | FCGR1A | Innate | 0.974 | 92.6 | 91.4 |
| | IFITM3 | Innate | 0.968 | 92.6 | 88.6 |
| | CSF3R | Innate | 0.968 | 92.6 | 97.1 |
| | LCN2 | Innate | 0.964 | 88.9 | 94.3 |
| | TNFAIP6 | Innate | 0.956 | 85.2 | 97.1 |
| | HP | Innate | 0.953 | 100 | 82.9 |
| | ORM1 | Innate | 0.952 | 92.6 | 82.9 |
| | CEACAM1 | Innate | 0.946 | 85.2 | 91.4 |
| | PRTN3 | Innate | 0.937 | 85.2 | 91.4 |
| Adaptive Immune | LRRN3 | Adaptive | 1 | 100 | 100 |
| | GRAP | Adaptive | 0.995 | 94.3 | 100 |
| | TRAJ17 | Adaptive | 0.99 | 91.4 | 100 |
| | CD3D | Adaptive | 0.99 | 91.4 | 100 |
| | CD247 | Adaptive | 0.984 | 97.1 | 92.6 |
| | ITM2A | Adaptive | 0.979 | 91.4 | 96.3 |
| | LIME1 | Adaptive | 0.971 | 88.6 | 96.3 |
| | HLA-DMB | Adaptive | 0.96 | 77.1 | 100 |
| | CD7 | Adaptive | 0.96 | 82.9 | 100 |
| | MAL | Adaptive | 0.959 | 88.6 | 96.3 |
| | TRBV28 | Adaptive | 0.952 | 82.9 | 96.3 |
| | RPS29 | Adaptive | 0.874 | 80 | 88.9 |

Abbreviations are as follows;
AUC—Area Under Curve;
Sens (%)—Sensitivity;
Spec (%)—Specificity.
The last four estimators are based on gil.

In some embodiments of the present invention it is preferred that the biomarkers comprise a selection from sub-groups of the biomarkers set out in groups A, B and C. Accordingly:

Preferred biomarkers from Group A are selected from the sub-group A consisting of: MPO, HK3, STXBP2, RETN, GRINA, FPR2, and ALPL.

Preferred biomarkers from Group B are selected from the sub-group B consisting of: MMP9, DYSF, IL1R2, CKAP4, IL18R1, BASP1, CEBPD, FGR, and CSF3R.

Preferred biomarkers from Group C are selected from the sub-group C consisting of: TRAJ17, CD247, ITM2A, CD3D, MAL and TRBV28.

These sub-groups represent preferred selections from within the larger groups of biomarkers, which perform surprisingly well, and can be used to provide very accurate diagnostic methods.

These various marker sub-groups, and various preferred selections from within them, are particularly preferred for use in diagnosing sepsis in adult humans, but they can also be preferred for diagnosing sepsis in neonates and children (including infants). Indeed it is a remarkable feature of the present invention that these biomarkers, and particularly those within the sub-groups mentioned above, have broad utility.

Preferably biomarkers from at least two sub-groups are used (A+B, A+C, or B+C), and suitably biomarkers from all three sub-groups can be used.

Preferably at least five biomarkers selected from the sub-groups are used, and suitably at least six, seven or eight biomarkers from the sub-groups are used.

Where biomarkers from two or more sub-groups are used, preferably at least two biomarkers from each sub-group are used, and more preferably at least three biomarkers from each of the above sub-groups are used.

In a preferred embodiment at least one marker from sub-group A is used in combination with at least two biomarkers from sub-groups B and/or C (suitably three, four, five or six or more biomarkers from sub-group B and/or C). More preferably at least two (suitably three, four, five, six or more) biomarkers from sub-group A are used in combination with at least two biomarkers from sub-group B and/or C.

From sub-group A it is highly preferred that the biomarkers HK3 and MPO are used. In addition to HK3 and MPO, preferably at least one of SLC2A3, STXBP2, RETN, GRINA, FPR2, ALPL GPR84, GYG1 and FFAR2 is used, more preferably at least one of SLC2A3, STXBP2, RETN, GRINA, FPR2 and ALPL is used (suitably at least two, three or four of these additional biomarkers are used).

From sub-group B it is highly preferred that the biomarkers MMP9, IL1R2 and DYSF are used. In addition to MMP9, IL1R2 and DYSF, preferably at least one of CKAP4, IL18R1, BASP1, CEBPD, FGR, PGLYRP1 and CSF3R is used, more preferably at least one of CKAP4, IL18R1, BASP1, CEBPD, FGR and CSF3R is used (suitably at least two, three or four of these additional biomarkers are used).

From sub-group C it is highly preferred that the biomarkers TRAJ17, CD247 and ITM2A are used. In addition to TRAJ17, CD247 and ITM2A, preferably at least one of CD3D, MAL, HLA-DMB and TRBV28 is used, more preferably at least one of CD3D, MAL, and TRBV28 is used (suitably at least two, three or four of these additional biomarkers are used).

Various specific combinations of biomarkers have been identified as resulting in extremely high levels of accuracy (typically 100% accuracy) in test data. Accordingly these specific combinations represent preferred embodiments of the invention, particularly with regard to diagnosis of sepsis in adults, but also in diagnosing sepsis in children (including infants) and neonates.

Accordingly:

In a preferred embodiment the biomarkers comprise:
HK3, MPO and SLC2A3 from group A, and
CD247, TRAJ17 and CD3D from group C.

In another preferred embodiment the biomarkers comprise:
HK3, MPO, GYG1 and SLC2A3 from group A, and
CD247, TRAJ17 and CD3D from group C.

In another preferred embodiment the biomarkers comprise:
HK3, MPO and SLC2A3 from group A, and
CD247, TRAJ17, CD3D and MAL from group C.

In another preferred embodiment the biomarkers comprise:
HK3, MPO and SLC2A3 from group A, and
CD247, TRAJ17, TRBV28 and MAL from group C.

In another preferred embodiment the biomarkers comprise:
HK3, MPO and SLC2A3 from group A, and
CD247, TRAJ17, TRBV28 and HLA-DMB from group C.

In another preferred embodiment the biomarkers comprise:
HK3, MPO, RETN, GPR84, STXBP2, GYG1, FPR2, and FFAR2 from group A, and:
MMP9, IL1R2, DYSF, PGLYRP1, BASP1, CKAP4 and FGR from group B.

In another preferred embodiment the biomarkers comprise:
HK3, MPO, RETN, ALPL, GYG1 and GRINA from group A, and
MMP9, IL1R2, DYSF, BASP1, CEBPD, CKAP4 and FGR from group B.

In another preferred embodiment the biomarkers comprise:
MMP9, IL1R2, DYSF, PGLYRP1, CEBPD and CKAP4 from group B, and
CD247, TRAJ17, TRBV28 and HLA-DMB from group C In another preferred embodiment the biomarkers comprise:
MMP9, IL1R2, DYSF, BASP1, CKAP4 and FGR from group B, and
CD247, TRAJ17, TRBV28 and HLA-DMB from group C.

In another preferred embodiment the biomarkers comprise:
MMP9, IL1R2, DYSF, CEBPD, CKAP4, and IL18R1 from group B, and
CD247, TRAJ17, TRBV28 and HLA-DMB from group C.

In another preferred embodiment the biomarkers comprise:
MMP9, IL1R2, DYSF, CEBPD, CKAP4 and FGR from group B, and
CD247, TRAJ17, CD3D and MAL from group C.

In another preferred embodiment the biomarkers comprise:
MMP9, IL1R2, DYSF, CEBPD, CKAP4 and FGR from group B, and
CD247, TRAJ17, TRBV28 and MAL from group C.

In another preferred embodiment the biomarkers comprise:
MMP9, IL1R2, DYSF, CEBPD, CKAP4 and FGR from group B, and
CD247, TRAJ17, TRBV28 and HLA-DMB from group C.

In some embodiments of the present invention it may be preferred that one or more of CEACAM1, DYSF, RNF24 and HK3 are not selected. Accordingly, variations upon the abovementioned combinations of biomarkers in which one or more of CEACAM1, DYSF, RNF24 and HK3 are excluded or not selected for use are explicitly contemplated as embodiments of the invention.

It will be apparent to the skilled person that the abovementioned combinations of biomarkers represent various minimal marker sets, and additional biomarkers, whether selected from groups A, B or C or not, can also be included.

The invention involves assessing changes in levels for biomarkers, and in preferred embodiments this change is typically differentially upwards for metabolic and innate immune pathway markers but differentially downwards for the adaptive immune pathway in subjects having sepsis.

For the avoidance of doubt, it should be noted that the present invention can be used for both initial diagnosis of sepsis and for ongoing monitoring of sepsis, e.g. response to treatment.

Throughout, biomarkers in the biological sample(s) from the subject are said to be differentially expressed and indicative of sepsis, where they are highly significantly up- or down-regulated. Depending on the individual biomarker, sepsis may be diagnosed in a biological sample by either an increase or decrease in expression level, scaled in relation to sample mean and sample variance, relative to those of uninfected controls or one or more reference values. Clearly, variation in the sensitivity of individual biomarkers, subject and samples mean that different levels of confidence are attached to each biomarker. Biomarkers of the invention are said to be highly significantly up- or down-regulated when after scaling of biomarker expression levels in relation to sample mean and sample variance, they exhibit a 2-fold change compared with uninfected controls or one or more reference values. Preferably biomarkers will exhibit a 3-fold change or more compared with the reference value. More preferably biomarkers of the invention will exhibit a 4-fold change or more compared with the reference value. That is to say, in the case of increased expression level (up-regulation relative to reference values), the biomarker level will be more than double that of the reference value. Preferably the biomarker level will be more than 3 times the level of the reference value. More preferably, the biomarker level will be more than 4 times the level of the reference value. Conversely, in the case of decreased expression level (down-regulation relative to reference values), the biomarker level will be less than half that of the reference value. Preferably the biomarker level will be less than one third of the level of the reference value. More preferably, the biomarker level will be less than one quarter of the level of the reference value.

Throughout the term "reference value" may refer to a pre-determined reference value, for instance specifying a confidence interval or threshold value for the diagnosis or prediction of the susceptibility of a subject to sepsis. Alternatively, the reference value may be derived from the expression level of a corresponding biomarker or biomarkers in a 'control' biological sample, for example a positive (infected) or negative (uninfected) control. Furthermore, the reference value may be an 'internal' standard or range of internal standards, for example a known concentration of a protein, transcript, label or compound. Alternatively, the reference value may be an internal technical control for the calibration of expression values or to validate the quality of the sample or measurement techniques. This may involve a measurement of one or several transcripts within the sample which are known to be constitutively expressed or expressed at a known level (e.g. an invariant level). Accordingly, it would be routine for the skilled person to apply these known techniques alone or in combination in order to quantify the level of biomarker in a sample relative to standards or other transcripts or proteins or in order to validate the quality of the biological sample, the assay or statistical analysis.

Preferably the subject is a human neonate. Typically the neonate is one which is suspected of having an infection. Neonate refers to an infant within the first 28 days after birth. In some embodiments the neonate may be within the first 14 days from birth, 7 days from birth, 3 days from birth, or within the first 48 hours from birth. However, it is anticipated that the biomarkers will also be suitable for diagnosing sepsis in infants from 28 to 40 days from birth, from 40 to 50 days from birth or alternatively from 50 days from birth to 1 year from birth. Similarly it is expected that biomarkers of the invention will be suitable for the diagnosis of sepsis in children from 1 to 2 years after birth, 1 to 3 years after birth or alternatively 1 to 4 years after birth. It is also expected that biomarkers of the invention will be suitable for the diagnosis of sepsis in neonates, infants and children of all ethnic genetic profiles and backgrounds. In certain embodiments, the neonate, infant or child is of Caucasian, Asian, African descent or genetic background. In a preferred embodiment the subject is a neonate, infant or child with a Caucasian genetic background. A neonate assessed in the present invention can be pre-term or full-term.

In preferred embodiments the methods of the invention are carried out in vitro, but it will be appreciated that the methods of the invention are also capable of being carried out in vivo.

The method may involve obtaining a sample of biological material from the subject, or it may be performed on a pre-obtained sample, e.g. one which has been obtained previously for other clinical purposes.

The present invention thus provides a method of diagnosing sepsis by analysing a biological sample obtained from a subject. Several different types of biological sample could be used, e.g. a body fluid sample or a tissue sample.

Typically the biological sample is selected from the group comprising: a blood sample; a saliva sample; a cerebrospinal fluid sample; and a stool sample.

In embodiments of the present invention wherein the patient sample is a body fluid sample, suitable examples of such a sample may be selected from the group comprising: a blood sample; a cerebrospinal fluid sample; a saliva sample, such as a buccal swab; a lung fluid sample; erythrocytes; leukocytes; and a stool sample.

Normally, the biological sample of the present invention will be a blood sample. Preferably the biological sample will be a whole blood sample.

The methods or devices of the present invention may make use of a range of biological samples taken from a subject to determine the expression level of a biomarker.

In certain embodiments the methods of the invention may further involve investigating physiological measurements selected from heart rate, temperature, respiratory rate and blood pressure or conducting a blood culture.

Suitably the biomarkers are selected from the group consisting of:
the biomarker protein; and nucleic acid molecule encoding the biomarker protein.

It is preferred that the biomarker is a nucleic acid molecule, and highly preferred that it is an mRNA molecule.

It is preferred that the levels of the biomarkers in the biological sample is investigated using specific binding partners.

Suitably the binding partners are selected from the group consisting of:
complementary nucleic acids; aptamers; antibodies or antibody fragments.

Suitable classes of binding partners for any given biomarker will be apparent to the skilled person.

Suitably the levels of the biomarkers in the biological sample are detected by direct assessment of binding between the target molecules and binding partners.

Suitably the levels of the biomarkers in the biological sample are detected using a reporter moiety attached to a binding partner.

Preferably the reporter moiety is selected from the group consisting of:
fluorophores; chromogenic substrates; and chromogenic enzymes.

Binding Partners

In certain embodiments of the invention, expression levels of the biomarkers in a biological sample may be investigated using binding partners which bind or hybridize specifically to the biomarkers or a fragment thereof. In relation to the present invention the term 'binding partners' may include any ligands, which are capable of binding specifically to the relevant biomarker and/or nucleotide or peptide variants thereof with high affinity. Said ligands include, but are not limited to nucleic acids (DNA or RNA), proteins, peptides, antibodies, synthetic affinity probes, carbohydrates, lipids, artificial molecules or small organic molecules such as drugs. In certain embodiments the binding partners may be selected from the group comprising: complementary nucleic acids; aptamers; antibodies or antibody fragments. In the case of detecting mRNAs, nucleic acids represent highly suitable binding partners.

In the context of the present invention, a binding partner specific to a biomarker should be taken as requiring that the binding partner should be capable of binding to at least one such biomarker in a manner that can be distinguished from non-specific binding to molecules that are not biomarkers. A suitable distinction may, for example, be based on distinguishable differences in the magnitude of such binding.

In preferred embodiments of the methods or devices of the invention, the biomarker is a nucleic acid, preferably an mRNA molecule, and the binding partner is selected from the group comprising;

complementary nucleic acids or aptamers.

Suitably the binding partner is a nucleic acid molecule (typically DNA, but it can be RNA) having a sequence which is complementary to the sequence the relevant mRNA or cDNA against which it is targeted. Such a nucleic acid is often referred to as a 'probe' (or a reporter or an oligo) and the complementary sequence to which it binds is often referred to as the 'target'. Probe-target hybridization is usually detected and quantified by detection of fluorophore-, silver-, or chemiluminescence-labeled targets to determine relative abundance of nucleic acid sequences in the target.

Probes can be from 25 to 1000 nucleotides in length. However, lengths of 30 to 100 nucleotides are preferred, and probes of around 50 nucleotides in length are commonly used with great success in complete transcriptome analysis.

While the determination of suitable probes can be difficult, e.g. in very complex arrays, there are many commercial sources of complete transcriptome arrays available, and it is routine to develop bespoke arrays to detect any given set of specific mRNAs using publically available sequence information. Commercial sources of microarrays for transciptome analysis include Illumina and Affymetrix.

In one embodiment that probe sequences will be those listed in Table 3. However, nucleotide probe sequences may be designed to any sequence region of the biomarker transcripts (accession numbers listed in Table 3) or a variant thereof. Nucleotide probe sequences, for example, may include, but are not limited to those listed in Table 3. The person skilled in the art will appreciate that equally effective probes can be designed to different regions of the transcript than those targeted by the probes listed in Table 3, and that the effectiveness of the particular probes chosen will vary, amongst other things, according to the platform used to measure transcript abundance and the hybridization conditions employed. It will therefore be appreciated that probes targeting different regions of the transcript may also be used in accordance with the present invention.

In other suitable embodiments of the invention, the biomarker may be a protein, and the binding partner is selected from the group comprising;

antibodies, antibody fragments or aptamers.

Polynucleotides encoding any of the specific binding partners of biomarkers of the invention recited above may be isolated and/or purified nucleic acid molecules and may be RNA or DNA molecules.

Throughout, the term "polynucleotide" as used herein refers to a deoxyribonucleotide or ribonucleotide polymer in single- or double-stranded form, or sense or anti-sense, and encompasses analogues of naturally occurring nucleotides that hybridize to nucleic acids in a manner similar to naturally occurring nucleotides. Such polynucleotides may be derived from Homo sapiens, or may be synthetic or may be derived from any other organism.

Commonly, polypeptide sequences and polynucleotides used as binding partners in the present invention may be isolated or purified. By "purified" is meant that they are substantially free from other cellular components or material, or culture medium. "Isolated" means that they may also be free of naturally occurring sequences which flank the native sequence, for example in the case of nucleic acid molecule, isolated may mean that it is free of 5' and 3' regulatory sequences.

In a preferred embodiment the nucleic acid is mRNA. There are numerous suitable techniques known in the art for the quantitative measurement of mRNA transcript levels in a given biological sample. These techniques include but are not limited to; "Northern" RNA blotting, Real Time Polymerase Chain Reaction (RTPCR), Quantitative Polymerase Chain Reaction (qPCR), digital PCR (dPCR), multiplex PCR, Reverse Transcription Quantitative Polymerase Chain Reaction (RT-qPCR), branched DNA signal amplification or by high-throughput analysis such as hybridization microarray, Next Generation Sequencing (NGS) or by direct mRNA quantification, for example by "Nanopore" sequencing. Alternatively, "tag based" technologies may be used, which include but are not limited to Serial Analysis of Gene Expression (SAGE). Commonly, the levels of biomarker mRNA transcript in a given biological sample may be determined by hybridization to specific complementary nucleotide probes on a hybridization microarray or "chip", by Bead Array Microarray technology or by RNA-Seq where sequence data is matched to a reference genome or reference sequences.

In a preferred embodiment, where the nucleic acid is mRNA, the present invention provides a method of diagnosing sepsis, wherein the levels of biomarker transcript(s) will be determined by PCR. Preferably mRNA transcript abundance will be determined by qPCR, dPCR or multiplex PCR. More preferably, transcript abundance will be determined by multiplex-PCR. Nucleotide primer sequences may be designed to any sequence region of the biomarker transcripts (accession numbers listed in Table 3) or a variant thereof. The person skilled in the art will appreciate that equally effective primers can be designed to different regions of the transcript or cDNA of biomarkers listed in Table 3, and that the effectiveness of the particular primers chosen will vary, amongst other things, according to the platform used to measure transcript abundance, the biological sample and the hybridization conditions employed. It will therefore be appreciated that primers targeting different regions of the transcript may also be used in accordance with the present invention. However, the person skilled in the art will recognise that in designing appropriate primer sequences to detect biomarker expression, it is required that the primer sequences be capable of binding selectively and specifically to the cDNA sequences of biomarkers corresponding to the nucleotide accession numbers listed in Table 3 or fragments or variants thereof.

Table 3 Probe sequences and accession numbers used in the current study. Annotation of the gene lists was obtained from the Clone/Gene ID Converter website (www.idconverter.bioinfo.cnio.es/IDconverter.php) and used Unigene Build Hs #210. For the 2 genes without Unigene ID's (TRAJ17 and TRBV28) Entrez Gene ID's are supplied (Entrez Gene entries were last updated on Feb. 4, 2014 (TRAJ17) and Jun. 2, 2014 (TRBV28) respectively).

TABLE 3

| Gene | Probe sequence | Accession (UniGene) | SEQ ID |
|---|---|---|---|
| ALPL | TCACACTCCTGGGCTCTGAACACACACGCCAGCTCCTCTCTGAAGCGACT | Hs.75431 | 1 |
| ANKRD22 | AGACTTTTGGTCTGTGGGCCATTTAACCTGGATGCCACCATTTTATGGGG | Hs.217484 | 2 |
| B4GALT5 | CCTCTTGTCAGAGATCCTCTACCACAGACATTAATAGCTGAGCAGGAGCC | Hs.370487 | 3 |
| BASP1 | CAGACAGAGCCCACTTAGCTTGTCCACATGGATCTCAATGCCAATCCTCC | Hs.201641 | 4 |
| C19orf59 | CTCCGTACATGTGGGTGTCGCCATGTGTGCCCTGTCACTATCTGTGGCTG | Hs.709539 | 5 |
| CD247 | ACTGCTGCGTCATTACAGGGCACAGGCCATGGATGGAAAACGCTCTCTGC | Hs.156445 | 6 |
| CD3D | GCTTTGGGAGTCTTCTGCTTTGCTGGACATGAGACTGGAAGGCTGTCTGG | Hs.504048 | 7 |
| CD7 | ACGGGAGGAGACCAGTCCCCCACCCAGCCGTACCAGAAATAAAGGCTTCT | Hs.36972 | 8 |
| CEACAM1 | GGTTTTCTAACCCTGACACGGACTGTGCATACTTTCCCTCATCCATGCTG | Hs.512682 | 9 |
| CEBPD | CGCCGGGTGCCCGCTGCAGTTTCTTGGGACATAGGAGCGCAAAGAAGCTA | Hs.440829 | 10 |
| CKAP4 | CTGCCTCCCTCATGGTGTGCGTGTCGTTCTCTTCCTGACGCATCTGTGAT | Hs.74368 | 11 |
| CSF3R | AAGCTCACAGTGCTGGAGGAGGATGAAAAGAAGCCGGTGCCCTGGGAGTC | Hs.524517 | 12 |
| DYSF | GGGCCATCATCCTCTTCATCATCCTCTTCATCCTGCTGCTGTTCCTGGCC | Hs.252180 | 13 |
| FCGR1A | GCAGCCTCCATGGGTCAGCGTGTTCCAAGAGGAAACCGTAACCTTGCACT | Hs.77424 | 14 |
| FFAR2 | GGGCTGGCTGTGGTGACGCTGCTCAATTTCCTGGTGTGCTTCGGACCTTA | Hs.248056 | 15 |
| FGR | AGGAAAAGTCTTGGCTGGACCCCTTTCCTGCTGGGTGGATGCAGTGGTCC | Hs.1422 | 16 |
| FPR2 | CCTACCCTAATGCCAGTTCCAGCTTCATCTACCCTTGAGTCATATTGAGG | Hs.99855 | 17 |
| GPR84 | GCATCAACCCTGTGCTCTATGCAGCCATGAACCGCCAATTCCGCCAAGCA | Hs.306199 | 18 |
| GRAP | GCTGGCCCAAGACCCTTAGAACCCTGAGTGCTGGCAAATCTCACTGCTCC | Hs.567416 | 19 |
| GRINA | GTGCCACCTCCTGTCTACTCATTGTTGCATGAGCCCTGTCTGCCAGCCCA | Hs.594634 | 20 |
| GYG1 | CTGCAGAGCCTGGTTCAAAATCAGTCACTCCCTTCAGAAGCAGACATGGC | Hs.477892 | 21 |
| HK3 | TCACCGCTGTTGCCTGCCGCCTTGCGCAGTTGACTCGTGTCTGAGGAAAC | Hs.411695 | 22 |
| HLA-DMB | CTCCTGGGGCTCTCAGTGTGCCATAGAGGACAGCAACTGGTGATTGTTTC | Hs.351279 | 23 |
| HP | GGCATTATGAAGGCAGCACAGTCCCCGAAAAGAAGACACCGAAGAGCCCT | Hs.513711// Hs.702099 | 24 |
| IFITM3 | GATCTTCCAGGCCTATGGATAGATCAGGAGGCATCACTGAGGCCAGGAGC | Hs.374650 | 25 |
| IL18R1 | GACTGTGAAACCGTCAGTTCGGAAGGCTGGTTAGAACATGTGGGAGCAAC | Hs.469521 | 26 |
| IL1R2 | GGGCATTGTGCTGGCCCCACTTTCACTGGCCTTCTTGGTTTTGGGGGGAA | Hs.25333 | 27 |
| IL1RN | GGCACTTGGAGACTTGTATGAAAGATGGCTGTGCCTCTGCCTGTCTCCCC | Hs.81134 | 28 |
| ITGAM | GGTTTCCTTCAGACAGATTCCAGGCGATGTGCAAGTGTATGCACGTGTGC | Hs.172631 | 29 |
| ITM2A | CCGCCTTCGTCGCAGAGACCTCTTGCTGGGTTTCAACAAACGTGCCATTG | Hs.694944// Hs.17109 | 30 |
| LCN2 | CCACATCGTCTTCCCTGTCCCAATCGACCAGTGTATCGACGGCTGAGTGC | Hs.204238 | 31 |
| LIME1 | GGGCTCCAGAGAAGGCCCGCGTCTAAATAAAGCGCCAGCGCAGGATGAAA | Hs.233220 | 32 |
| LOC729021 | CTCTCCGGGTGCAAAAGTTCCTCGAGTCAGCCTCTCCAGGCCCAGCTCCT | Hs.676685 | 33 |
| LRRN3 | GCTGCCTCTCTCCAGAAATGAACTGTGATGGTGGACACAGCTATGTGAGG | Hs.3781 | 34 |
| MAL | CTCACCCAACAGATCTTTCCAGAGGTCCATGGTGGAAGACGATAACCCTG | Hs.80395 | 35 |
| MMP9 | GCTTCTACTGGCGCGTGAGTTCCCGGAGTGAGTTGAACCAGGTGGACCAA | Hs.297413 | 36 |
| MPO | CCTGGGTTCCAATCCTGGCTCTGTGGCTTGCTAGCTATGTGACCTTGAGC | Hs.458272 | 37 |
| ORM1 | ACGTGGGAGGCCAAGAGCATTTCGCTCACTTGCTGATCCTCAGGGACACC | Hs.522356 | 38 |

TABLE 3-continued

| Gene | Probe sequence | Accession (UniGene) | SEQ ID |
|---|---|---|---|
| PFKFB3 | TGGGTGAGTTTCCCCCCTCCTTATTCTGTCCTGAGACCACGGGCAAAGCT | Hs.195471 | 39 |
| PGLYRP1 | GCGTACACTCTCTCCAGGCAACCAGCTCTACCACCTCATCCAGAATTGG | Hs.137583 | 40 |
| PRTN3 | CCTTCGTGATCTGGGGATGTGCCACCCGCCTTTTCCCTGACTTCTTCAC | Hs.928 | 41 |
| PSTPIP2 | TTTGCAAAGGGCCAAATTTCCCCAAACTGAACGGGCTCAGGAAATGTTC | Hs.567384 | 42 |
| RETN | TATTTAGGGCAATAAGCAGCATTGGCCTGGAGTGCCAGAGCGTCACCTC | Hs.283091 | 43 |
| RNF24 | ATCATTTCCCTCTCCTATGCACCAGTAAGGCCCGTCCAGAGCCCCAGCA | Hs.589884 | 44 |
| RPS29 | CCTCGTTGCACTGCTGAGAGCAAGATGGGTCACCAGCAGCTGTACTGGA | Hs.156367 | 45 |
| S100A12 | TCCAAGGCCTGGATGCTAATCAAGATGAACAGGTCGACTTTCAAGAATT | Hs.19413 | 46 |
| SLC2A3 | CTTTCTGGCTCCTCAAACAGTAGGTTGGCAGTAAGGCAGGGTCCCATTT | Hs.419240 | 47 |
| SPI1 | GAGTCTCAAGTCCGTATGTAAATCAGATCTCCCCTCTCACCCCTCCCACC | Hs.502511 | 48 |
| STXBP2 | GGCCCCCGGCTCATCGTGTATGTCATGGGCGGTGTGGCCATGTCAGAGAT | Hs.515104 | 49 |
| TNFAIP6 | CGATGATGTCCATGGCTTTGTGGGAAGATACTGTGGAGATGAGCTTCCAG | Hs.437322 | 50 |
| TRAJ17 | AGTAAACCCATATATCCAGAACCCTGACCCTGCCGTGTACCAGCTGAGAG | 28738 (Entrez Gene) | 51 |
| TRBV28 | AAACCCGTCACCCAGATCGTCAGCGCCGAGGCCTGGGGTAGAGCAGGTGA | 28559 (Entrez Gene) | 52 |

Many different techniques known in the art are suitable for detecting binding of the target sequence and for high-throughput screening and analysis of protein interactions. According to the present invention, appropriate techniques include (either independently or in combination), but are not limited to; co-immunoprecipitation, bimolecular fluorescence complementation (BiFC), dual expression recombinase based (DERB) single vector system, affinity electrophoresis, pull-down assays, label transfer, yeast two-hybrid screens, phage display, in vivo crosslinking, tandem affinity purification (TAP), ChIP assays, chemical cross-linking followed by high mass MALDI mass spectrometry, strep-protein interaction experiment (SPINE), quantitative immunoprecipitation combined with knock-down (QUICK), proximity ligation assay (PLA), bio-layer interferometry, dual polarisation interferometry (DPI), static light scattering (SLS), dynamic light scattering (DLS), surface plasmon resonance (SPR), fluorescence correlation spectroscopy, fluorescence resonance energy transfer (FRET), isothermal titration calorimetry (ITC), microscale thermophoresis (MST), chromatin immunoprecipitation assay, electrophoretic mobility shift assay, pull-down assay, microplate capture and detection assay, reporter assay, RNase protection assay, FISH/ISH co-localization, microarrays, microsphere arrays or silicon nanowire (SiNW)-based detection. Where biomarker protein levels are to be quantified, preferably the interactions between the binding partner and biomarker protein will be analysed using antibodies with a fluorescent reporter attached.

In certain embodiments of the invention, the expression level of a particular biomarker may be detected by direct assessment of binding of the biomarker to its binding partner. Suitable examples of such methods in accordance with this embodiment of the invention may utilise techniques such as electro-impedance spectroscopy (EIS) to directly assess binding of binding partners (e.g. antibodies) to target biomarkers (e.g. biomarker proteins).

In certain embodiments of the present invention the binding partner may be an antibody, or antibody fragment, and the detection of the target molecules utilises an immunological method. In certain embodiments of the methods or devices, the immunological method may be an enzyme-linked immunosorbent assay (ELISA) or utilise a lateral flow device.

A method of the invention may further comprise quantification of the amount of the target molecules indicative of expression of the biomarkers that is present in the patient sample. Suitable methods of the invention, in which the amount of the target molecule present has been quantified, and the volume of the patient sample is known, may further comprise determination of the concentration of the target molecules present in the patient sample which may be used as the basis of a qualitative assessment of the patient's condition, which may, in turn, be used to suggest a suitable course of treatment for the patient.

Reporter Moieties

In preferred embodiments of the present invention the expression levels of the protein in a biological sample may be determined. In some instances, it may be possible to directly determine expression, e.g. as with GFP or by enzymatic action of the protein of interest (P01) to generate a detectable optical signal. However, in some instances it may be chosen to determine physical expression, e.g. by antibody probing, and rely on separate test to verify that physical expression is accompanied by the required function.

In preferred embodiments of the invention, the expression levels of a particular biomarker will be detectable in a biological sample by a high-throughput screening method, for example, relying on detection of an optical signal, for instance using reporter moieties. For this purpose, it may be necessary for the specific binding partner to incorporate a tag, or be labelled with a removable tag, which permits detection of expression. Such a tag may be, for example, a fluorescence reporter molecule translationally-fused to the protein of interest (POI), e.g. Green Fluorescent Protein (GFP), Yellow Fluorescent Protein (YFP), Red Fluorescent Protein (RFP), Cyan Fluorescent Protein (CFP) or mCherry. Such a tag may provide a suitable marker for visualisation of biomarker expression since its expression can be simply and directly assayed by fluorescence measurement in vitro or on an array.

Alternatively, it may be an enzyme which can be used to generate an optical signal. Tags used for detection of expression may also be antigen peptide tags. Similarly, reporter moieties may be selected from the group consisting of fluorophores; chromogenic substrates; and chromogenic enzymes. Other kinds of label may be used to mark a nucleic acid binding partner including organic dye molecules, radiolabels and spin labels which may be small molecules.

Preferably, the levels of a biomarker or several biomarkers will be quantified by measuring the specific hybridization of a complementary nucleotide probe to the biomarker of interest under high-stringency or very high-stringency conditions.

Preferably, probe-biomarker hybridization will be detected and quantified by detection of fluorophore-, silver-, or chemiluminescence-labelled probes to determine relative abundance of biomarker nucleic acid sequences in the sample. Alternatively, levels of biomarker mRNA transcript abundance can be determined directly by RNA sequencing or nanopore sequencing technologies.

The methods or devices of the invention may make use of molecules selected from the group consisting of: the biomarker protein; and nucleic acid encoding the biomarker protein.

Nucleotides and Hybridization Conditions

Throughout, the term "polynucleotide" as used herein refers to a deoxyribonucleotide or ribonucleotide polymer in single- or double-stranded form, or sense or anti-sense, and encompasses analogues of naturally occurring nucleotides that hybridize to nucleic acids in a manner similar to naturally occurring nucleotides.

Exemplary probe sequences are provided in Table 3, although it will be appreciated that minor variations in these sequences may work. The person skilled in the art would regard it as routine to design nucleotide probe sequences may be designed to any sequence region of the biomarker transcripts (accession numbers listed in Table 3) or a variant thereof. This is also the case with nucleotide primers used where detection of expression levels is determined by PCR-based technology. Nucleotide probe sequences, for example, may include, but are not limited to those listed in Table 3. The person skilled in the art will appreciate that equally effective (and in some cases more beneficial) probes can be designed to different regions of the transcript than those targeted by the probes listed in Table 3, and that the effectiveness of the particular probes chosen will vary, amongst other things, according to the platform used to measure transcript abundance and the hybridization conditions employed. It will therefore be appreciated that probes targeting different regions of the transcript may also be used in accordance with the present invention.

Of course the person skilled in the art will recognise that in designing appropriate probe sequences to detect biomarker expression, it is required that the probe sequences be capable of binding selectively and specifically to the transcripts or cDNA sequences of biomarkers corresponding to the nucleotide accession numbers listed in Table 3 or fragments or variants thereof. The probe sequence will therefore be hybridizable to that nucleotide sequence, preferably under stringent conditions, more preferably very high stringency conditions. The term "stringent conditions" may be understood to describe a set of conditions for hybridization and washing and a variety of stringent hybridization conditions will be familiar to the skilled reader. Hybridization of a nucleic acid molecule occurs when two complementary nucleic acid molecules undergo an amount of hydrogen bonding to each other known as Watson-Crick base pairing. The stringency of hybridization can vary according to the environmental (i.e. chemical/physical/biological) conditions surrounding the nucleic acids, temperature, the nature of the hybridization method, and the composition and length of the nucleic acid molecules used. Calculations regarding hybridization conditions required for attaining particular degrees of stringency are discussed in Sambrook et al. (2001, *Molecular Cloning: A Laboratory Manual, Cold Spring Harbor Laboratory Press, Cold Spring Harbor, NY*); and Tijssen (1993, *Laboratory Techniques in Biochemistry and Molecular Biology—Hybridization with Nucleic Acid Probes Part I, Chapter* 2, Elsevier, N.Y.). The Tm is the temperature at which 50% of a given strand of a nucleic acid molecule is hybridized to its complementary strand.

In any of the references herein to hybridization conditions, the following are exemplary and not limiting:
Very High Stringency (Allows Sequences that Share at Least 90% Identity to Hybridize)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Allows Sequences that Share at Least 80% Identity to Hybridize)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Allows Sequences that Share at Least 50% Identity to Hybridize)
Hybridization: 6×SSC at RT to 55° C. for 16-20 hours
Wash at least twice: 2×-3×SSC at RT to 55° C. for 20-30 minutes each.

Diagnostic Devices and Kits

In a further embodiment, the present invention provides a device for use in the diagnosis of sepsis, the device comprising:

a) a loading area for receipt of a biological sample;
b) binding partners specific for target molecules indicative of the expression of two or more biomarkers listed in Table 1, wherein at least one biomarker is selected from wherein the biomarkers are selected from any of groups A, B or C; and
c) detection means to detect the levels of said biomarker present in the sample.

Suitably the device comprises specific binding partners to the biomarkers being amplified. A variety of suitable PCR amplification-based technologies are well known in the art.

The binding partners are preferably nucleic acid primers adapted to bind specifically to the cDNA transcripts of biomarkers, as discussed above.

The detection means suitably comprises means to detect a signal from a reporter moiety, e.g. a reporter moiety as discussed above.

The device is adapted to detect and quantify the levels of said biomarkers present in the biological sample.

In a further embodiment, the present invention provides a kit of parts for selectively determining, in a sample, the levels of two or more biomarkers for sepsis, wherein the kit comprises:
- a) at least one binding partner that selectively binds to the biomarker(s) selected from group A of Table 1 or a fragment thereof;
- b) at least one binding partner that selectively binds to the biomarker(s) selected from group B and/or group C of Table 1, or a fragment thereof;
- c) a positive control for the detection of said biomarkers;
- d) at least one binding partner that selectively binds to a nucleic acid which operates as an internal control; and
- e) optionally an internal standard.

PCR applications are routine in the art and the skilled person will be able to select appropriate polymerases, buffers, reporter moieties and reaction conditions.

The binding partners are preferably nucleic acid primers adapted to bind specifically to the cDNA transcripts of biomarkers, as discussed above. Preferably primers will be provided that specifically target the following biomarkers:
SLC2A3 and LRRN3; SLC2A3, GPR84 and LRRN3; SLC2A3, GPR84, RETN, and LRRN3; SLC2A3, LRRN3 and TRAJ17; SLC2A3, GPR84, LRRN3 and TRAJ17; SLC2A3, GPR84, RETN, LRRN3 and TRAJ17; SLC2A3, LRRN3, TRAJ17 and CD3D; SLC2A3, GPR84, LRRN3, TRAJ17 and CD3D; SLC2A3, GPR84, RETN, LRRN3, TRAJ17 and CD3D; LRRN3 and BASP1; LRRN3, TRAJ17 and BASP1; LRRN3, TRAJ17, CD3D and BASP1; LRRN3, BASP1 and CKAP4; LRRN3, TRAJ17, BASP1 and CKAP4; LRRN3, TRAJ17, CD3D, BASP1 and CKAP4; LRRN3, BASP1, CKAP4 and C19orf59; LRRN3, TRAJ17, BASP1, CKAP4 and C19orf59; LRRN3, TRAJ17, CD3D, BASP1, CKAP4 and C19orf59; SLC2A3 and BASP1; SLC2A3, GPR84 and BASP1; SLC2A3, GPR84, RETN and BASP1; SLC2A3, BASP1 and CKAP4; SLC2A3, GPR84, BASP1 and CKAP4; SLC2A3, GPR84, RETN, BASP1 and CKAP4; SLC2A3, BASP1, CKAP4 and C19orf59; SLC2A3, GPR84, BASP1, CKAP4 and C19orf59; SLC2A3, GPR84, RETN, BASP1, CKAP4 and C19orf59.

BRIEF DESCRIPTION OF THE FIGURES

Embodiments of the invention are further described hereinafter and with reference to specific examples and drawings in which:

FIG. 1 shows demographics of samples used, microorganisms identified from infected groups and reasons for blood sampling in control groups. A. Demographics of samples used. Patient sample details are shown displaying the demographics of the population studied. B. Microorganisms isolated from infected groups. Organisms detected for each infected infant are shown—these samples were taken at, or within 6 hours of, the time of clinical suspicion of infection. C. Reasons for blood sampling in control group. The reasons for clinical blood sampling in the control group are shown—all of the screening tests in these infants were normal.

DETAILED DESCRIPTION

EXAMPLE 1

Study Design, Power Calculations and Participants

The study was conducted in the Neonatal Unit, Royal Infirmary of Edinburgh and the Division of Pathway Medicine, University of Edinburgh. Infants having blood cultures taken to investigate suspected infection (FIG. 1) and "well" control infants having blood taken for other clinical reasons (FIG. 1) were studied. Five infants had samples included from more than one episode of infection. After parent consent, we obtained blood samples at the time of first clinical signs of suspected infection with an additional 0.5-1 ml of whole blood for expression profiling collected alongside the "gold-standard" microbiological blood culture. Samples taken from patients with suspected clinical infection that proved to have microbiological evidence of infection from a usually sterile body site were identified and formed the infected group. Full clinical assessment for early and late symptoms and signs of sepsis followed criteria for neonatal sepsis (FIG. 1) with the blood culture test used as the 'gold standard' for diagnosis of sepsis. For patient samples with coagulase negative staphylococcus full clinical assessment was conducted independently by two clinicians (CLS and BJS/JO) and clinical evidence supporting or refuting inclusion was reviewed. The neonatal unit uses the definitions of the Vermont Oxford Network for infection surveillance (Horbar et al., *Pediatrics* 129, 1019-1026 (2012)) and associated clinical deterioration, repeat isolates and deranged blood counts were also examined. Samples were only included as positive if both clinicians agreed that infection was present. This was conducted blind to the results of any RNA expression profile data. For power calculations samples were obtained from 30 infants at 9 months of age, prior to vaccination.

Figure 2:
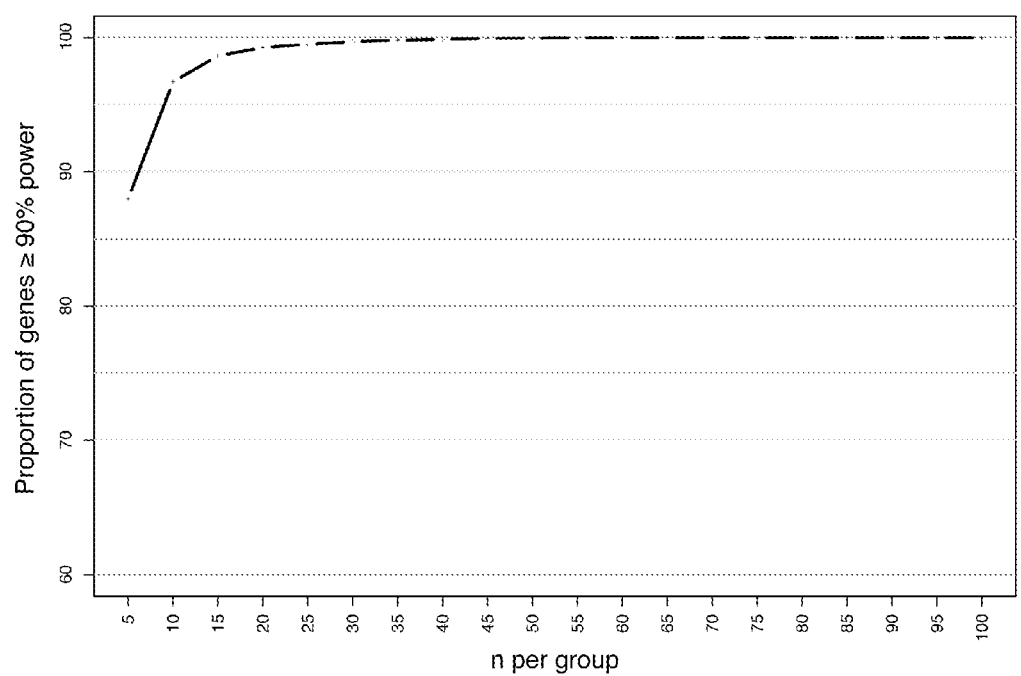
FIG. 2 shows power calculations for use of infant whole blood RNA samples in microarray expression profiling. Sample size (X-axis) to obtain 90% power for a given proportion of genes on array (Y-axis), at $p \leq 0.01$. Microarray expression profile data from a set of 30 control pre-vaccinated 9 month old Gambian infant samples was used to perform the power calculations.

For RNA isolation blood was immediately injected into a PAXgene™ blood RNA tube. Frozen samples were subjected to RNA extraction and microarray analysis performed. Prior to embarking on this study we performed a power calculation using the Illumina® chip platform, on an independent set of 30 infant samples (FIG. 2). This shows that the study design has 90% power to detect a 2-fold change in expression with an α of 1% (FDR-corrected), for more than 99% of 35,177 gene probes present on the array. RNA was extracted using a protocol validated for use in small volume neonatal blood samples (Smith et al., *Analyst* 132, 1200-1209 (2007)).

EXAMPLE 2

Statistical Analysis

High quality RNA from infected and control infants was hybridized onto ILLUMINA® Human Whole-Genome Expression BeadChip HT12v3 microarrays comprising 48,802 features (human gene probes). Microarray quality analysis used the arrayQualityMetrics package in Bioconductor (Kauffmann et al., *Bioinformatics* 25, 415-416 (2009)) and a gender check was performed using Y-chromosome specific loci. Using the 'lumi' Bioconductor package raw data from 63 samples was transformed using a variance stabilising transformation prior to robust spline normalisation to remove systematic between-sample variation. Microarray features that were not detected, using detectionCall on any of the arrays were removed from analysis and the remaining 23,342 features were used for subsequent statistical analysis. Data were statistically examined to assess gestational age as a confounding factor. Within each sample group (control, infected), samples were age-classified into bins based on the 33% and 66% corrected gestational age quantile values, yielding three age-groupings. Comparison of normalised data between groups utilised linear modeling of the $\log_2$ scale expression values between groups and subsequent empirical Bayesian approaches to moderate the test statistic by pooling variance information from multiple genes. This included vertical p-value adjustment for multiple testing (Benjamini-Hochberg) to control for false discovery rate using the Bioconductor package 'limma' (Shanley et al., *Mol Med* 13, 495-508 (2007); Smyth, *Bioinformatics and Computational Biology Solutions Using R and Bioconductor* (Ed Carey V J Gentleman R, Huber W, Irizarry R A, Dudoit S.) Ch. 23, (Springer, 2005)). Statistically significant differentially expressed genes were examined further: heat maps and line graphs with hierarchical clustering by Euclidean distance were examined using Partek Genomics Suite v6.5, and visualisation of networks of genes looking for patient specific responses using BioLayout Express 3D (Theocharidis et al., *Nature protocols* 4, 1535-1550 (2009)). Unsupervised clustering of patient samples was carried out: probes with coefficient of variation (CV) greater than 0.1 were used (10,206) and hierarchical clustering was based on Euclidean distance.

Figure 3:
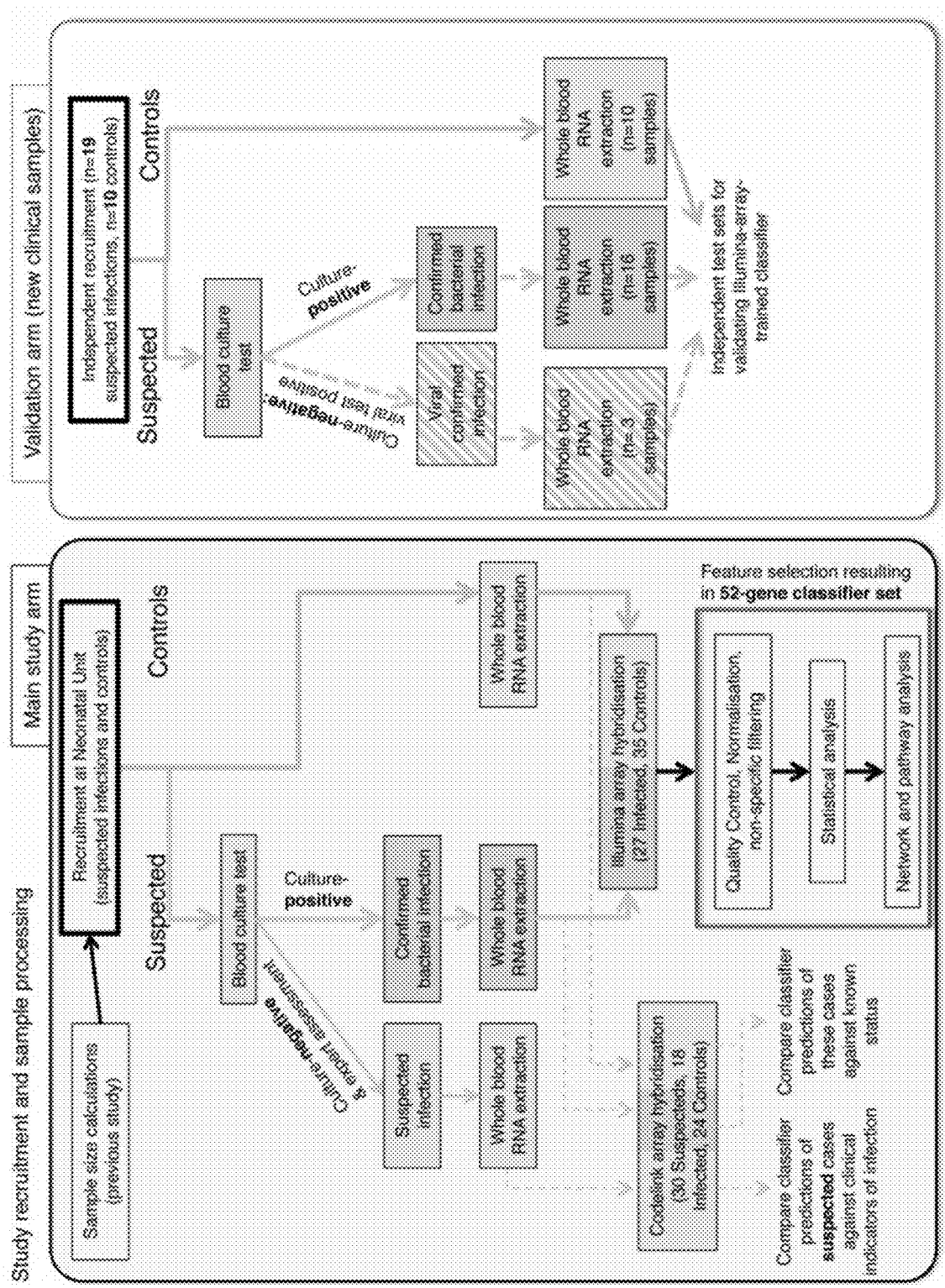
FIG. 3 shows study recruitment and sample processing. The flow diagram depicts process of neonatal subject recruitment, sample processing and microarray hybridization. Boxes and arrows are colour-coded as follows. Healthy (presenting for other clinical reasons than suspected infection) control neonate samples=light grey; neonate samples of suspected but unconfirmed infections=light grey; neonate samples with blood-culture test confirmed infection=dark grey; neonate samples with blood-culture negative test but confirmed viral infection=striped.

For purposes of classification, we refer to the 62 ILLUMINA®-hybridized samples with the selected subset of 52 genes as "training set". We employ multiple types of classification test sets, which are defined as follows (FIG. 3). In addition to the ILLUMINA® microarray analysis we examined a subset of 42 of these samples (18 infected, 24 controls) using CODELINK™ Whole Human Genome arrays, referred to as "platform test set". Subsequently, the classifier was applied to a further 26 new and independent samples (16 bacterially infected samples from 15 infants and ten control samples) which were run on CODELINK™ (seven infected, three control), AFFYMETRIX® HG-U133 (two infected, three control) or AFFYMETRIX® Human Genome U219 (nine infected, six control) arrays. These are collectively referred to as "validation test set". We also assess the performance of our classifier on 30 independent samples with suspected but initially unconfirmed infection (CODELINK™ arrays) and refer to this as "suspected infected test set".

Use of the term "classifier" refers to the classification algorithm and its trained state based on our set of 52 biomarkers. In discussion of the set of 52 biomarkers themselves we refer to these as "classifier gene set" or "52-gene classifier". Prior to training and testing the classifier algorithms, the original $\log_2$ expression values for the 52-gene set were scaled to mean=0 and standard deviation=1 (i.e. z-transformation per sample).

Microarray data has been deposited in Gene Expression Omnibus with accession code GSE25504, (www.ncbi.nlm.nih.gov).

EXAMPLE 3

Network, Pathway and Classifier Analysis

Computational network-based approaches were used to examine relationships in the data using correlation of gene expression and biological relationships. Ingenuity Pathways Analysis (IPA-www.ingenuity.com), DAVID (Huang et al., *Nat Protoc* 4, 44-57 (2009)) and a manually curated dataset of human gene interactions in InnateDB (www.innatedb.com) (Lynn et al., *Mol Syst Biol* 4, 218 (2008)) were used to examine biological network relationships and association with known pathways e.g. KEGG (Ogata, H. et al., *Nucleic Acids Res* 27, 29-34 (1999)). The InnateDB network was analyzed using Cytoscape 2.6.3 (Shannon, P. et al., *Genome Research* 2498-2504 (2003)) and the cytoHubba plugin (Lin et al., *Nucleic Acids Res* 36, W438-443 (2008)) to investigate a variety of properties of a network including the identification of network hubs and bottlenecks which may represent the key regulatory nodes in the network. The network was also analyzed to identify 'active sub-networks' using the jActiveModules (Ideker et al., *Bioinformatics* 18 Suppl 1, S233-240 (2002)) plugin to identify densely-connected differentially expressed sub-networks. Cellular localisations of network components were visualised using and the Cerebral v.2 (Barsky et al., *Bioinformatics* 23, 1040-1042 (2007)) plugin. The contribution of specific blood cell subsets was examined by categorising responses according to cell type using cell specific gene markers described by Abbas and colleagues (Abbas et al., *PLoS One* 4, e6098 (2009)). Pathway analyses were carried out stepwise using a pathway-biology approach, becoming more focused until a defined sub-network of 52 differentially expressed genes was identified. The selected genes had adjusted p values of $\leq 10^{-5}$, fold changes of $\geq 4$ and were highly connected in terms of biological pathways and networks. These 52 genes were then assessed for prediction precision in a leave-one-out cross validation error modelling using four different classification methods: Random Forests, Support Vector Machines, K Nearest Neighbour and ROC-based classification. Leave-one-out cross validation was repeated 100 times for each set of selected genes following a random ordering of the data at each replication to minimise variability of the error estimates. For independent technical validation of RNA expression levels of the classifier gene set outside the neonatal sample set used for feature selection, a subset of samples run on CODELINK™ Human Whole Genome Bioarrays was examined (platform test set). The subset was chosen only by virtue of being previously run on CODELINK™. ROC classification (Lauss et al., *BMC Cancer* 10, 532 (2010)) was used to repeat the internal cross-validation on this subset using the markers that were present on both arrays and then using the trained classifier to predict the CODELINK™ samples. For further validation, a new sample set of 16 bacterially infected and 10 control samples (not previously used for feature selection or other analyses, but obtained in the same study setting with the same sample collection protocol) run on CODELINK™, AFFYMETRIX® Human Genome HG-U 133 Plus 2.0 or AFFYMETRIX® Human Genome U219 arrays had the ROC-based classifier applied (validation test set). All classification analyses were performed with R (www.R-project.org, (2013)), classification error in relation to gene set size was performed with the R package 'optBiomarker' (Khondoker et al., *Journal of Bioinformatics and Computational Biology* 08, 945-965 (2010) and ROC based classification uses the R package 'rocc' (Lauss et al., *BMC Cancer* 10, 532 (2010)).

Study Approval

Written informed consent was obtained from parents of all enrolled infants in accordance with approval granted by the Lothian Research Ethics Committee for blood samples for RNA isolation obtained at the first time of clinical signs of suspected sepsis (Reference 05/s1103/3). Samples used in power calculations were collected with the approval of the Gambia Government/MRC Laboratories Joint Ethics Committee and London School of Tropical Medicine ethics committee (Reference SCC1085, L2008.63).

EXAMPLE 4

Patient Recruitment, Sample Analysis Workflow and Study Design

Figure 4:
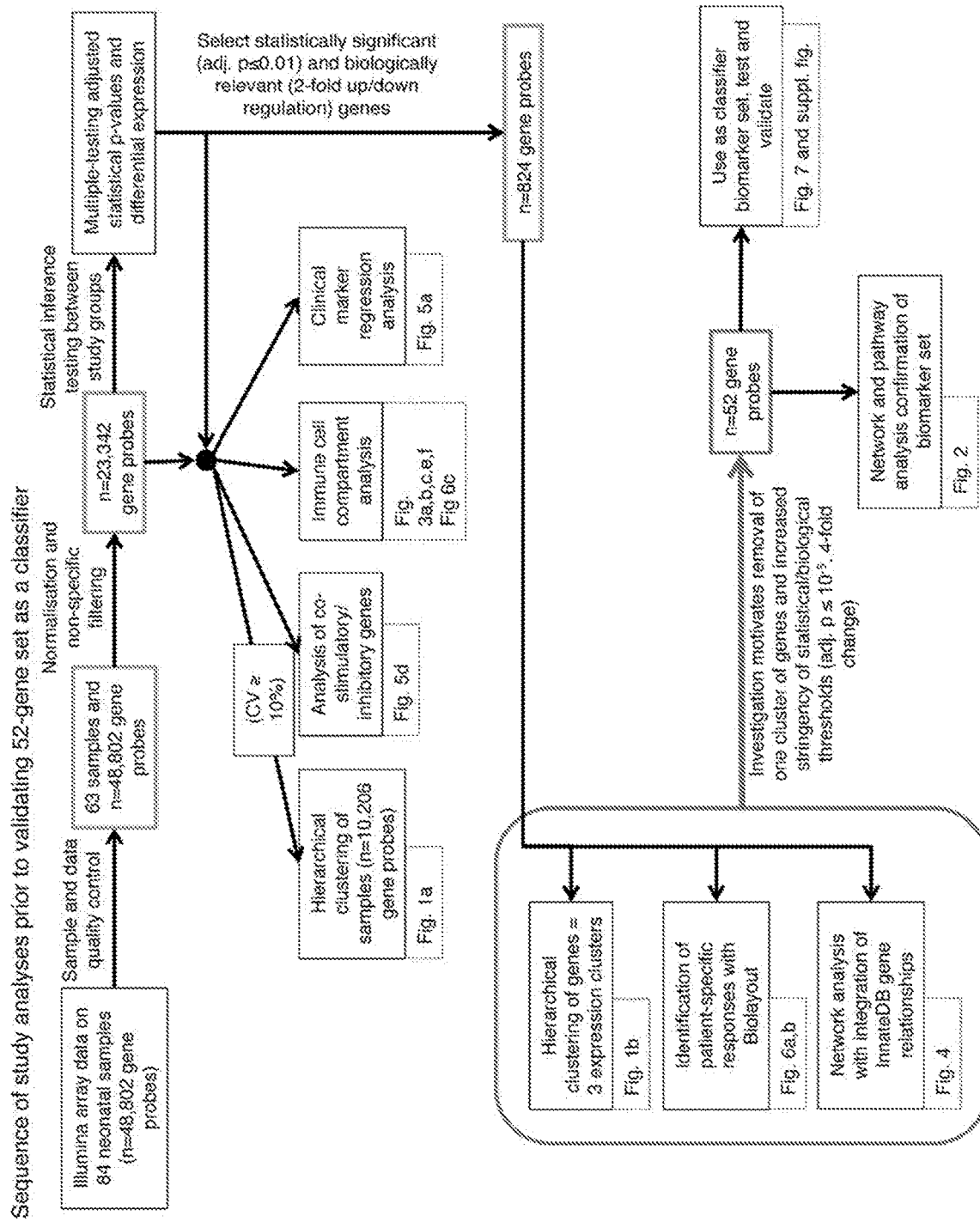
FIG. 4 shows a sequence of study analyses prior to validating 52-gene set as a classifier. This flow diagram identifies the sequence of analyses carried out on Illumina microarray data. Dotted boxes indicate manuscript figures that are the primary representation of a given process or analysis. The red box indicates that the analyses within are used in combination to inform a subsequent result.
Figure 5:
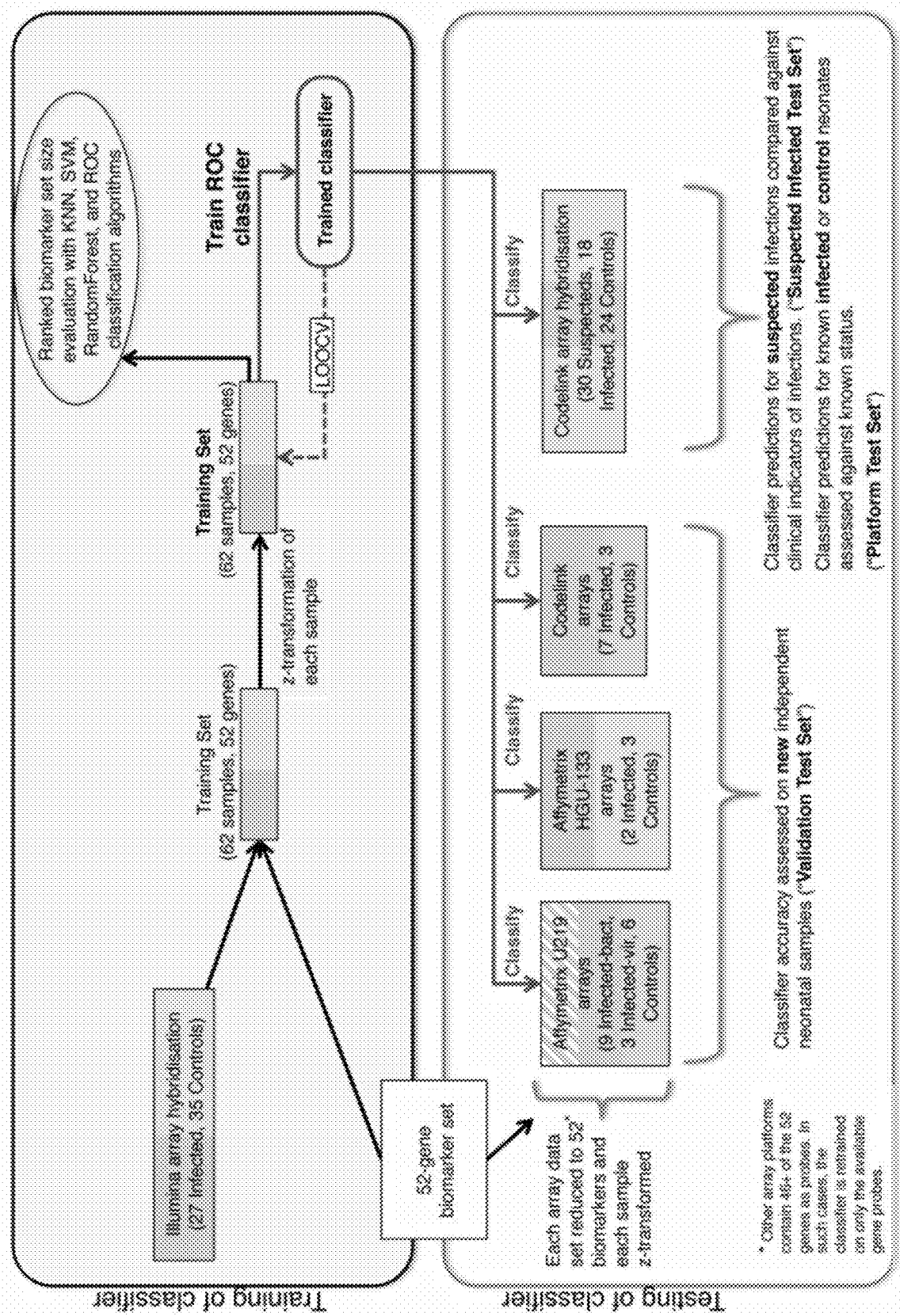
FIG. 5 shows training and testing of 52-gene classifier of sepsis in neonates. This diagram details the stages comprising training and testing of the ROC-based classifier. Top box represents processes in the training of the classifier; bottom box represents processes in the testing of the classifier on various types of test sets. LOOCV stands for Leave-One-Out-Cross-Validation, which is the iterative process in which a single sample of the training set is predicted based on the classifier trained on all remaining samples. Black arrows are data processing steps; red arrows indicate classifier training and prediction steps. Sample colour coding: healthy (presenting for other clinical reasons than suspected infection) control neonate samples=light grey; neonate samples of suspected but unconfirmed infections=light grey; neonate samples with blood-culture test confirmed infection=dark grey; neonate samples with blood-culture negative test but confirmed viral infection=striped.

The patient demographics, microbial organisms isolated and reasons for blood sampling in controls for all patient sets are shown in FIG. 1. All samples were processed for genome-wide transcriptional analysis using microarrays. On the basis of power calculations (FIG. 2) sample size of approximately 25 for each group has ≥90% power to detect two-fold changes in expression level of 99% of probes on the microarray. A schematic of patient recruitment and sample processing workflow for the 285 samples processed for the main study and validation arm is shown in FIG. 3. For the computational and statistical pathway biology aspects of this study a summary of data analysis workflow and associated figures is provided in FIG. 4. The main study arm primarily used RNA profiling data using the Illumina HT12 platform from 27 patient samples with a confirmed blood culture positive test for sepsis (bacterial infected cases), one cytomegalovirus (CMV) infected case and 35 matched controls. Samples from these cases (not including the viral infected case) are referred to as the "training set" in this study. For assessing reproducibility with a different assay platform we examined a subset of 42 of these samples using the CodeLink gene expression platform (comprising 18 bacterial infected and 24 control samples) named in this study as "platform test set". Subsequently, for independent clinical evaluation, the 52-gene set classifier was applied to a further 29 new and independent samples (comprising 16 bacterial infected, three viral infected and ten control samples) named in this study as "validation test set". Finally, a set of 30 new samples collected upon suspicion of infection with negative blood culture were analysed, named in this study as "suspected infected test set". A detailed summary of the workflow for the training and testing of the 52-gene set classifier of sepsis in neonates is shown in FIG. 5.

EXAMPLE 5

A Vigorous Systemic Host-RNA Network Perturbation in Neonatal Infection

Figure 6:
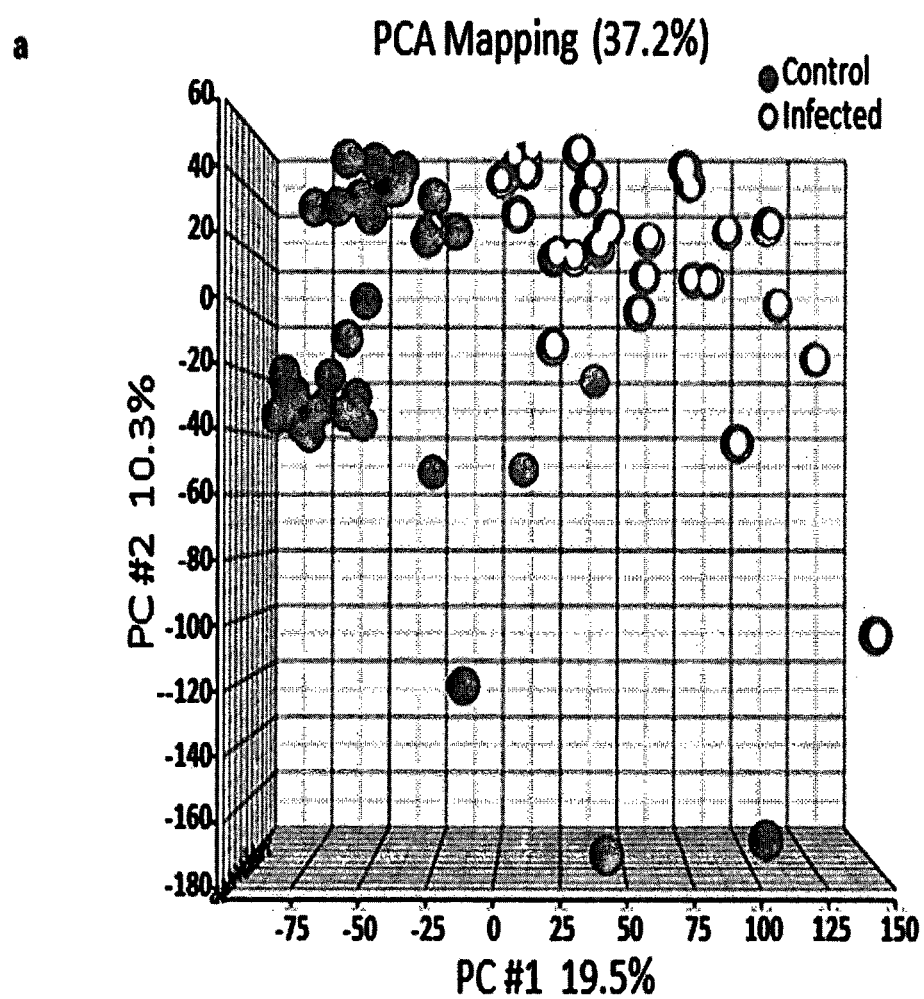
FIG. 6 shows a principal components analysis of infected and control patient samples before and after statistical filtering of data. (a) Infected (hollow circles) and control (circles) patients are largely separated into two distinct groups in an unsupervised approach by the 3 major components accounting for 37.6% of variation in the data. (b) After statistical filtering (adj.$p \leq 0.01$, fold change $\geq 2$) patient samples fall into 2 major and one minor groups represented by 3 major components accounting for 87.6% of variation. The minor group comprising 6 control samples and 1 infected sample (the single viral infection sample in the dataset) stand apart from the major infected and control groups. This group of patients is also identified by hierarchical cluster analysis in FIG. 1b.
Figure 6:
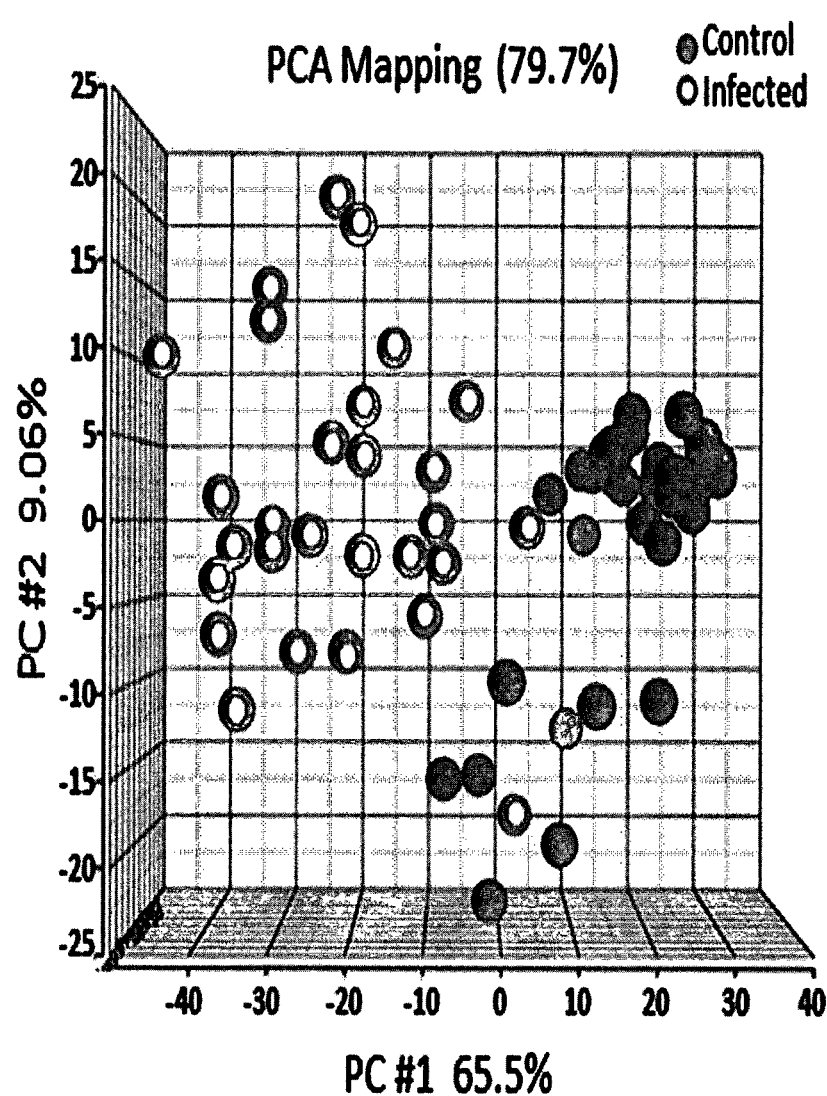
Figure 10:
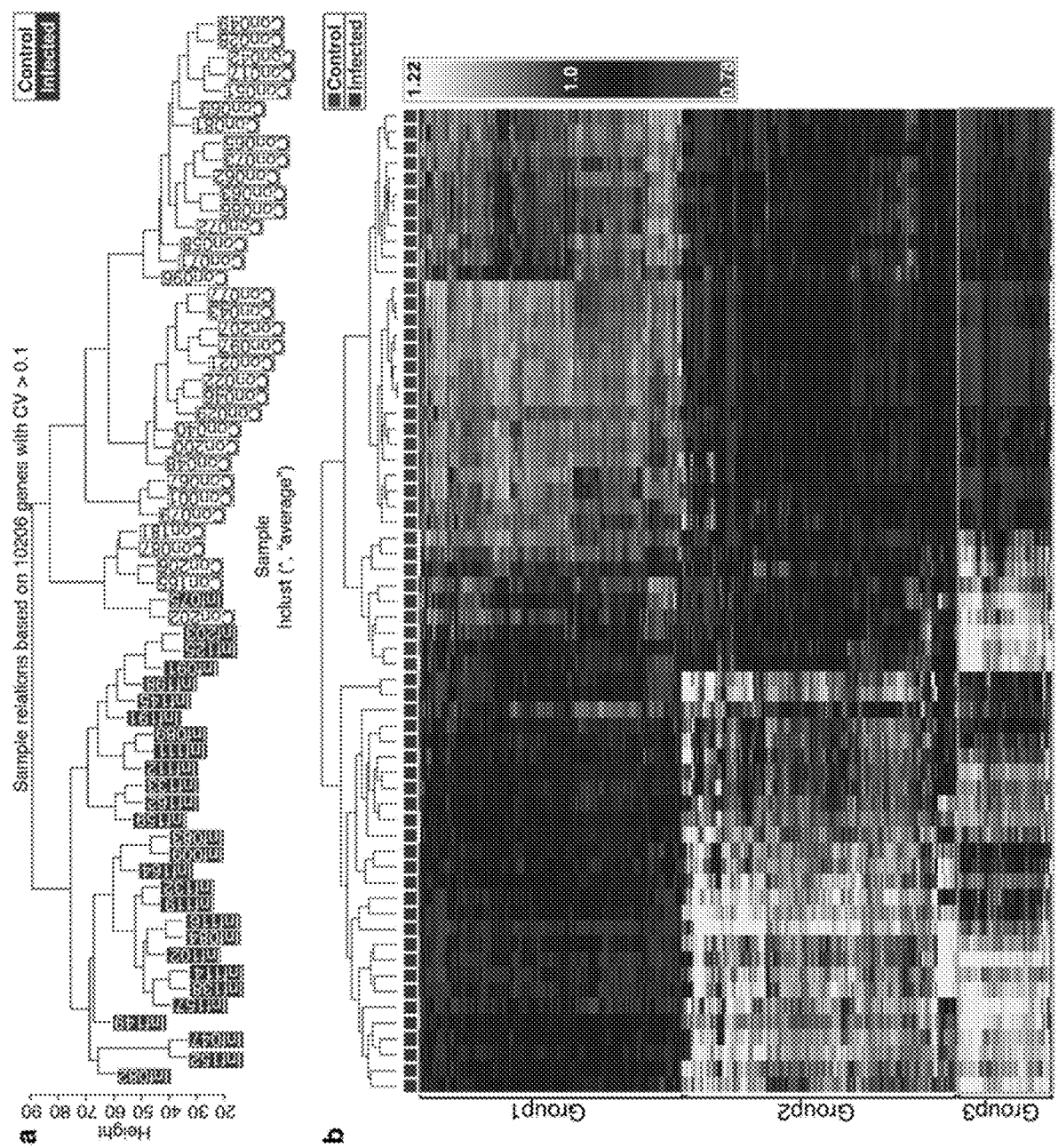
FIG. 10 shows the hierarchical clustering of infected and control patient samples. (a) Results from unsupervised analysis of normalised data prior to statistical testing. At this stage the condition of whether the samples were infected or not had not been included in the analysis. Control—not-filled, infected—filled. Panel (b) is a heat map showing hierarchical clustering of infant samples based on the 824 probes that were statistically differentially expressed between infected and control groups (adj.p ≤1.01, absolute fold change ≥2). Hierarchical clustering was based on Euclidean distance. Three clusters of genes are labelled (1-3). Group 3 genes (highlighted with box) were excluded from the further analysis for derivation of a classifier of neonatal bacterial infection because of no clear separation between infected and controls. Control—blue, infected—red.

We first sought to assess the magnitude and extent of variability of response to infection using the training set and the one virally infected case. In these analyses, 23,342 array probes gave detectable signal above the limit of detection for one or more samples. Of these 10,206 array probes showed 10% or greater coefficient of variation (CV>0.1) across all 63 samples, indicating a large magnitude and breadth of changes. A principal components analysis of patient samples based on these 10,206 probes and agglomerative unsupervised clustering of unfiltered, normalised data was undertaken. The results of these analyses revealed a clear separation into control and infected groups, showing a dramatic alteration in RNA expression between infected and control samples (FIG. 6 and FIG. 10). The single exception to this grouping was the only virally (CMV) infected sample in this set and was excluded from later analyses.

Figure 9:
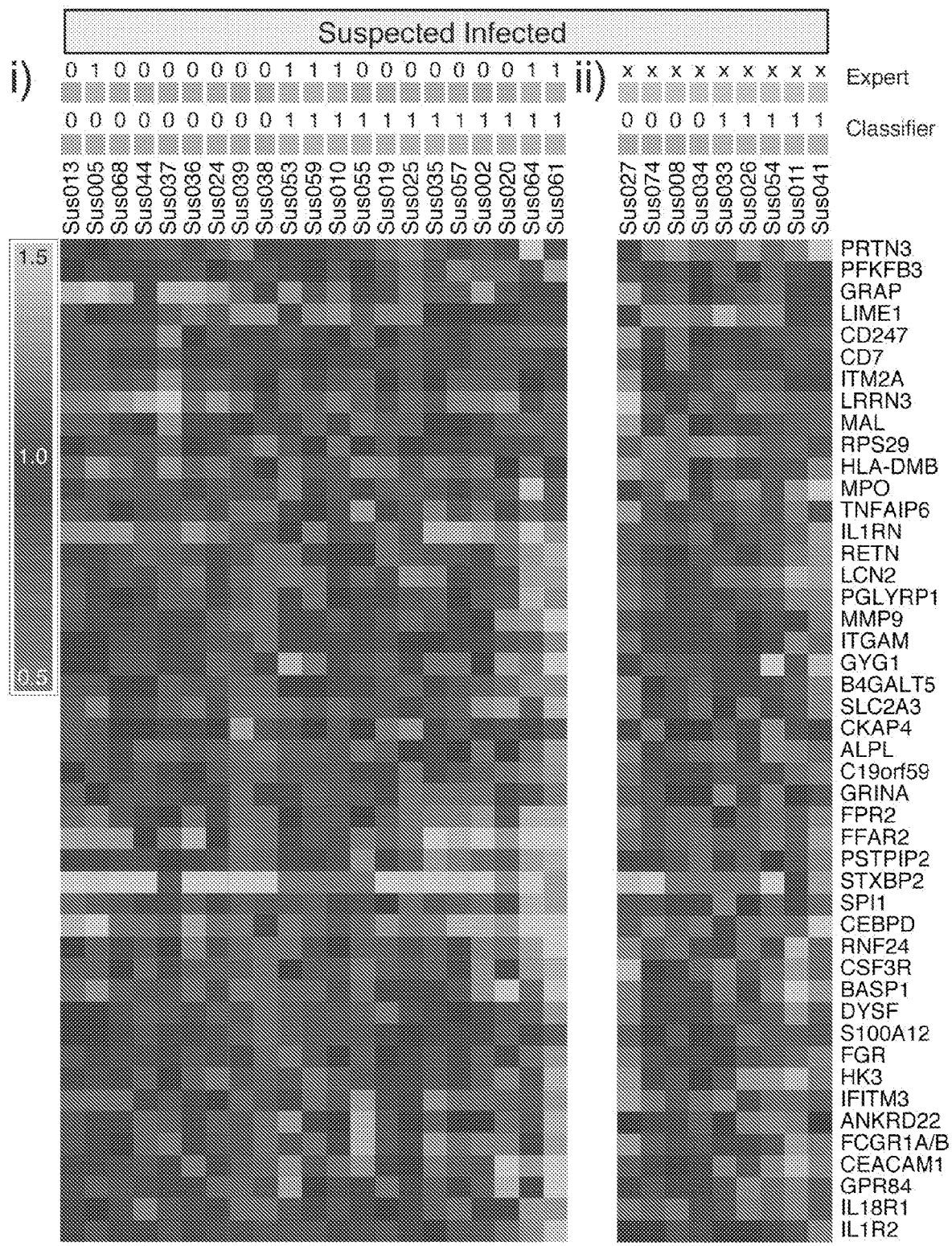
FIG. 9 is a heat map showing 30 infant samples of suspected infection based on the 46 probes that were in common between the classifier gene set and the CodeLink platform.

The large scale and clear demarcation of this response is further underscored after statistical testing between infected and control groups, revealing 8,242 significantly differentially expressed probes (adj.p≤0.01) with adjusted p values as low as $10^{-23}$. For further probe selection we applied both statistical and quantitative cut-offs (adj.p<1.01, absolute fold change ≥2) that reduced the probe set to 824 differentially expressed probes and accordingly represents a global signature of infection for a naïve and immature neonatal immune system. Next, we used Euclidean distance based hierarchical clustering of the 824 differentially expressed features (FIG. 9) to characterise the patterns of expression and reveal distinct sets of up-regulated and down-regulated genes. The output of this cluster analysis developed three demarcated groups: group 1 represents probes differentially down-regulated in infected infants; group 2 those differentially up-regulated in infected infants; while group 3 did not develop clear separation between infected and controls.

A network analysis of 824 probes significantly differentially regulated (adj.p≤1.01, fold change ≥2) upon infection revealed that four major networks of down regulated genes were identified which comprised genes involved in the following processes; protein synthesis, cellular assembly and organization, RNA post-transcriptional modification (Network Score 96); cell death, cellular compromise, protein trafficking (Network Score 80); cell-mediated immune response, cellular development, cellular function and maintenance (Network Score 76); cellular development, nervous system development and function, cell death (Network Score 63). Overall, genes in this group were associated with the following diseases and functions: inflammatory response, immunological disease, hematological disease, cell-mediated immune response, hematological system development and function, hematopoiesis, tissue morphology and immune cell trafficking.

Network analysis of genes up-regulated upon infection (Group 2 from FIG. 10b) showed four major networks of up regulated genes were identified which comprised genes involved in the following processes; inflammatory response, cellular movement, hematological system development and function (Network Score 155); inflammatory response, cellular function and maintenance, cell signaling (Network Score 104); cellular movement, connective tissue disorders, immunological disease (Network Score 84); inflammatory response, inflammatory disease, immunological disease (Network Score 76). Overall, genes in this group were associated with the following diseases and functions: inflammatory response, infectious disease, respiratory disease, connective tissue disorders, immunological disease, hematological system development and function, immune cell trafficking, tissue development, organismal survival and humoral immune response.

Network analysis of genes up regulated upon infection (Group 3 from FIG. 10b). Two major networks of up regulated genes were identified which comprised genes involved in the following processes; hematological disease, organismal injury and abnormalities, cell death (Network Score 109); gene expression, cell cycle, infection mechanism (Network Score 44). Overall, genes in this group were associated with the following diseases and functions: hematological disease, organismal injury and abnormalities, genetic disorder, hematological system development and function, hematopoiesis, tissue morphology, cardiovascular system development and function and connective tissue development and function.

Many of the 118 probes in group 3 detect genes that encode functions related to blood development on the basis of gene ontology and pathway analysis and these were excluded from subsequent analyses.

We next sought to determine the most highly active set of genes associated with infection by applying further additional filtering to group 1 and 2 probes using a more stringent cut off (adj. $p \leq 10^{-5}$, fold change A network analysis of 52-gene dual-network genes highly significantly up and down regulated upon infection (adj.$p \leq 10^{-5}$, fold change $\geq 4$) revealed that one major network (Network Score 72) and 3 minor networks (Network Scores of 3, 2 and 2) of up regulated genes were identified. The major network comprised genes involved in cell-to-cell signalling and interaction, cellular movement and inflammatory response. Overall, genes in this group were associated with the following diseases and functions: infectious disease, respiratory disease, inflammatory response, inflammatory disease, haematological system development and function and immune cell trafficking. Top canonical pathways associated with this network (with p-values in brackets) were as follows: Role of Macrophages, Fibroblasts and Endothelial Cells in Rheumatoid Arthritis ($9.54 \times 10^{-6}$), LXR/RXR Activation ($7.39 \times 10^{-4}$), IL-6 Signaling ($1.51 \times 10^{-3}$), Role of Osteoblasts, Osteoclasts and Chondrocytes in Rheumatoid Arthritis ($2.03 \times 10^{-3}$), Fructose and Mannose Metabolism ($7.87 \times 10^{-3}$).

One major network (Network Score 25) of down regulated genes was identified looking at both direct and indirect interactions. This network comprised genes involved in cell-to-cell signalling and interaction, cell-mediated immune response and cellular development. Overall, genes in this group were associated with the following diseases and functions: genetic disease, immunological disease, haematological disease, gastrointestinal disease, inflammatory disease, haematological system development and function, tissue morphology, immune cell trafficking, cell-mediated immune response and haematopoiesis. Top canonical pathways associated with this network (with p-values in brackets) were as follows: Calcium-induced T Lymphocyte Apoptosis ($2.17 \times 10^{-6}$), CTLA4 Signaling in Cytotoxic T Lymphocytes ($7.52 \times 10^{-6}$), iCOS-iCOSL Signaling in T Helper Cells ($1.17 \times 10^{-5}$), Type I Diabetes Mellitus Signaling ($1.2 \times 10^{-5}$), CD28 Signaling in T Helper Cells ($1.54 \times 10^{-5}$).

Figure 11:
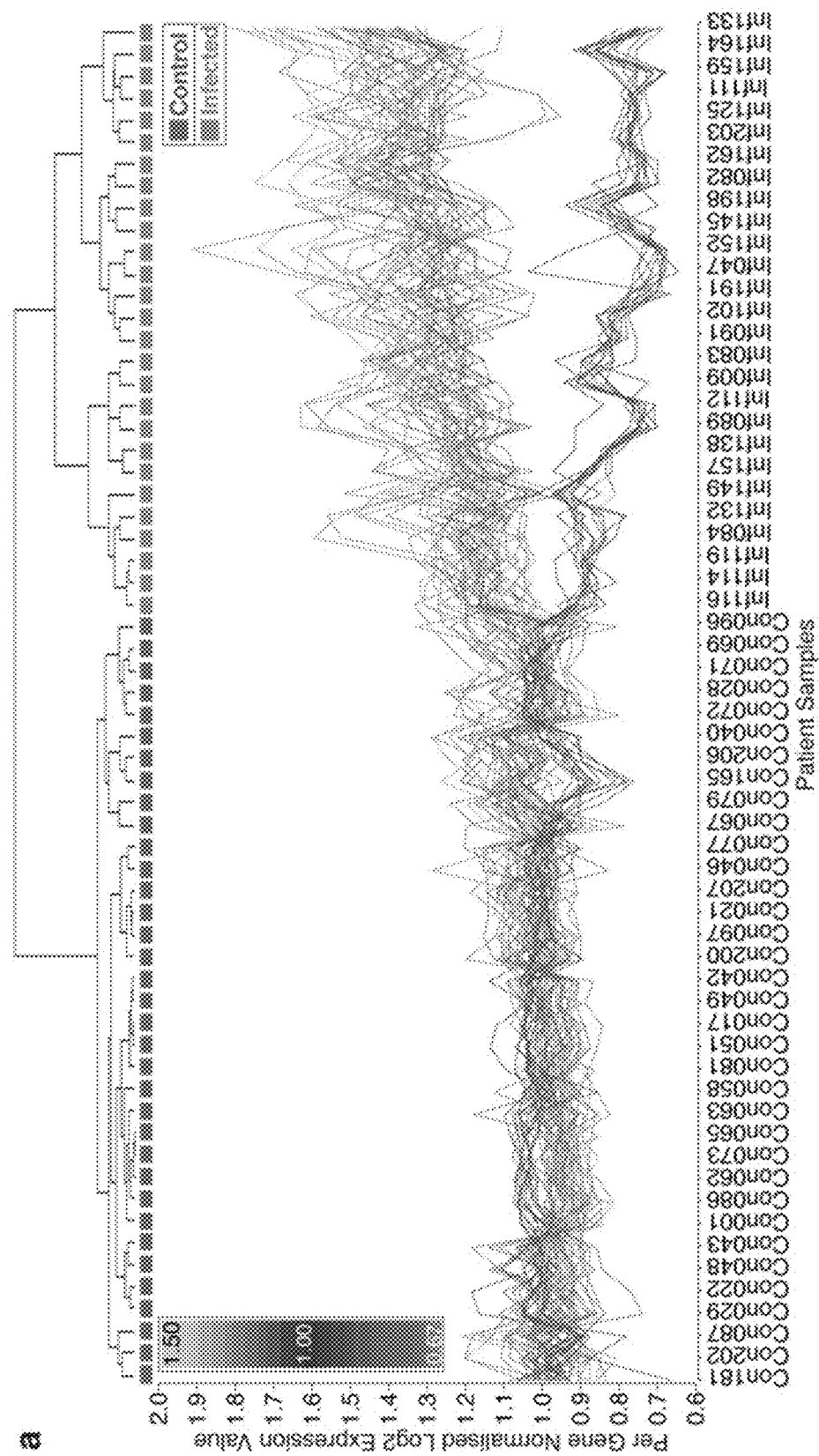
FIG. 11 shows the 52-gene dual-network classifier of neonatal bacterial infection comprised of Innate Immune, Metabolic and Adaptive Immune pathways. Panel (a) shows a line graph of per gene normalized expression values using the 52 gene dual network classifier of neonatal bacterial infection with sample order determined using hierarchical clustering based on Euclidean distance. Line graphs of per gene normalized expression values using genes associated with (b) Innate Immune, (c) Metabolic (d) Adaptive Immune and (e) Combination of all three pathways present in the 52-gene dual-network classifier of neonatal bacterial infection. For the samples on the x-axis, control=dark grey (towards the left), bacterial infected=light grey (towards the right) for 11b to 11e.
Figure 11:
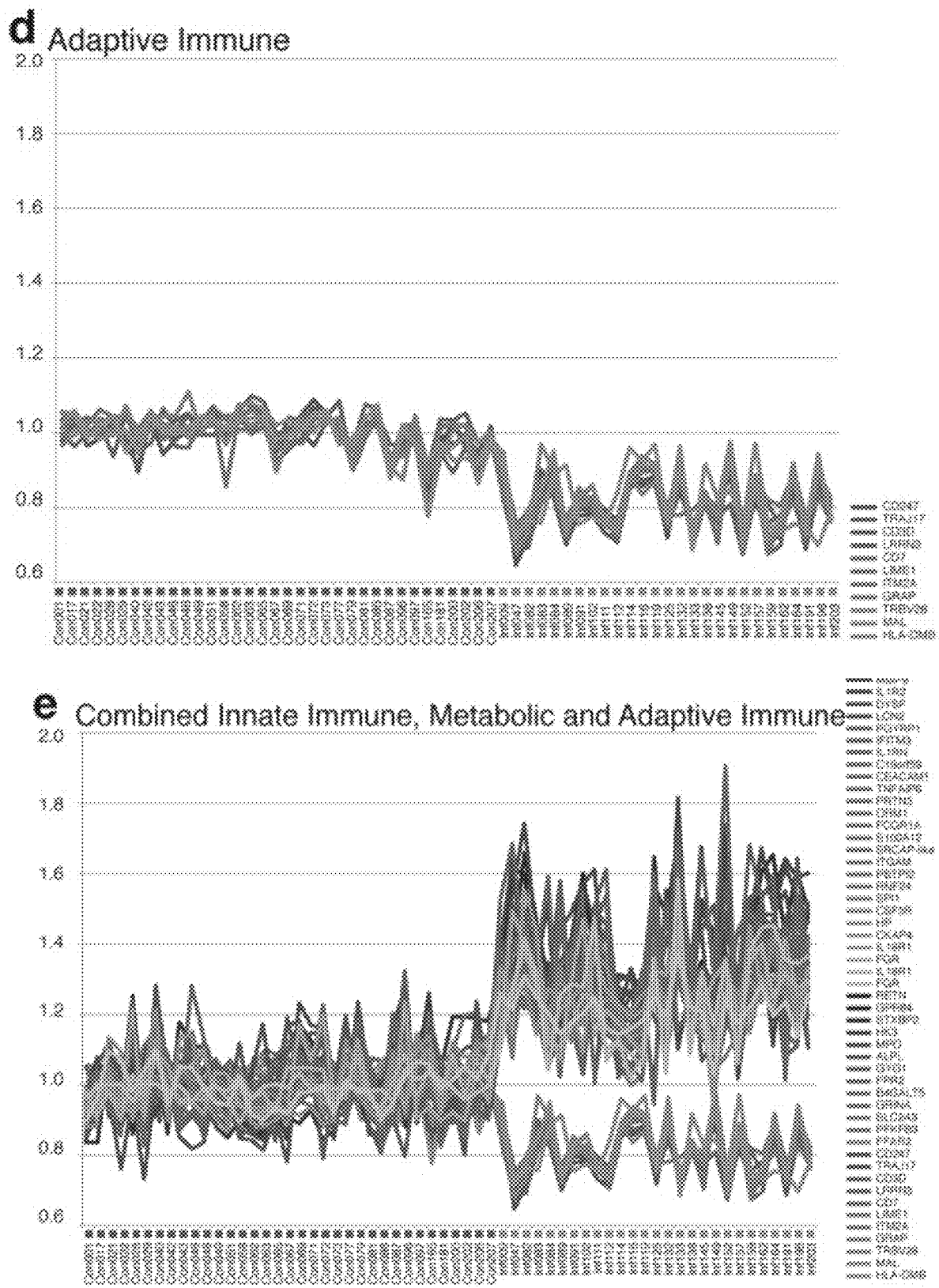

Analysis of the resulting 52 genes revealed sub-networks (termed "dual-network"), for up-regulated and down-regulated expression. The dual-network consists of highly related genes that form three functional classes of innate and adaptive immunity and unexpectedly genes associated with sugar and lipid metabolic functions (FIG. 11b-e). Expression levels for this dual-network in the infected group show a consistent and clear difference in signal separation into activated (yellow) and suppressed (blue) RNA networks (FIG. 11a). Overall these results strongly support the possibility of identifying networks specific to bacterial infection.

EXAMPLE 6

Cellular and Molecular Pathway Biology Responses to Infection in Neonates

Immune signalling pathways: In order to more extensively interrogate the changes in cellular and molecular pathway biology responses occurring upon neonatal infection, a series of statistical pathway analyses were applied. Firstly, analysis of the overall transcriptional response identified in hierarchical cluster groups 1 and 2 was performed using hypergeometric tests for curated networks in the IPA-database (www.ingenuity.com). This analysis developed eight highly connected networks of functionally related genes. Down-regulated (group 1) genes mapped to antigen processing and presentation via MHC II, lymphocyte differentiation, T cell activation and T cell receptor signalling. Up-regulated (group 2) genes mapped to innate immune processes including TLR, chemokine, IL-6, IL-β and JAK-STAT signalling, platelet activation and apoptosis pathways.

Figure 7:
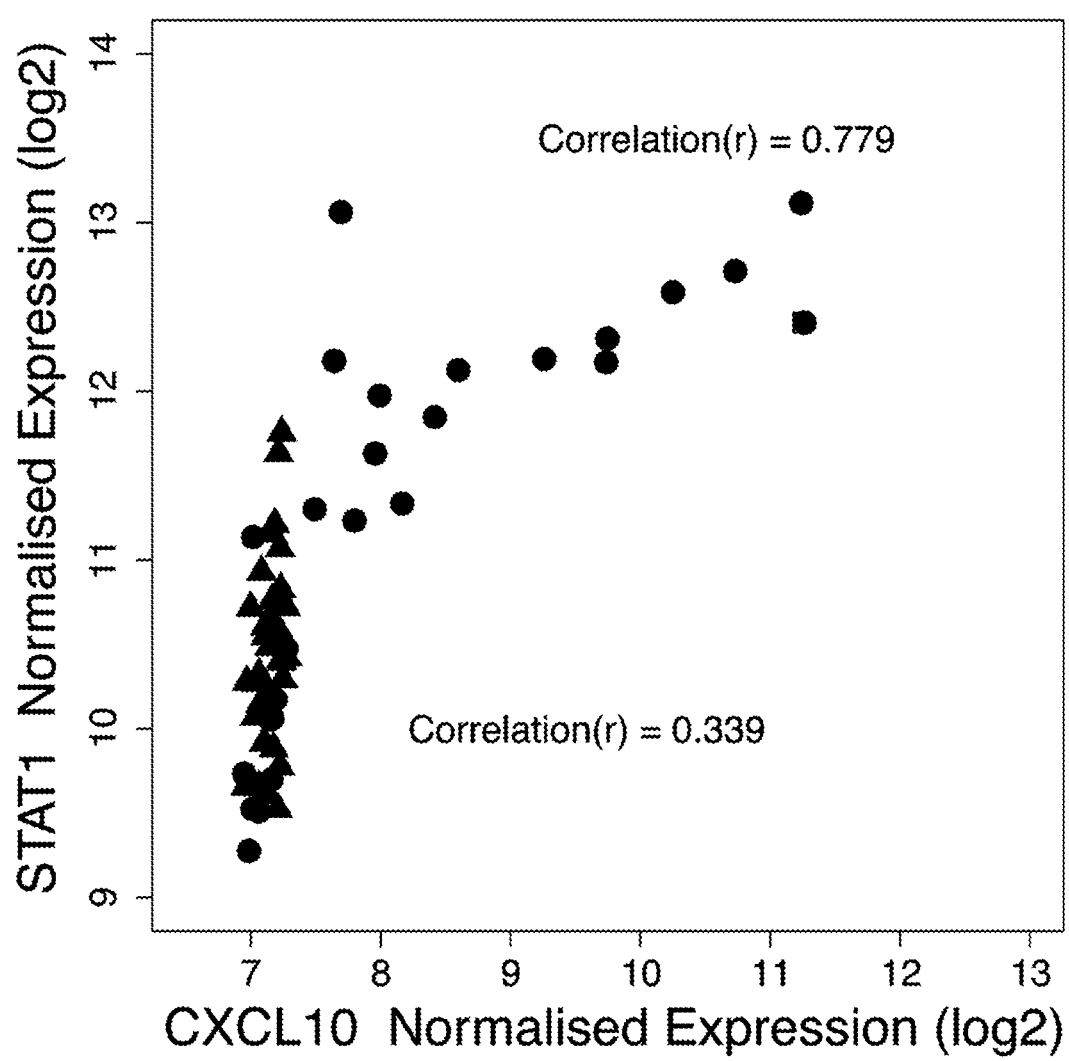
FIG. 7 shows correlation analysis of STAT1 and CXCL10 expression in Control and Infected neonates. Log2 expression levels of STAT1 and CXCL10 are plotted in Control (triangles) and Infected (circles) neonates and correlation of expression determined. Expression is poorly correlated in Control samples but is highly correlated in a subset of infected samples.
Figure 12:
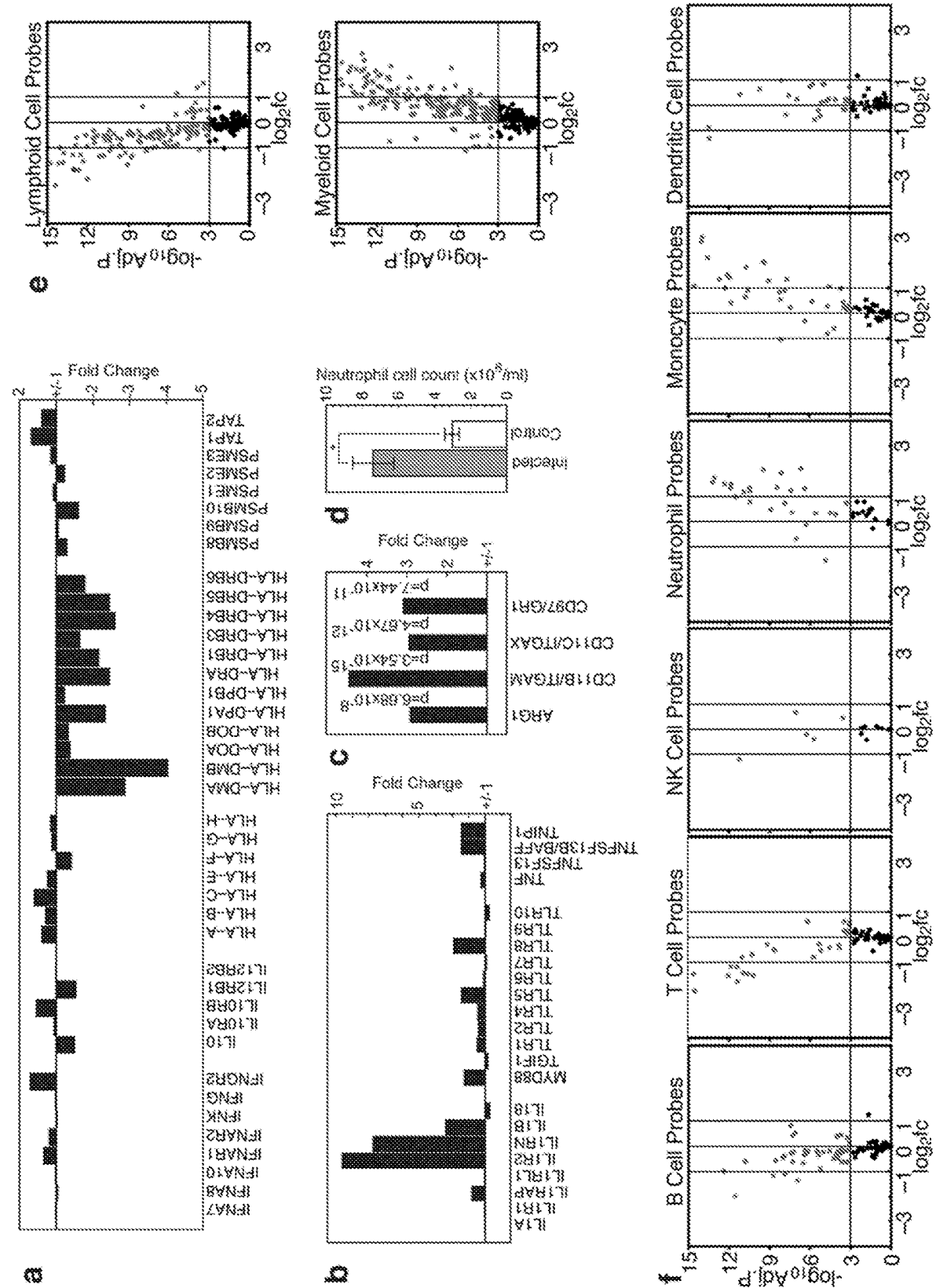
FIG. 12 shows the differential adaptive and innate immune responses to neonatal infection. Panel (a) shows the fold change in expression of adaptive immune response genes following neonatal infection. Panel (b) shows the fold change in expression of innate immune response genes following neonatal infection. Panel (c) shows the fold change in expression of genes associated with myeloid-derived suppressor cells following neonatal infection. Significance is indicated by adjusted p-values for fold change of each probe. Panel (d) shows the neutrophil cell counts from control and infected patients. Neutrophil cell counts were examined in control (n=12) and infected (n=28) patients and are expressed as numbers $\times 10^6$ cellsper ml of blood with the plot presenting median values±median absolute deviation. Significance testing between conditions was performed using a one-way ANOVA test—*indicates significance at p<0.0005. Panels (e & f) show a cell type enrichment analysis. Volcano plots of expression profiles associated with particular blood cell types and classes. $Log_2$ fold change is on the x-axis and -$log_2$ adjusted p value on the y-axis. Panels in (e) show expression profiles for lymphoid and myeloid cells. Panels in (f) show expression profiles for B cells, T cells, NK cells, cells, neutrophils, monocytes and dendritic cells. Significantly differentially expressed probes with (adj.p≤1.01) are shown in grey.

IPA analysis of the more stringent 52 gene list revealed two sub-networks, composed of 3 pathways—two that are associated with the up-regulated set and one for the down-regulated set. The up-regulated set showed a myeloid innate-immune signature anchored around matrix metallopeptidase 9 (MMP9) and lipocalin 2 (LCN2) associated with macrophage activation and lipid metabolism (FIG. 11b). Other up-regulated metabolic genes include the free fatty acid receptor 2 (FFAR2/GPR43) that provides a link between short chain fatty acids, neutrophils and gut-microbiota interactions as well as glycolytic and energy metabolism (FIG. 11c). The down-regulated set was largely comprised of lymphoid markers of adaptive immunity centred around the T cell receptor/CD3 complex and was associated with T cell signalling pathways (FIG. 10d). Taken together, these network alterations provide, for the first time, candidate molecular pathway links to the metabolic and inflammatory processes that occur in neonatal sepsis (FIG. 11e). It is noteworthy that, IFNγ, although detectably expressed in all patient samples, appears not to be differentially activated (FIG. 12a & b). While this is consistent with the reduction in levels of expression of genes of the adaptive immune system (FIG. 11a) such as those involved in antigen presentation (e.g. MHC class II molecules), we find that in the sepsis cases the prototypical IFNγ-regulated gene CXCL10 is induced (most likely via STAT1) showing a good correlation with STAT1 in the infected cases (r~-0.8) but not in the controls (r~0.3)(FIG. 7).

Figure 8:
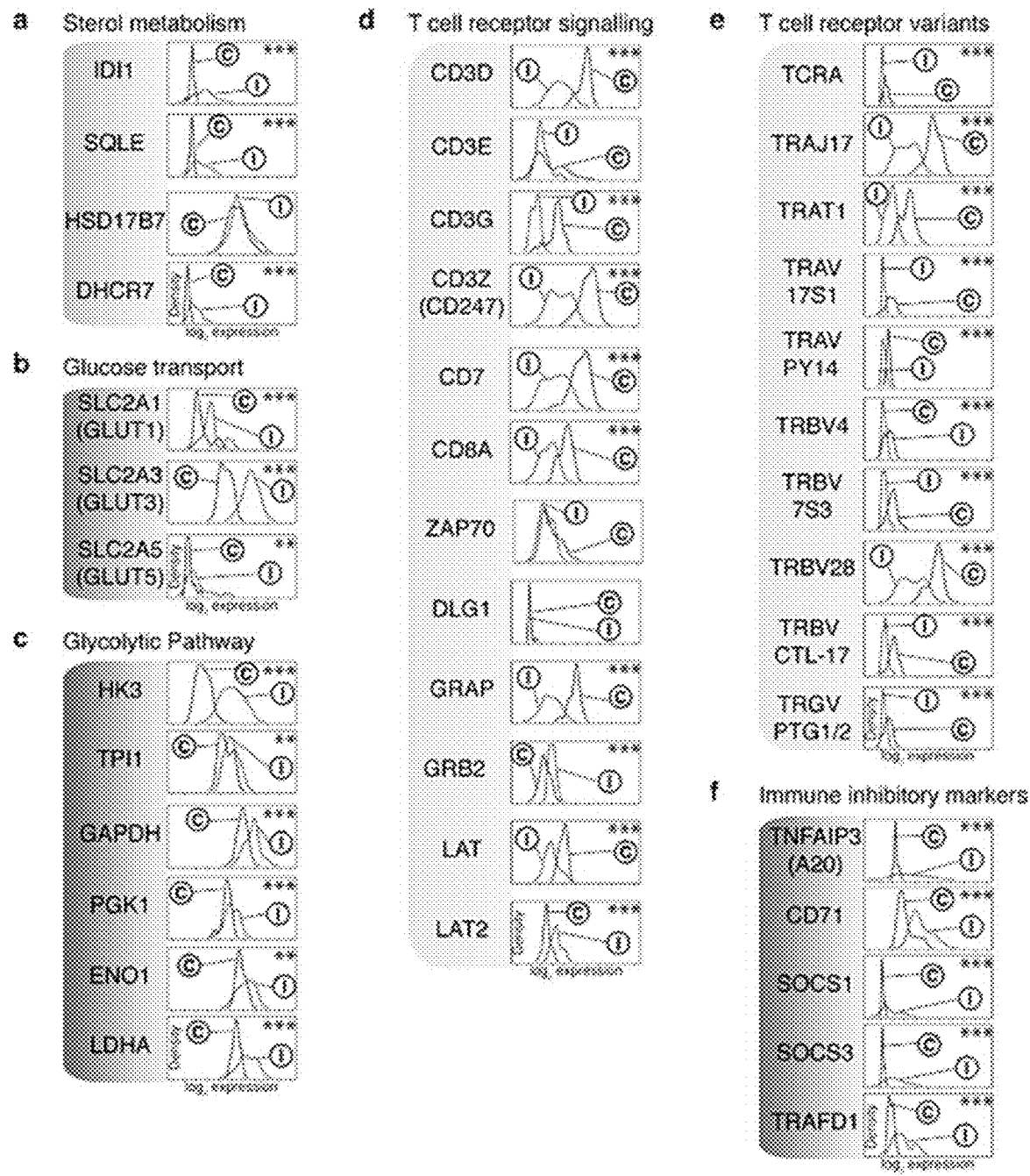
FIG. 8 shows analysis of gene expression of metabolic and immune pathway modules. Gene expression of molecules associated with (a) Sterol metabolism, (b) Glucose transport, (c) Glycolytic pathway, (d) T cell receptor signalling, (e) T cell receptor variants and (f) Immune inhibitory markers. Line graphs display gene expression as probability density plots for control (blue) and bacterial infection (red) samples. Graphs marked with asterisks indicate that the mean expression difference between the two study groups is statistically significant ($p \leq 1.01$, *$p \leq 1.001$).

Immune inhibitory signalling: While genes involved in the innate immune response showed a strong up-regulation of inflammatory cytokines/receptors, TLR, and TNF signalling, there was also a highly potent up-regulation of inhibitory signalling factors such as the receptor decoy for IL-1β (IL1R2) and the IL1 receptor antagonist (IL1RN) (FIG. 11b) that are well known to moderate the immune response. This is manifested as a more general intrinsic innate inhibitory response as key counter-regulatory inhibitory factors elevated include repressors A20, IκBα, TRAFD1, SOCS1 and SOCS3 of the NFκB, TLR and JAK-STAT signalling pathways, respectively (FIG. 8). These counter-regulatory pathways are indicative of developing an altered set point in immune homeostatic control (defined here as the level at which the innate immune system activates the adaptive response) and which will be influenced by the net balance between inhibitory and stimulatory responses. Accordingly, while a significant number of infected infants show high levels of the CD163 macrophage activation marker (adj.p$10^{-6}$), they also exhibit increased co-inhibitory ligands such as PD-L1 (CD274) that would impede T-cell proliferation and cytokine production. Moreover, genes associated with a myeloid-derived suppressor cell (MDSC) signature are also notably elevated (CD11B, CD97) including increased ARG1 that marks a potent anti-inflammatory phenotype (FIG. 12c). In relation to elevated ARG1, the CD71 erythroid cell marker was also up regulated in a significant number of sepsis cases (FIG. 8) and this has been shown recently in neonates to contribute towards the suppression of immune cell activation (Elahi et al., Nature 504, 158-162 (2013)). An important corollary of these stimulatory and inhibitory signalling pathways is that they likely impact on functional changes in immune cellular compartments, in particular the lymphoid arm.

Changes in immune-cell compartments: To investigate whether changes in the cellular compartments could be seen in infection we utilised previously identified markers of specific blood cell lineages (Abbas et al., PLoS One 4, e6098 (2009)) which we translated to the Illumina platform to model cell-type specific modules of RNA expression. These investigations provide insight into the cellularity changes in whole blood in neonatal sepsis. We observe a differential signature of myeloid-cells, especially monocytes and neutrophils, in infected samples (FIG. 12e & f, Table 4), which was validated by a significantly increased neutrophil cell count observed in this group of patients (FIG. 12d). Conversely, gene expression modules for lymphoid cells, particularly B cells and T cells were lower (FIG. 12e & f). A significant difference is not detected for expression modules of either dendritic cells or natural killer cells between infected and controls (Table 4). We conclude that in sepsis the heightened innate immune cellular response is driven by monocytes/macrophages and neutrophils and is counteracted by inhibitory pathways resulting in a net suppression of the adaptive immune arm, especially those associated with the T-cell compartment.

Table 4 shows a cell type enrichment analysis. A summary of probe detection based on cell type specific gene lists and whether expression for each cell type on encountering infection was seen to be unchanged, higher (up) or lower (down).

TABLE 4

| Cell type | Annotated Probes | Expected Probes | Found | Change on Infection | Chi squared p-value |
|---|---|---|---|---|---|
| B Cell | 111 | 14 | 46 | Down | $3.61 \times 10^{-05}$ |
| Dendritic Cell | 108 | 13 | 28 | Unchanged | 0.0191 |
| Lymphoid | 338 | 43 | 128 | Down | $8.03 \times 10^{-11}$ |
| Monocyte | 106 | 13 | 36 | Up | 0.00102 |
| Myeloid | 429 | 55 | 192 | Up | $2.85 \times 10^{-18}$ |
| Neutrophil | 49 | 6 | 29 | Up | 0.000101 |
| NK Cell | 18 | 2 | 5 | Unchanged | 0.257 |
| T Cell | 102 | 13 | 33 | Down | 0.00319 |

Figure 13:
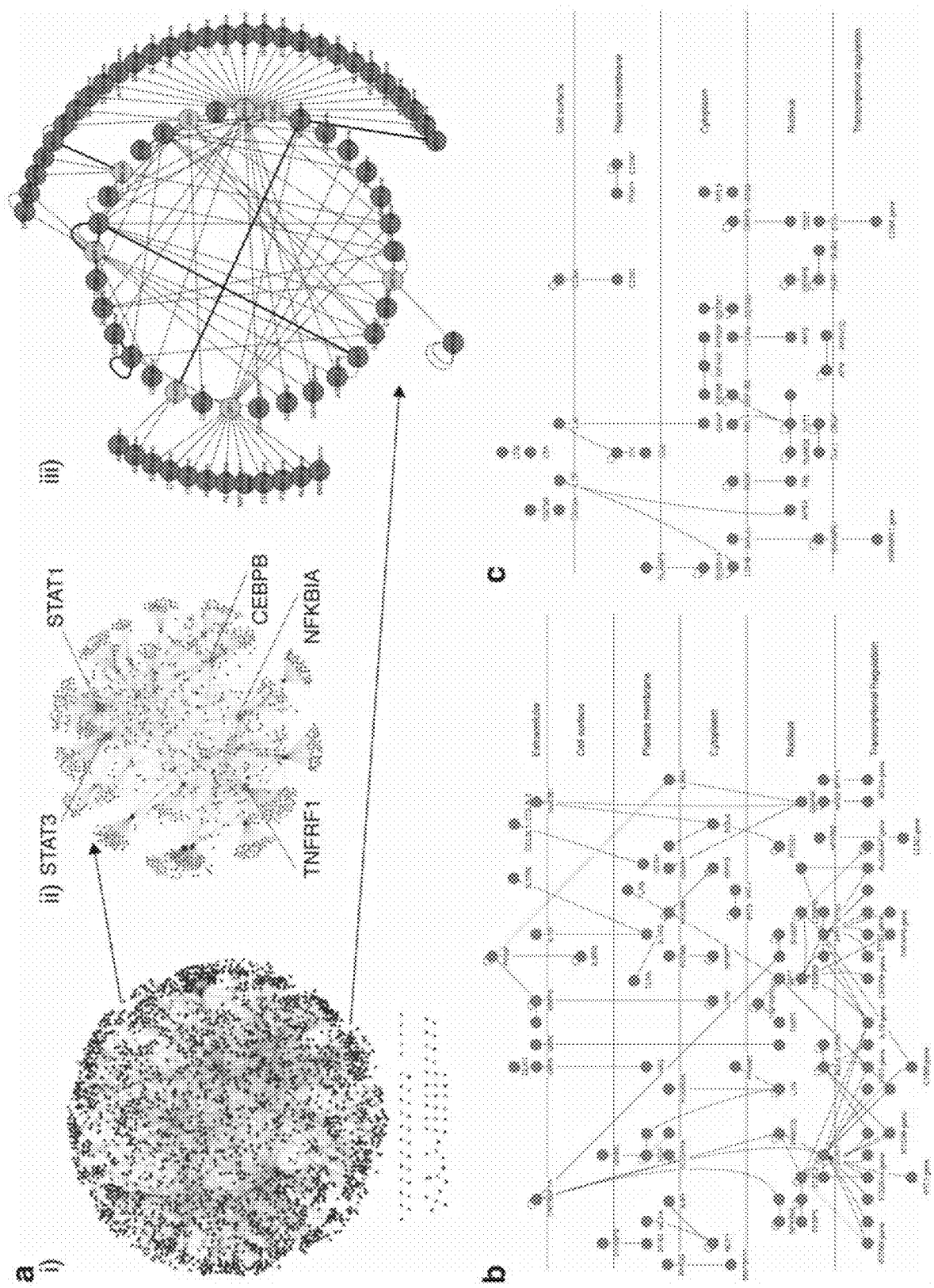
FIG. 13 shows networks of experimentally supported direct molecular interactions between genes differentially regulated in neonatal sepsis. (a) Network relationships derived from InnateDB were visualized with Cytoscape. (i) Network of direct molecular interactions between genes up-regulated in neonatal sepsis patients, their encoded products and all other interacting molecules. Inclusion of non-differentially expressed interacting partners (shown in grey) in this network allows potential identification of important regulatory nodes (genes/proteins) not evident from microarray data alone (e.g. constitutively expressed nodes/nodes expressed at a time-point not sampled in the study). (ii) The top 5 hub nodes identified by Degree algorithm of cytoHubba plugin are labelled. Node sizes are defined by the node degree—the larger the node size the higher the degree. Nodes encoded by up-regulated genes are shown in dark grey, the top 20 hubs identified by this analysis were STAT1, STAT3, NFKBIA, TNFRF1, CEBPB, SPI1, LYN, BCL6, PRKCD, HCK, MYD88, HSPA1B, UBA1, CEBPD, JUNB, IRF7, TNFAIP3, CTNNA1, ETS2 and GNAI2. (iii) The top-scoring up-regulated sub-network identified by jActiveModules plugin. Nodes representing up-regulated RNA signals are shown in dark grey; non-differentially expressed genes in light grey. (b) Network of molecular interactions directly between genes up-regulated in neonatal sepsis patients visualized with the Cerebral v.2 plugin. Nodes encoded by up-regulated genes are shown in red; non-differentially expressed interactions partners are not shown. (c) Network of molecular interactions directly between genes down regulated in neonatal sepsis patients visualized with the Cerebral v.2 plugin. Nodes encoded by down-regulated genes are shown in green; non-differentially expressed interaction partners are not shown.

Regulatory pathways: To gain further insight into the underlying regulatory pathway alterations upon infection we performed a supervised analysis of differentially-regulated gene sets using the InnateDB resource (Lynn et al., Mol Syst Biol 4, 218 (2008)), a systems biology database which contains >18,000 experimentally-validated molecular interactions of relevance to innate immunity. For the purpose of this investigation we used only a high confidence dataset of InnateDB comprising approximately 2500 human interactions that had been manually annotated. Network analysis of direct interactions between up-regulated genes (group 2) and their encoded products was undertaken to include all non-differentially expressed interacting partners of the up-regulated genes (FIG. 13ai). The resultant network revealed those markers (represented as "nodes" in the network) that are highly connected through direct physical or biochemical interactions (termed "hubs") or which have many network shortest paths passing through them (termed "bottlenecks") that mark potential key regulatory points in the network. The 20 major hubs in this network were identified, of which, the top 4 included the immune-regulatory transcription factors STAT1, STAT3, and C/EBP-B, and the TNFR1 receptor (FIG. 13aii). These innate immune responses trigger antigen presenting cell maturation to instruct the adaptive immune response. The level of innate immune response triggering reflects the set-point for homeostatic immune regulation, and thus points to a heightened set point neonatal sepsis. The network was further analysed to identify 'active sub-networks' via the identification of high scoring sub-networks using a search algorithm based on simulated annealing (Ideker et al., Bioinformatics 18 Suppl 1, S233-240 (2002)). The top-ranked up-regulated sub-network (FIG. 13aiii), consisted of 81 nodes and 176 edges and was enriched in genes involved in Formation of Platelet plug, Fc gamma R-mediated phagocytosis, Platelet Activation, Hemostasis, Integrin signalling and chemokine signalling pathways. Several members of the TLR signalling pathway were also components of this sub-network.

Additionally, using InnateDB, we also undertook another supervised network analysis that investigated the interactions directly between nodes that were up-regulated in neonatal infection i.e. we did not consider interactions with non-differentially expressed nodes or down-regulated nodes in this analysis (FIG. 13b). This network was composed of a major connected component consisting of proteins involved in TLR (TLR5, TLR8, MYD88, IRAK3) and TNF signalling (among other pathways) leading to the transcriptional activation of a range of genes via a panel of transcription factors including BCL6, CEBPB, CEBPD, ETS2, IRF7, JUNB, SPI1, STAT1 and STAT3. Gene ontology analysis revealed that the top 2 significantly enriched terms were the innate immune response and inflammatory response. Minor components in the network consisted of genes involved in platelet activation (GNAI2, PPBP) and chemokine/cytokine signalling (GNAI2, IL8RA, IL8RB, PPBP) and involved in Fc gamma R-mediated phagocytosis (DNM2, FCGR1A, FCGR2A, HCK, LYN). Altogether these changes are consistent with innate-immune responses triggering antigen presenting cell maturation.

Next, we completed a similar analysis investigating interactions between down-regulated nodes and all their interaction partners. The top 20 hubs in the down-regulated network were identified and included the ETS1 transcription factor, several genes involved in translation (EIF3E, EIF4A2, RPLP1, TUT1), 2 genes involved in cell cycle regulation (A™, RBL2) and the cytokine receptor, IL7R. Many of these nodes were also identified as network bottlenecks. The top 3 differentially expressed sub-networks consisted of a network enriched in genes involved in translation, the HNF4A transcriptional module and a network enriched in components of the T cell signalling pathway, respectively. Network analysis of molecular interactions between down regulated genes in neonatal infection was also generated using InnateDB, (FIG. 13c). This network revealed that there were very few molecular interactions directly between down-regulated genes or their encoded products.

Taken together these findings show that the overriding pathophysiological signal associated with neonatal infection is one of increased innate-immune-metabolic response with an unbalanced homeostatic regulation of the adaptive-immune response. The specific and intense activation of innate immune signalling, moderated via inhibitory pathways is consistent with the notion of an elevated set point in neonates in comparison with adults for guiding a suppressed adaptive immune response (Ghazal et al., *Curr Opin Infect Dis* 26, 213-218 (2013).

EXAMPLE 7

Immune Homeostasis and Metabolic Pathway Biology Responses

Figure 16:
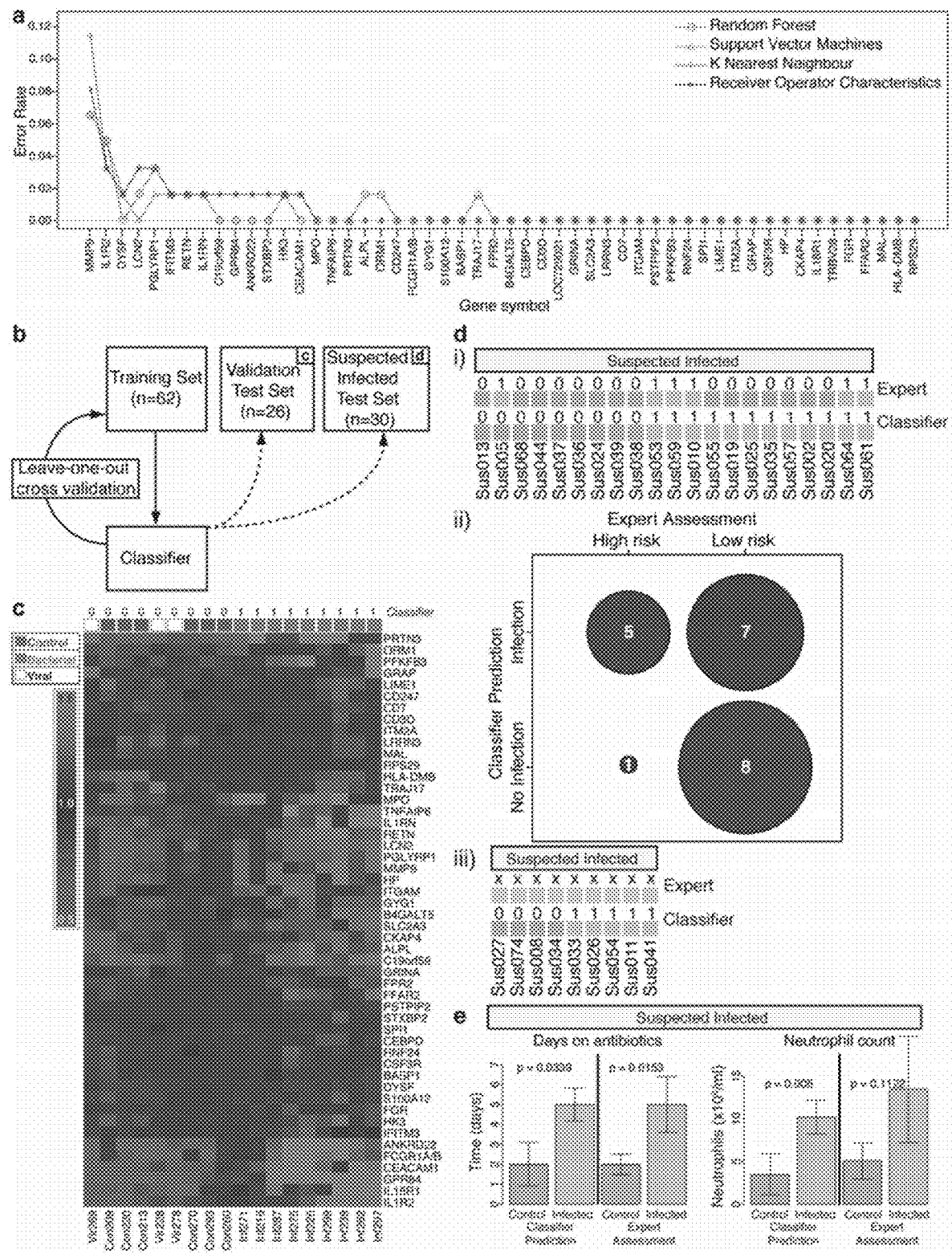
FIG. 16 shows the validation of the 52-gene dual-network classifier. Panel (a) shows members of the network as a classifier of neonatal infection using leave one out cross validation analysis using four independent machine learning algorithms ('circle'—Random Forest, 'triangle'—Support Vector Machines, '+'—k Nearest Neighbour and 'x'—Receiver Operator Characteristics). Panel (b) is a flow chart of biomarker classifier validation. Flow chart showing the samples used for classifier generation and the validation results. Panel (c) is a heat map showing hierarchical clustering of 18 infant samples (9 bacterially infected, 6 control, 3 virally infected) based on the 50 probes that were in common between the classifier gene set and the Affymetrix U219 platform. Hierarchical clustering was based on Euclidean distance. Control—blue, bacterial infected—red, viral infected—black. Classification of bacterial infection is indicated (0=non-infected, 1=infected). (d) Comparison of microarray based classifier and expert assessment for classification of samples from patients with suspected infection. i) Comparison of expert assessment and microarray based classification on samples scored 'high' and low' likelihood of infection by expert assessment. ii) Microarray based classifier prediction and expert assessment of suspected sepsis cases (top left=concordance of 'infection', bottom right=concordance of 'control', top right and bottom left=discordance of microarray classifier and expert assessment). iii) Microarray based classification of samples scored 'medium' likelihood of infection by expert assessment. Classification of bacterial infection is indicated (0=non-infected (pale blue), 1=infected (pink)). A heat map showing the 30 infant samples of suspected infection based on the 46 probes that were in common between the classifier gene set and the CodeLink platform is shown in FIG. 8. Panel (e) contains histograms showing clinical criteria in suspected infection cases as judged by the microarray classifier and expert assessment. Days on antibiotics and neutrophil counts are shown for samples based on classification of control (left hand bar in each graph) and bacterial infection (right hand bar in each graph).

Unexpectedly, we found marked transcriptional changes associated with sepsis in specific metabolic pathways principally those associated with glucose, energy and cholesterol metabolism (FIG. 8). For cholesterol biosynthesis and homeostasis we find significant alterations in SQLE, IDI1, DHCR7, SCAP, INSIG2, NR1H2, ABCA1, LDLR and LDLRAP1 (FIG. 8). In the case of the glycolysis pathway three key regulatory nodes of the pathway form part of the 52-gene dual-network (FIG. 16c). These are increased levels of the glucose transporter GLUT3 (SLC2A3), PFKFB3 (6-phophofructo-2-kinase) that activates the glycolytic flux under hypoxic conditions and HK3 a hexokinase that phosphorylates glucose to produce glucose-6-phosphate, the first rate-limiting step in glucose metabolism; and is indicative of changes in the TCA cycle. Another member of the dual network that is involved in regulating lipid and glucose metabolism is LCN2 (Akelma et al., *JPEM* 25, 525-528 (2012); Huang et al., *Cardiovascular Diabetology* 11, 11 (2012)) which also plays a role in the innate immune response to bacterial infection by sequestering iron (Berger et al., *Proc Natl Acad Sci* 103, 1834-1839 (2006); Flo et al., *Nature* 432, 917-921 (2004); Goetz et al., *Molecular Cell* 10, 1033-1043 (2002); Srinivasan et al., *J Immunol* 189, 1911-1919 (2012)). Other metabolic processes that are key nodes in the dual network include B4GALT5 that is responsible for synthesis of complex N-linked oligosaccharides for glycoproteins and glycolipids; and GYG1 that forms an oligosaccharide primer substrate for glycogen synthase. These metabolic pathway alterations are likely to be linked to the innate immune response. In support, analysis of the promoters of the metabolic sub-network identified 11 out of 13 genes containing binding sites for the myeloid specific transcription factor PU.1 (SPI1), which is also part of the 52-gene dual-network (Table 5).

TABLE 5

(overleaf). Predicted SPI1 binding sites in metabolic sub-network genes. Human single site analysis of 13 Metabolic network genes for SPI1 binding sites predicted using oPOSSUM 3.0 (JASPAR ID: MA0080.2, Class: Winged Helix-Turn-Helix, Family: Ets, Tax group: vertebrates, Information content: 9.64)

| Gene ID(s) | Ensembl ID(s) | Chr | Start | End | Str. | Nearest TSS | TFBS Start | TFBS End | TFBS Rel. Start | TFBS Rel. End | TFBS Str. | Abs. Score | Rel. Score | TFBS Sequence |
|---|---|---|---|---|---|---|---|---|---|---|---|---|---|---|
| MPO | ENSG00000005381 | 17 | 56347217 | 56358296 | − | 56358296 | 56359160 | 56359166 | −870 | −864 | + | 9.156 | 92.00% | AGGAAAT |
|  |  |  |  |  |  |  | 56358296 | 56359192 | 56359198 | −902 | −896 | + | 8.328 | 89.30% | AGGAAGG |
|  |  |  |  |  |  |  | 56358296 | 56359234 | 56359240 | −944 | −938 | − | 11.543 | 100.00% | AGGAAGT |
|  |  |  |  |  |  |  | 56358296 | 56362380 | 56362386 | −4090 | −4084 | − | 9.156 | 92.00% | AGGAAAT |
| SLC2A3 | ENSG00000059804 | 12 | 8071826 | 8088871 | − | 8088871 | 8090996 | 8091002 | −2131 | −2125 | + | 9.156 | 92.00% | AGGAAAT |
| STXBP2 | ENSG00000076944 | 19 | 7701991 | 7712759 | + | 7701991 | 7697773 | 7697779 | −4218 | −4212 | − | 11.543 | 100.00% | AGGAAGT |

TABLE 5-continued (overleaf). Predicted SPI1 binding sites in metabolic sub-network genes. Human single site analysis of 13 Metabolic network genes for SPI1 binding sites predicted using oPOSSUM 3.0 (JASPAR ID: MA0080.2, Class: Winged Helix-Turn-Helix, Family: Ets, Tax group: vertebrates, Information content: 9.64)

| Gene ID(s) | Ensembl ID(s) | Chr | Start | End | Str. | Nearest TSS | TFBS Start | TFBS End | TFBS Rel. Start | TFBS Rel. End | TFBS Str. | Abs. Score | Rel. Score | TFBS Sequence |
|---|---|---|---|---|---|---|---|---|---|---|---|---|---|---|
| | | | | | | 7701991 | 7697822 | 7697828 | -4169 | -4163 | - | 11.543 | 100.00% | AGGAAGT |
| | | | | | | 7701991 | 7698312 | 7698318 | -3679 | -3673 | - | 8.328 | 89.30% | AGGAAGG |
| | | | | | | 7702011 | 7702629 | 7702635 | 619 | 625 | - | 8.679 | 90.50% | AGGAAGA |
| RETN | ENSG00000104918 | 19 | 7733972 | 7735340 | + | 7733972 | 7730825 | 7730831 | -3147 | -3141 | + | 8.679 | 90.50% | AGGAAGA |
| | | | | | | 7733972 | 7731144 | 7731150 | -2828 | -2822 | + | 8.762 | 90.70% | AAGAAGT |
| FFAR2 | ENSG00000126262 | 19 | 35940617 | 35942667 | + | 35940617 | 35939096 | 35939102 | -1521 | -1515 | - | 8.328 | 89.30% | AGGAAGG |
| | | | | | | 35940617 | 35940295 | 35940301 | -322 | -316 | - | 11.543 | 100.00% | AGGAAGT |
| GPR84 | ENSG00000139572 | 12 | 54756229 | 54758271 | - | 54758271 | 54758347 | 54758353 | -82 | -76 | - | 11.543 | 100.00% | AGGAAGT |
| | | | | | | 54758271 | 54761957 | 54761963 | -3692 | -3686 | - | 9.359 | 92.70% | GGGAAGT |
| | | | | | | 54758271 | 54761986 | 54761992 | -3721 | -3715 | + | 9.359 | 92.70% | GGGAAGT |
| | | | | | | 54758271 | 54762004 | 54762010 | -3739 | -3733 | + | 9.359 | 92.70% | GGGAAGT |
| | | | | | | 54758271 | 54762031 | 54762037 | -3766 | -3760 | + | 8.637 | 90.30% | AGGAACT |
| | | | | | | 54758271 | 54762078 | 54762084 | -3813 | -3807 | - | 11.543 | 100.00% | AGGAAGT |
| | | | | | | 54758271 | 54762456 | 54762462 | -4191 | -4185 | - | 8.679 | 90.50% | AGGAAGA |
| | | | | | | 54758271 | 54763182 | 54763188 | -4917 | -4911 | + | 8.637 | 90.30% | AGGAACT |
| B4GALT5 | ENSG00000158470 | 20 | 48249482 | 48330415 | - | 48330415 | 48326776 | 48326782 | 3634 | 3640 | + | 9.156 | 92.00% | AGGAAAT |
| HK3 | ENSG00000160883 | 5 | 176307870 | 176326333 | - | 176318539 | 176320056 | 176320062 | -1523 | -1517 | + | 8.637 | 90.30% | AGGAACT |
| | | | | | | 176326333 | 176326431 | 176326437 | -104 | -98 | + | 9.198 | 92.20% | AGGAAGC |
| | | | | | | 176326333 | 176326441 | 176326447 | -114 | -108 | - | 11.543 | 100.00% | AGGAAGT |
| ALPL | ENSG00000162551 | 1 | 21835858 | 21904905 | + | 21896796 | 21892048 | 21892054 | -4748 | -4742 | + | 8.637 | 90.30% | AGGAACT |
| | | | | | | 21896796 | 21892058 | 21892064 | -4738 | -4732 | + | 9.156 | 92.00% | AGGAAAT |

TABLE 5-continued (overleaf). Predicted SPI1 binding sites in metabolic sub-network genes.
Human single site analysis of 13 Metabolic network genes for SPI1 binding
sites predicted using oPOSSUM 3.0 (JASPAR ID: MA0080.2, Class: Winged
Helix-Turn-Helix, Family: Ets, Tax group: vertebrates, Information
content: 9.64)

| Gene ID(s) | Ensembl ID(s) | Chr | Start | End | Str | Nearest TSS | TFBS Start | TFBS End | TFBS Rel. Start | TFBS Rel. End | TFBS Str. | Abs. Score | Rel. Score | TFBS Sequence |
|---|---|---|---|---|---|---|---|---|---|---|---|---|---|---|
| | | | | | | 21896796 | 21892199 | 21892205 | -4597 | -4591 | - | 8.679 | 90.50% | AGGAAGA |
| | | | | | | 21896796 | 21892462 | 21892468 | -4334 | -4328 | + | 8.679 | 90.50% | AGGAAGA |
| GYG1 | ENSG00000163754 | 3 | 148709128 | 148745419 | + | 148709128 | 148704918 | 148704924 | -4210 | -4204 | + | 7.661 | 87.10% | ATGAAGT |
| | | | | | | 148709128 | 148705332 | 148705338 | -3796 | -3790 | - | 9.156 | 92.00% | AGGAAAT |
| | | | | | | 148709128 | 148705377 | 148705383 | -3751 | -3745 | - | 9.156 | 92.00% | AGGAAAT |
| | | | | | | 148709128 | 148706587 | 148706593 | -2541 | -2535 | + | 8.328 | 89.30% | AGGAAGG |
| | | | | | | 148709128 | 148708354 | 148708360 | -774 | -768 | - | 11.543 | 100.00% | AGGAAGT |
| | | | | | | 148735489 | 148735200 | 148735206 | -289 | -283 | - | 7.819 | 87.60% | AGGAATT |
| PFKFB3 | ENSG00000170525 | 10 | 6186881 | 6277495 | + | 6186881 | 6186778 | 6186784 | -103 | -97 | - | 9.198 | 92.20% | AGGAAGC |
| | | | | | | 6263367 | 6260005 | 6260011 | -3362 | -3356 | + | 8.328 | 89.30% | AGGAAGG |

Another crucial contribution to coupling the homeostasis of host metabolism and the immune system is the microbial colonization of the intestine at birth. Here homeostatic regulatory pathways involve interactions between immune cells and metabolic products (primarily small chain fatty acids such as butyrate) of microbiota fermentation which influences the set point for an immune response. In this connection, the regulatory pathway governed by free fatty acid receptor 2 (FFAR2/GPR43) plays a key role in linking the metabolic activity of the gut microbiota with body energy metabolism and immune activity. FFAR2 is also an immune-metabolic node within the dual network that is significantly up regulated in our neonatal sepsis cases and in terms of immune homeostasis has immune stimulatory roles upon engagement with a host ligand m-ficolin (FCN1) or immune inhibitory roles upon binding short chain fatty acids.

Figure 14:
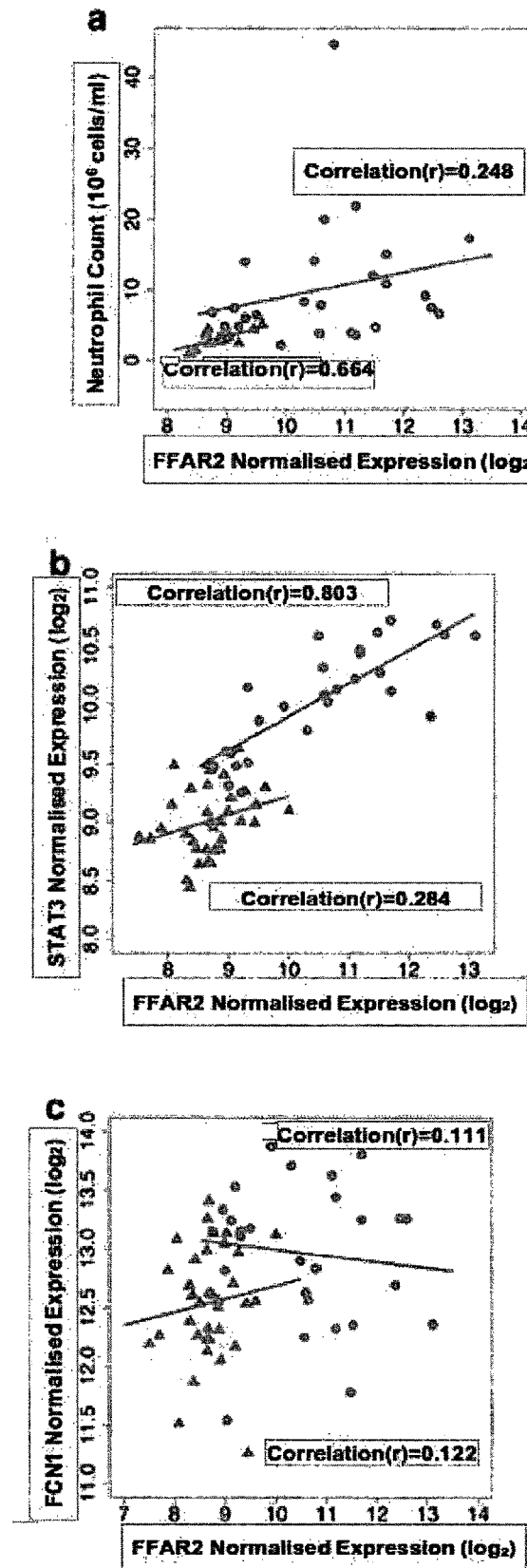
FIG. 14 shows immune metabolic regulatory pathways. Panels (a)-(c) shows a correlation analysis of FFAR2 gene expression with Neutrophil count, STAT3 and FCN1 (m-Ficolin) gene expression in control (triangles) and bacterial infection (circles). Panel (e) and (e) shows an analysis of gene expression in molecules associated with T cell and antigen presenting cell co-stimulatory and co-inhibitory interactions. Line graphs display gene expression as probability density plots for control (blue) and bacterial infection (red) samples. Graphs marked with asterisks indicate that the mean expression difference between the two study groups is statistically significant (*p≤1.05, p≤1.01, *p≤1.001).
Figure 14:
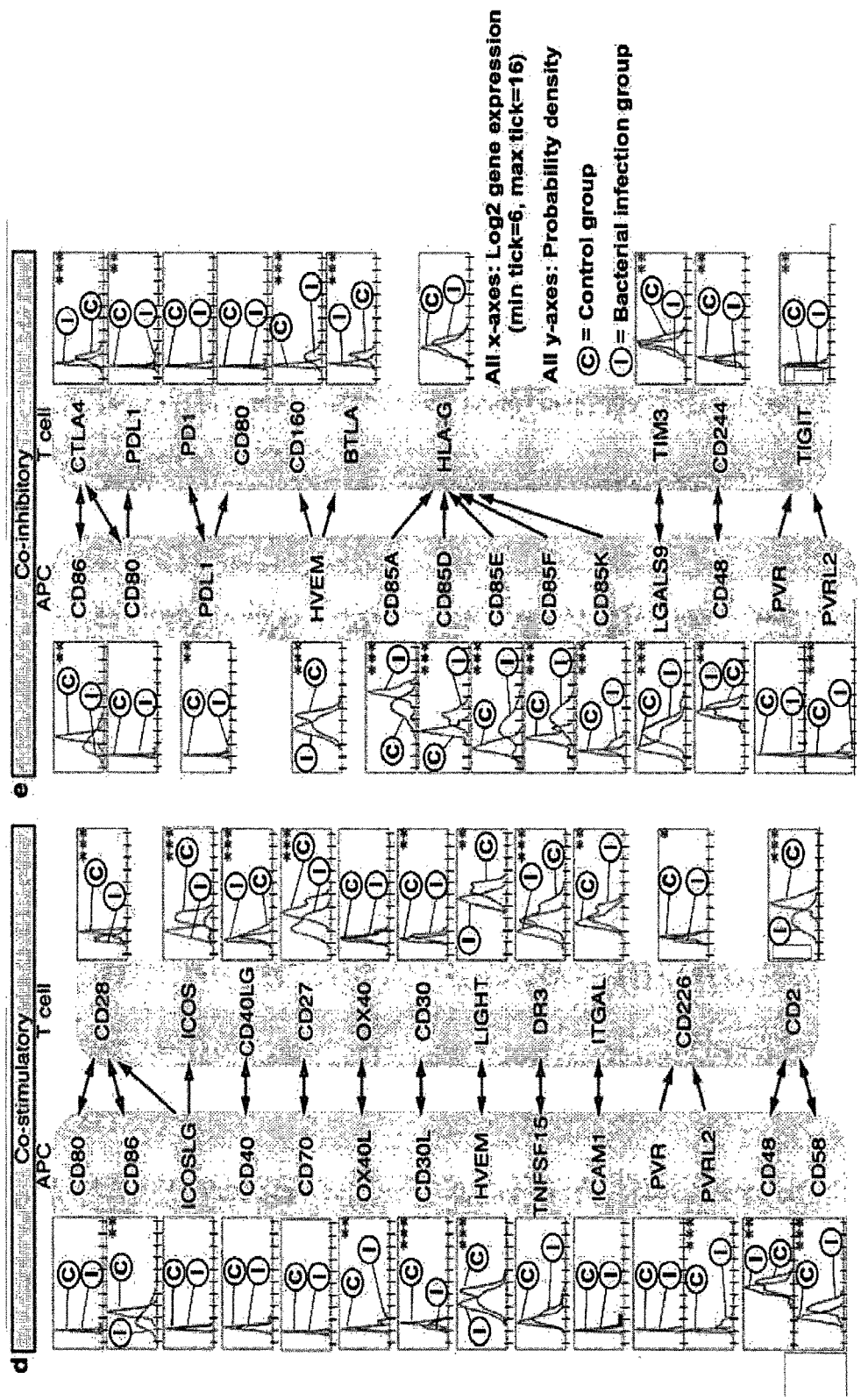

FFAR2 is primarily expressed on neutrophils and granulocytes but is also present on colonic T cells. A positive correlation between FFAR2 levels and the number of neutrophils in the control group is observable (r~0.7) but this correlation is lost in bacterial infection cases (r~0.2), indicating that the up-regulation in sepsis is not simply due to increased neutrophil numbers but is suggestive of an immune mediated up-regulated response (FIG. 14a). STAT3 is one of the key immune regulated hubs in sepsis (FIG. 13aii) and the FFAR2 promoter has a predicted STAT3 binding site (Fisher score 0.9). In agreement, we find FFAR2 has a strong correlation with the levels of STAT3 in neonatal sepsis patients (r~0.8) but not in the controls (r~0.3) (FIG. 14b). In contrast correlation between FFAR2 levels and FCN1 in either controls (r~0.1) or infected group (r~0.1) is low (FIG. 14c). M-ficolin (FCN1) encodes a collagen-type (C-type) lectin protein secreted by macrophages that binds FFAR2 on plasma membranes acting as part of the host innate immune activation pathway. Thus rather than the host factor FCN1, microbial short chain fatty acid metabolites derived from the gut microbiota such as butyrate likely act as the cognate ligands for FFAR2 on neutrophils which functionally tunes the peripheral immune system (Kamada et al., Nat Rev Immunol 13, 321-335, doi:10.1038/nri3430 (2013); Smith et al., Science 341, 569-573, doi:10.1126/science.1241165 (2013)). These results will require further investigation but is consistent with the emerging view that the metabolic activity of the neonatal microbiota may contribute to control the systemic threshold of activation of innate and adaptive immune cells.

Recently the activity of immunosuppressive CD71[+] erythroid cells have been implicated in suppressing the host defence against infection in neonates (Elahi et al., Nature 504, 158-162 (2013)). The up-regulation of CD71 is also found in our study but occurs in only about 25% of our sepsis cases (FIG. 8) and while consistent with the study of Elahi et al. (Elahi et al., Nature 504, 158-162 (2013)) is insufficient alone to explain the more general hypo-responsiveness of the adaptive arm. The interaction between myeloid antigen presenting cells (APC) and lymphoid T cells, however, may serve as a more general homeostatic integration centre for governing the adaptive effector arm of the immune system. Interaction of antigen-HLA complexes in T-cell activation requires two signals, TCR signalling and co-signal regulation. In comparison with the control group, expression of HLA class II is significantly down regulated in neonatal sepsis cases indicating a potentially reduced level of antigen presentation and TCR signalling (FIG. 12a). Moreover, naïve T cells are strongly dependent on co-signalling which plays a vital role in either promoting or inhibiting T cell activation. The CD80/CD86/CD28 interaction is the strongest co-stimulatory pathway and CD28 deficient cells fail to proliferate. In our neonatal sepsis cases we find the differential gene expression for this pathway is dramatically diminished as well as expression of ICOS, CD27, LIGHT, and CD2 (FIG. 14d). Although there was a small number of infected cases that showed increased TNFSF15, ICAM1, LFA-1 and 3 expression, the notably marked down regulation of CD3, LIGHT and CD2 was indicative of a suppression of T cell priming that plays a role in the transition from quiescent to activated states (FIG. 14d and FIG. 8). In the case of co-inhibitory pathways a highly specific and selective differential gene expression response was observed for the inhibitory receptor Ig-like transcripts (CD85A, CD85D, E, F and K) (Shiroishi et al., *PNAS* 100, 8856-8861 (2003); Brown et al., *Tissue Antigens* 64, 215-225 (2004); Anderson and Allen, *Immunology* 127, 8-17 (2009); Chang et al., *Nat Immunol* 3, 237-243 (2002))(FIG. 14e). The increased expression of these markers has the capacity in the specific case of CD85K to convert T cells into suppressive cells (Chang et al., *Nat Immunol* 3, 237-243 (2002)). Thus examination of the complex co-signalling regulatory system reveals a highly focused and selective response in neonatal sepsis. While these responses may be dynamically varied at the time of sampling, they clearly show quite a remarkably restricted and specific pattern. These negative regulatory pathways are suggestive of a significant new mechanism in neonates for contributing to the suppression of the adaptive arm.

EXAMPLE 8

Infection-specific Network Responses

Figure 15:
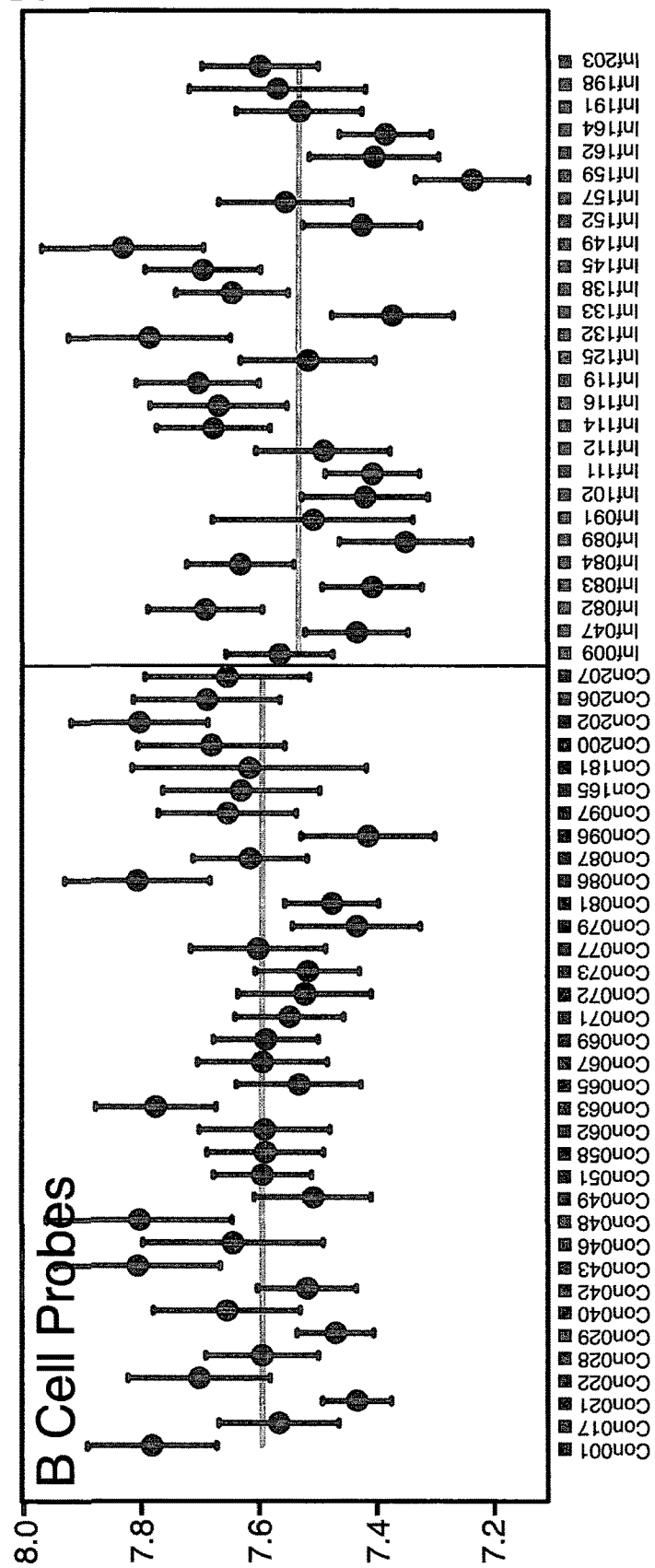
FIG. 15 shows a network analysis of patient specific response to infection. (a) Patient specific expression profiles. Networks of 824 statistically differentially expressed probes (adj.p ≤1.01, fold change ≥2) visualised using BioLayout Express 3D. Three groups of genes are identified which correspond to those identified by hierarchical clustering in FIG. 1*b*. Co-expressed genes within networks were then defined with a Pearson correlation r=0.78 and by applying a Markov clustering (MCL) Inflation value of 4 and Pre-inflation value of 3 and are shown as coloured clusters (e.g. Cluster 01 etc.). (b) Twelve MCL clusters of genes are displayed for bacterial infected patients to show patient specific responses. Average expression values of MCL clusters were calculated from per gene normalized against mean of control samples and ordered by Euclidean distance. (c) 12 gene expression clusters showing heterogeneity within the group of infected neonates were tested for association with clinical parameters. For each infected neonate and cluster, median gene expression was calculated and tested for statistical association with each of the clinical parameters. Wilcoxon rank sum tests were used to test association with binary clinical parameters, Spearman rank correlation tests were used to test association with continuous clinical parameters (Sugar, Neutrophil count, Postnatal age, Platelets, Duration on Antibiotics, pH, WCC, Hb, Gestational age). Dark blocks identify significant test outcome at p≤1.05. (d) Cell type enrichment analysis performed at an individual patient level show patient specific responses. Median signal levels for cell type specific gene lists are plotted (±median absolute deviation) for B cell, T cell, NK cell, Neutrophil, Monocyte and Dendritic cells. Control—left of vertical dividing line, bacterial infected—right of vertical dividing line.
Figure 15:
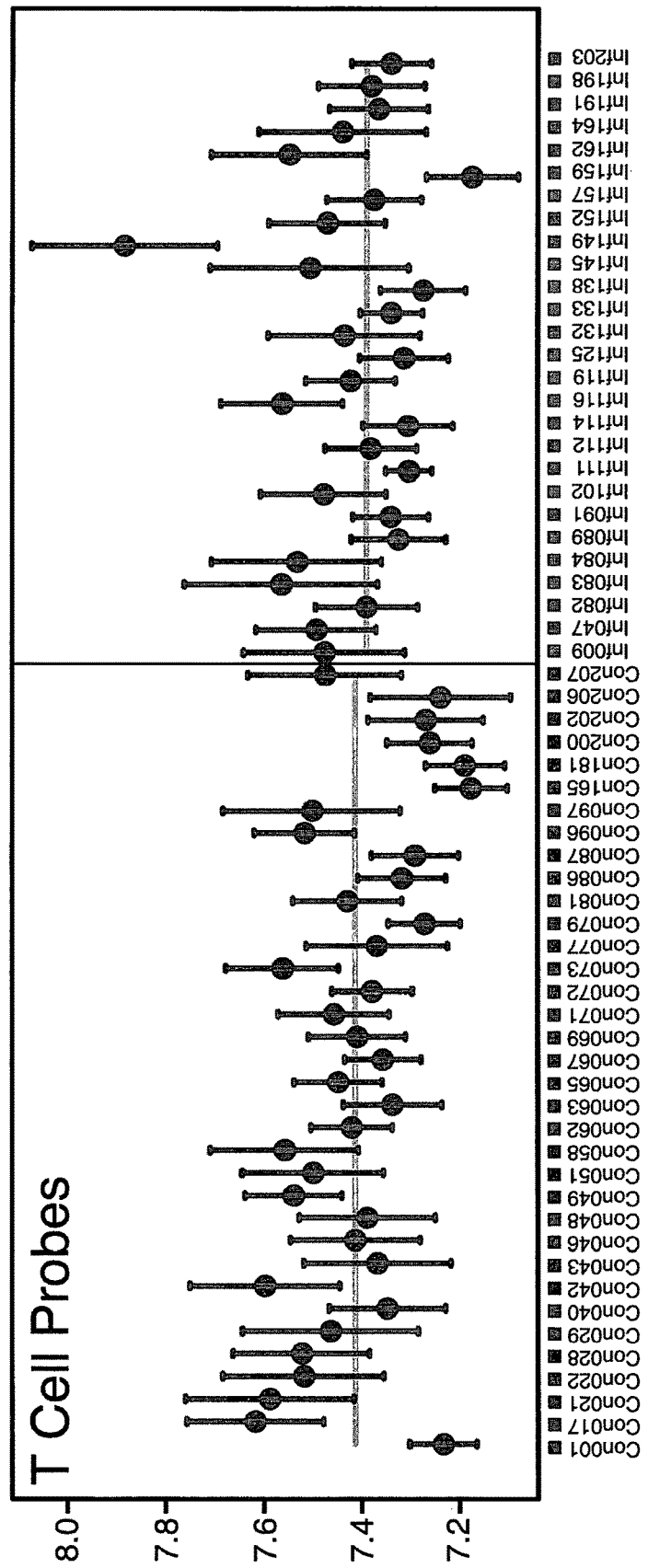
Figure 15:
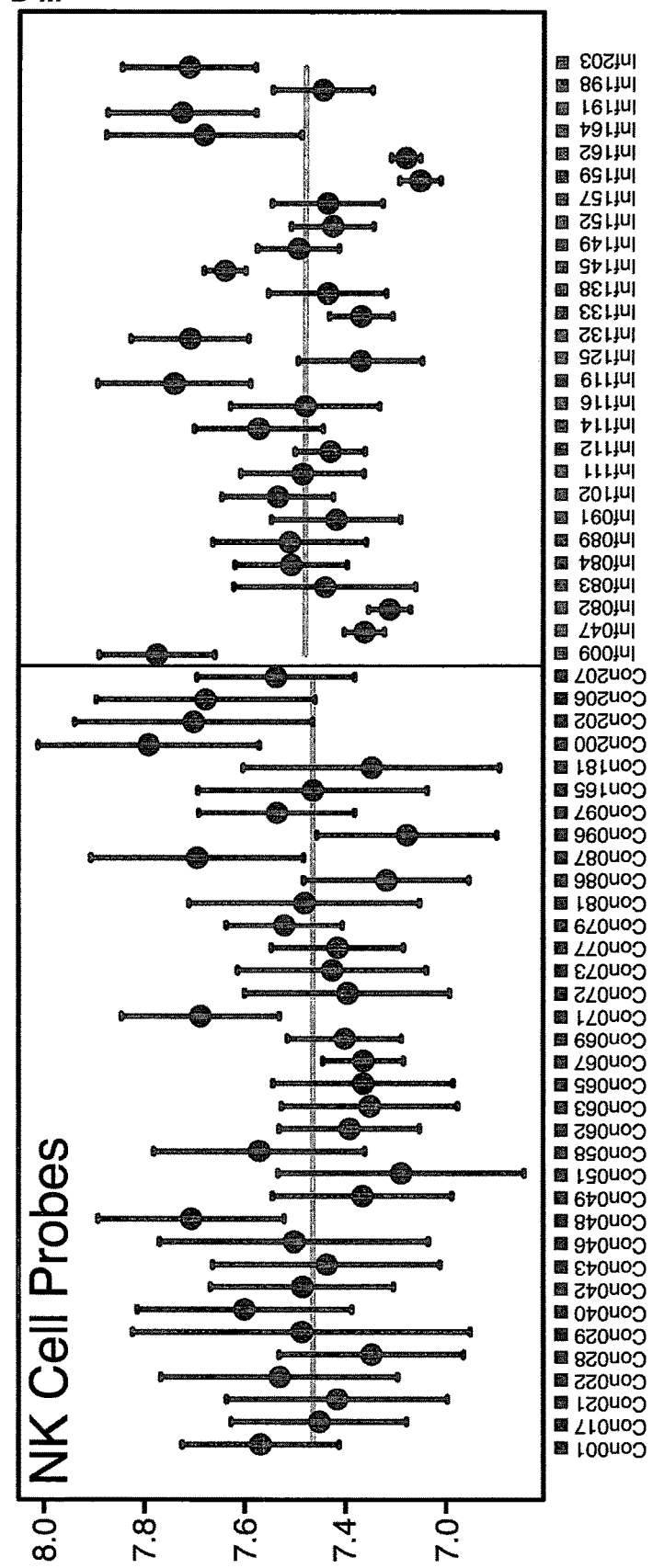
Figure 15:
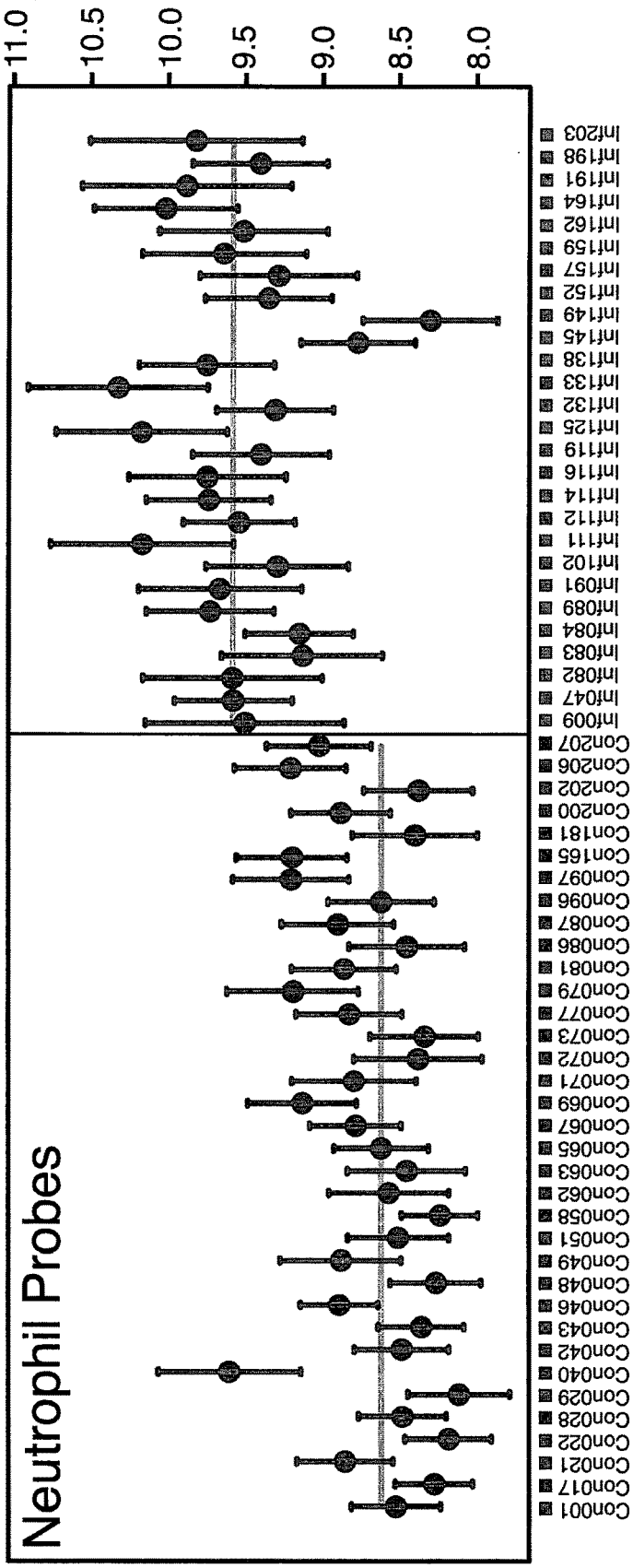
Figure 15:
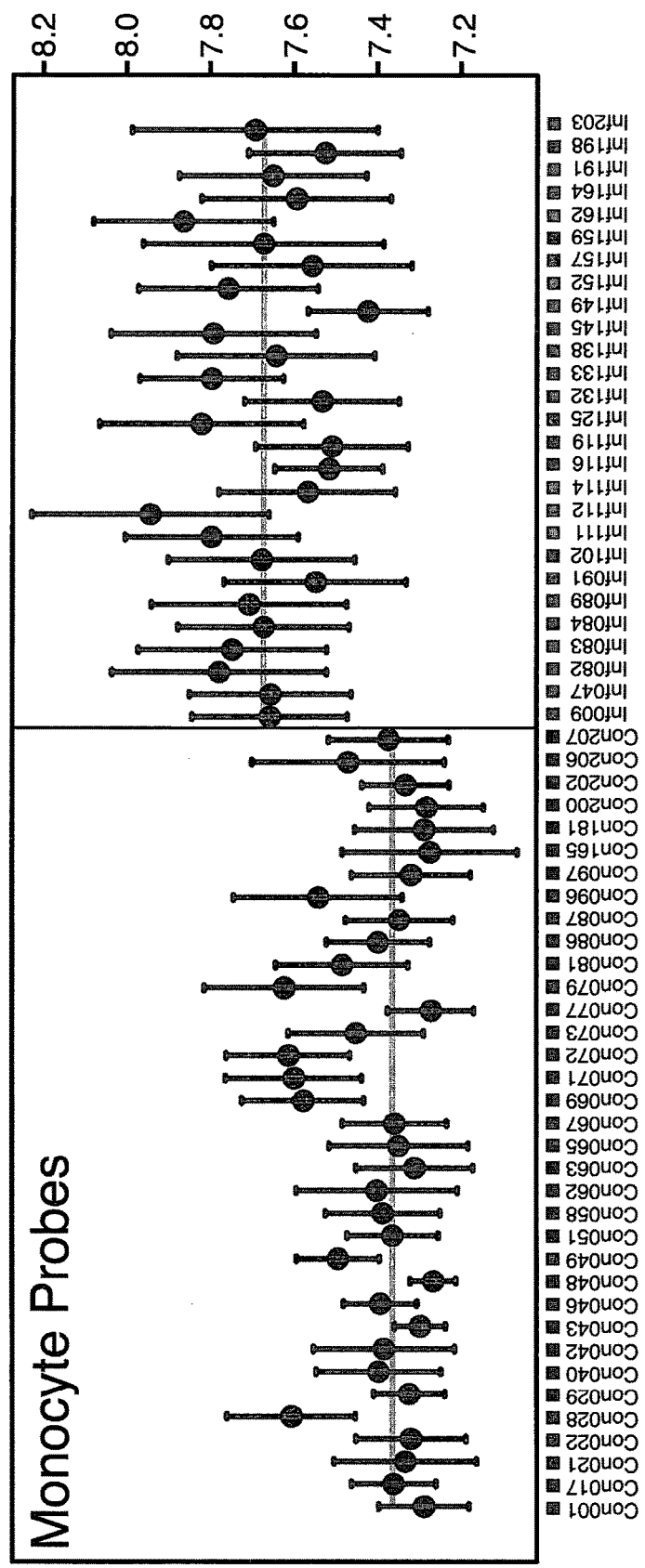
Figure 15:
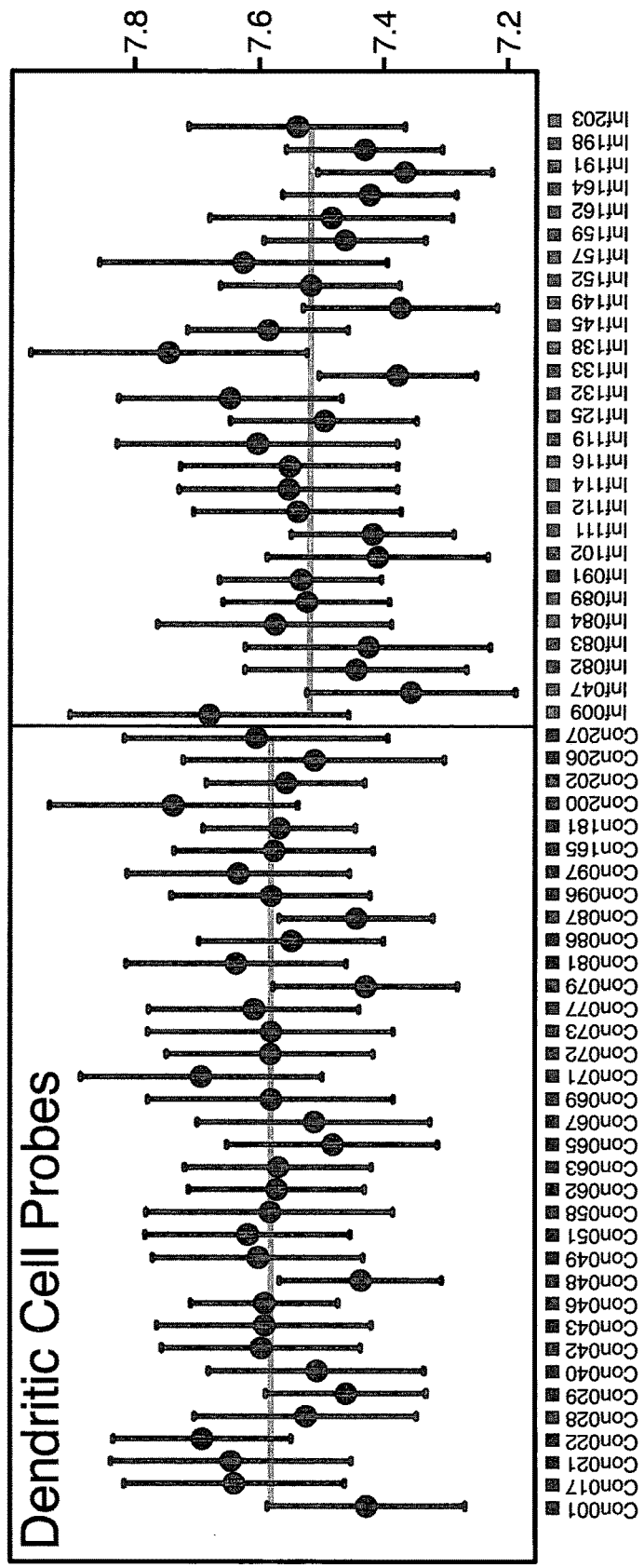

A central issue is whether specific host networks associated with infection are developed and uniformly present across all patients. Indeed, we might anticipate that individual patients will have different responses. To examine this issue we applied a data-driven approach for determining networks of co-expressed RNAs that are exclusive to infected infants. For these investigations we evaluated the linear dependence of the 824 statistically significant gene probes and used a Markov Cluster Algorithm (MCL) for revealing correlated probes amongst patient samples using the BioLayout tool (Theocharidis et al., *Nature protocols* 4, 1535-1550 (2009)). It should be pointed out that these analyses have a degree of subjectivity based on the clustering parameters chosen for visually discerning discrete clusters termed "cliques" and these will vary in size and degree of connectivity dependent on the parameter settings. Nevertheless, this approach is optimal for exploring a data-driven assignment of highly co-regulated genes with the infected cases. FIG. 15a & b show the developed network modules of co-expressed genes from the data using parameter cut-offs of Pearson correlation r=0.78 and MCL Inflation value of 4 and Pre-inflation value of 3. In this network analysis, 12 discernible co-expressed networks are observed to be strictly associated with infection and post-hoc pathway analysis shows each corresponding to a defined biological process (FIG. 15b).

Patient specific expression profiles of networks of 824 statistically differentially expressed probes (adj.p≤1.01, fold change ≥2) were visualised using BioLayout Express 3D. Clusters of co-expressed genes within networks were then defined by applying a Markov clustering (MCL) expansion value of 4. Twelve clusters of genes that exhibit discernible responses in the infected patient group show that even within the infected group there are differences in expression levels for a given cluster of genes, illustrating individual patient response. The top canonical pathways associated with these clusters are as follows (p-values shown in brackets): 01—Interferon Signalling ($6.27 \times 10^{-8}$), Activation of IRF by Cytosolic Pattern Recognition Receptors ($2.46 \times 10^{-3}$), Role of Pattern Recognition Receptors in Recognition of Bacteria and Viruses ($3.62 \times 10^{-3}$), Communication between Innate and Adaptive Immune Cells ($3.72 \times 10^{-3}$), Pathogenesis of Multiple Sclerosis ($1.1 \times 10^{-2}$), 02—Glycolysis/Gluconeogenesis ($2.51 \times 10^{-3}$), Differential Regulation of Cytokine Production in Intestinal Epithelial Cells by IL-17A and IL-17F ($2.13 \times 10^{-2}$), Pentose Phosphate Pathway ($2.68 \times 10^{-2}$), Urea Cycle and Metabolism of Amino Groups ($2.86 \times 10^{-2}$), Nitrogen Metabolism ($3.13 \times 10^{-2}$), Cluster 03—IL-8 Signaling ($5.93 \times 10^{-3}$), Methane Metabolism ($1.03 \times 10^{-2}$), Stilbene, Coumarine and Lignin Biosynthesis ($1.23 \times 10^{-2}$), Phenylalanine Metabolism ($2.45 \times 10^{-2}$), TREM1 Signaling ($3.46 \times 10^{-2}$), 04—Role of Macrophages, Fibroblasts and Endothelial Cells in Rheumatoid Arthritis ($1.26 \times 10^{-11}$), NF-kB Signalling ($4.77 \times 10^{-8}$), IL-10 Signalling ($6.16 \times 10^{-8}$), 38 MAPK Signalling ($1.35 \times 10^{-7}$), Acute Phase Response Signalling ($7.61 \times 10^{-7}$), 05—iCOS-iCOSL Signaling in T Helper Cells ($1.45 \times 10^{-5}$), Cytotoxic T Lymphocyte-mediated Apoptosis of Target Cells ($3.81 \times 10^{-5}$), OX40 Signaling Pathway ($5.31 \times 10^{-5}$), Systemic Lupus Erythematosus Signaling ($1.34 \times 10^{-4}$), Regulation of IL-2 Expression in Activated and Anergic T Lymphocytes ($2.1 \times 10^{-4}$), 06—Pathogenesis of Multiple Sclerosis ($2.66 \times 10^{-3}$), Role of PKR in Interferon Induction and Antiviral Response ($1.18 \times 10^{-2}$), Role of Hypercytokinemia/hyperchemokinemia in the Pathogenesis of Influenza ($1.21 \times 10^{-2}$), IL-10 Signaling ($1.99 \times 10^{-2}$), Fcγ Receptor-mediated Phagocytosis in Macrophages and Monocytes ($2.66 \times 10^{-2}$), 07—EIF2 Signaling ($1.66 \times 10^{-2}$), 08—Glioma Invasiveness Signaling ($1.64 \times 10^{-2}$), Aminosugars Metabolism ($1.96 \times 10^{-2}$), IL-17 Signaling ($2.11 \times 10^{-2}$), Hepatic Fibrosis/Hepatic Stellate Cell Activation ($3.98 \times 10^{-2}$), Germ Cell-Sertoli Cell Junction Signaling ($4.49 \times 10^{-2}$), 09—Pentose Phosphate Pathway ($1.96 \times 10^{-5}$), Inositol Metabolism ($1.23 \times 10^{-3}$), Fructose and Mannose Metabolism ($1.05 \times 10^{-2}$) Glutathione Metabolism ($1.27 \times 10^{-2}$), Glycolysis/Gluconeogenesis ($1.95 \times 10^{-2}$), 10—Eicosanoid Signaling ($1.12 \times 10^{-2}$), Caveolar-mediated Endocytosis Signaling ($1.39 \times 10^{-2}$), TR/RXR Activation ($1.66 \times 10^{-2}$), Paxillin Signaling ($1.92 \times 10^{-2}$), Arachidonic Acid Metabolism ($1.94 \times 10^{-2}$), 11—B Cell Development ($4.01 \times 10^{-6}$), FcγRIIB Signaling in B Lymphocytes ($1.19 \times 10^{-5}$), Altered T Cell and B Cell Signaling in Rheumatoid Arthritis ($4.13 \times 10^{-5}$), p70S6K Signaling ($1.03 \times 10^{-4}$), PI3K Signaling in B Lymphocytes ($1.16 \times 10^{-4}$), and 12—Starch and Sucrose Metabolism ($1.25 \times 10^{-2}$), Fcγ Receptor-mediated Phagocytosis in Macrophages and Monocytes ($1.78 \times 10^{-2}$), fMLP Signaling in Neutrophils ($2.09 \times 10^{-2}$), Pyrimidine Metabolism ($2.61 \times 10^{-2}$), Production of Nitric Oxide and Reactive Oxygen Species in Macrophages ($3.44 \times 10^{-2}$).

These networks are in good agreement with the pathway biology investigations described in the previous section but clearly reveal an underlying heterogeneity in terms of an individual patient's response to infection. For example cluster 01 defines a specific type I IFN sub-network (and it is worth noting that the type II IFN responsive gene CXCL10 is a key member of this network suggesting redundant cross-talk between Type I and II signalling). Type I IFN signalling can in some cases be detrimental for individuals with bacterial infections contributing to pathogenesis of infection (Decker et al., *Nat Rev Immunol* 5, 675-687 (2005)). In the patient cases exhibiting cluster 01 we cannot rule out that those patients showing a type I IFN response may also be virally infected. Cluster 02 consists of a network associated with energy metabolism while cluster 03 represents an IL-8/neutrophil anti-microbial network. Statistical association of the 12 networks with 23 clinical parameters was investigated and summarized in FIG. 15*c* showing a limited number of associations with only cluster 04 lacking any statistical association. Death was weakly associated with clusters 03 and 02; while sugar levels were associated with clusters 01 and 06. The association with cluster 01 is not obvious and may be indicative of IFN regulation of glycolysis while cluster 06 consists of members associated with glycerol uptake and metabolism and also has an association with ventilation requirement. Clusters 05 and 02 have a gender bias while none of the clusters are associated with gestational age. Not surprisingly the most common association is with neutrophils and clusters 01, 05, 06, 11 and 12. It should be considered that the overall sample size for these associations is small and will require further validation studies.

The inter-patient variability observed for these networks is both qualitatively and quantitatively high and therefore limits their utility as a host-directed infection signal. Further heterogeneity is also observed in inter-patient responses for specific immune cell compartments (FIG. 6*d*). For instance while most sepsis cases show high levels of neutrophil markers a small subset have levels commensurate with neutropenia. Thus an examination of the cellular compartments alone is also insufficiently uniform. It is particularly noteworthy that this is in marked contrast to the 52-gene dual-network identified using feature selection procedure based on statistical and pathway information alone (FIG. 11*a*) which appears to be more uniformly representative of a patient-invariant infection response. Moreover there are no significant confounding associations with any of the 23 clinical parameters tested.

EXAMPLE 9

Specificity and Validation of the 52-gene Dual-network as a Classifier of Neonatal Infection With the expectation that the 52-gene dual-network might perform well as a classifier, we set out to evaluate further its specificity for infection response using four distinct machine learning algorithms; random forest, support vector machine, k-nearest neighbour and receiver operator characteristics (ROC) for classification. To assess the performance of each algorithm with respect to node performance we estimated the generalisation error (that measures how well a learning algorithm performs in new and unseen data) using a replicated leave-one-out cross validation approach. We replicated the cross-validation algorithm 100 times to average out any variation in the error estimates resulting from the randomness involved in the cross-validation procedure while splitting the dataset into training and test sets at each step. FIG. 16*a* shows the average leave-one-out error rate over 100 replications as a performance measure with biomarkers listed sequentially. When the number of genes included was between 4 and 19 the error rate was between 0 and 2%. When 19 or more markers were included the error rate was consistently 0% with all four machine-learning methods tested, thus confirming internal consistency of the selected gene set as a classifier. Pleasingly, this number of network genes is in good agreement with the estimated optimal number of biomarkers from our previous predictive in silico simulation studies (Khondoker et al., *Journal of Bioinformatics and Computational Biology* 08, 945-965 (2010). For further testing of our 52-gene marker set we proceeded with the ROC-based classifier, as this does not require any tuning of parameters and simplifies classification to a univariate decision that can easily be applied to independent test sets. An analysis of the individual pathways using the ROC based classifier provided an accuracy of 84% for innate markers, 65% for the adaptive markers and 74% with the metabolic markers; while all three pathway markers combined gave an enhanced accuracy of 98% (sensitivity=100%, specificity=97%). Hence, combination of the three pathways provides an optimally robust classifier.

Next, replication and validation of the classifier on different microarray platforms and patient samples that were not part of the original gene selection process was subsequently performed (FIG. 16*b* and FIG. 5). In our platform test set, we used 42 existing patient samples (18 infected, 24 controls) for 48 (matched) genes with a completely different microarray platform. A ROC classifier based on the training set when applied to this platform correctly assigned 100% of samples to control or bacterially infected groups (sensitivity=100%, specificity=100%).

In our validation test set, we used a new and independent set of 26 samples (16 infected, 10 controls) that were analysed on three different microarray platforms. ROC-classification based on the training set when applied to the new validation test set correctly assigned 100% of samples to control or bacterially infected groups with sensitivity=100% and a specificity=100%. Notably, a further three virally infected samples classified as control and align with control samples in hierarchical clustering (FIG. 16*c*). These results are in agreement with the CMV infected case shown in FIG. 10 that is also not recognized by the dual-network and also clustered with the controls and not bacterially infected samples. We next sought to compare the outcome of the 52-gene dual-network with other recently published host protein biomarkers (CD69 and FGCR1A) of neonatal sepsis reporting 100% sensitivity and 22-44% specificity (Labib et al., *International Journal of Microbiological Research* 4, 77-85 (2013)). It is worth noting that FGCR1A is also a member of the 52-gene dual-network classifier. For this purpose we tested whether expression levels of CD69 and FGCR1A (CD64) would predict infection on the Illumina training set. The LOOCV analysis of these markers at the RNA level developed 74% sensitivity with 91% specificity with an overall accuracy of 84%. While these results show the potential use of these markers they clearly exhibit sensitivity values less than specificity and have reduced accuracy in comparison with the dual network classifier.

The most pressing clinical need, however, is to identify bacterial infection in individuals that are suspected to have infection at the first time of symptoms developing, who subsequently have negative bacterial cultures. To explore this possibility we selected a completely new group of 30 patients that were suspected of being infected at the time of sample collection but that had blood culture negative test results. When the receiver operator characteristic based classification algorithm was applied to this suspected infected test set it assigned 17 of the 30 patient samples to the bacterially infected group (FIG. 16d). Subsequent expert assessment based on clinical criteria indicated 6 infected and 16 not infected (FIG. 16di) with 9 where a clinical categorization could not confidently be made (FIG. 16diii). Concordance between classifier prediction and expert opinion for the infected and non-infected was tested as moderate (Cohen's kappa k=0.24, in relation to the empirically achievable k=0.46) (FIG. 16dii) and comparison of classifier predicted infection with expert assessment showed good agreement with statistically significant differences in days on antibiotics and neutrophil count between classified control and infected suspected samples (FIG. 16e). These findings highlight the difficulty faced by clinicians in determining cases of blood culture negative sepsis and strongly support the possible future clinical utility of the classifier assessed in a cross-sectional study. Altogether, we conclude that the 52-gene dual-network has excellent efficacy at identifying bacterial infection with very high sensitivity and specificity.

EXAMPLE 10

The 52-gene Dual-network is Robust Against Gestational Age

These results support the possibility of using the 52-gene dual-network as a classifier for bacterial infection. However, when considering the demographic data it is evident that there is a difference in mean corrected gestational age of infected and control groups. Hence it is important to be sure that the differences observed in gene expression of the 52-genes in the dual network between control and infected groups are not a reflection of differing maturity of the immune system. We therefore examined our classifier gene set further by looking at gene expression within groups according to gestational age. Notably we find there is no statistical difference in gene expression of the 52-gene dual-network between infants of differing gestational ages (Table 6). Therefore in this study group the 52-gene dual-network trait is robust against variation across gestational ages. It is also noteworthy that although overall a statistically significant increase in neutrophils is detected (FIG. 12d); the dual-network is also reliable in stratifying infected infants who had neutropenia. This observation further strengthens the proposition of using a unified trait of networks of highly connected genes rather than individual genes for a classifier.

Table 6 shows statistical testing of the effect of gestational age on gene expression during neonatal sepsis. Within each sample group (control, infected), samples were age-classified into bins based on the 33% and 66% corrected gestational age quantile values, yielding three age-groupings (Young, Mid, Old). Corrected gestational ages for age-groupings were—Young control <279, Mid control 279-293, Old control >293, Young infected <209, Mid infected 209-222 and Old infected >222. Pair-wise comparisons of Old vs Young and Old vs Mid groupings were performed using eBayes and the number of significant loci (adj.p≤0.5) are shown in the table. Genes differentially regulated were—Old vs Mid Infected (POTEA & POTEG), Old vs Young Infected (POTEA, POTEG, A4GNT, AAAS & AACS) and Old vs Young Control (POTEA, POTEG, A4GNT, AAAS, AACS, NCEH1, AAK1 & AAMP). None of these genes were significantly differentially expressed between infected and control samples.

TABLE 6

|  | Control | Infected |
|---|---|---|
| Old vs Young | 10 | 5 |
| Old vs Mid | 0 | 2 |

EXAMPLE 11

Combinatorial Analysis

Figure 17:
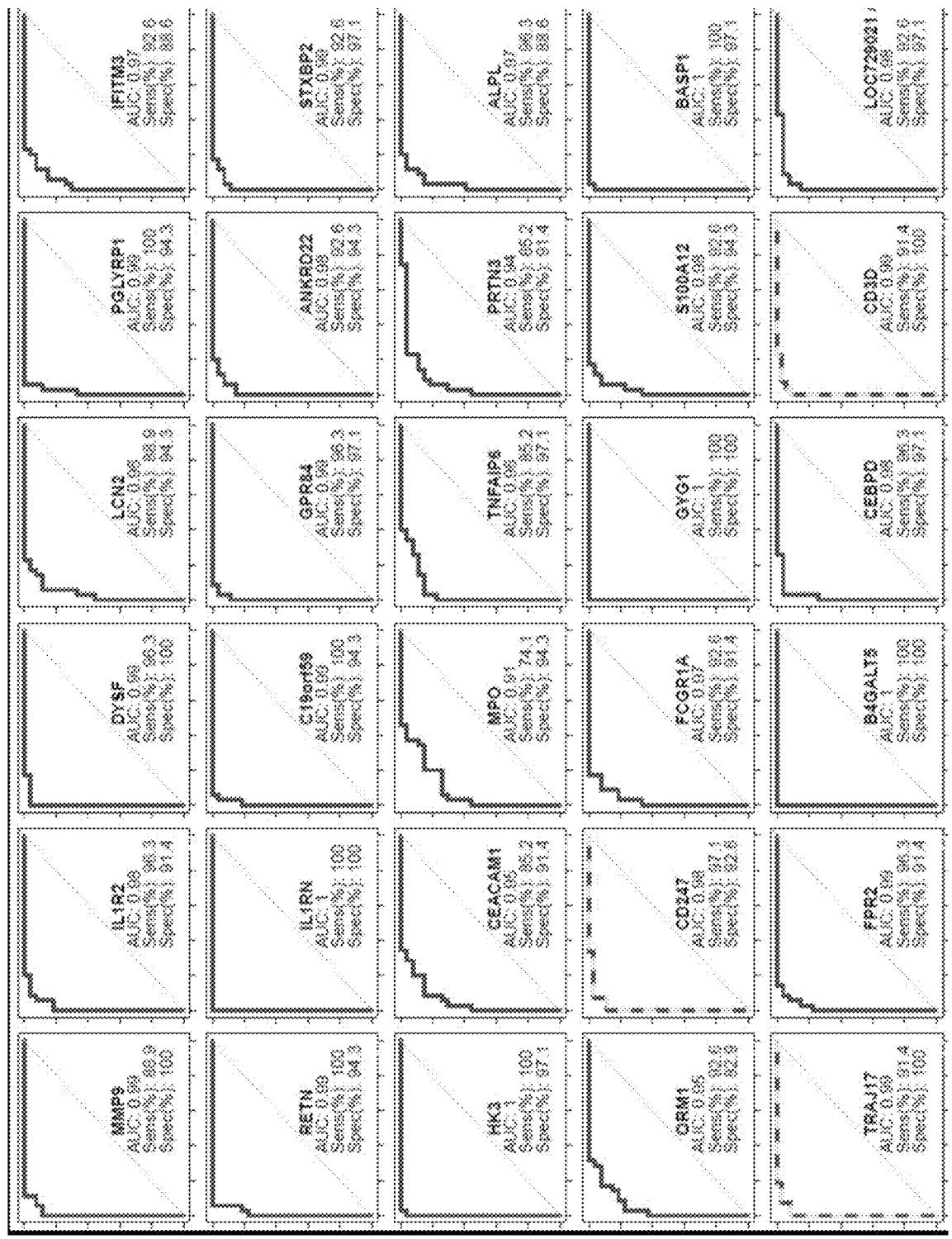
FIG. 17 shows the results of ROC analysis conducted for each individual gene performed to select the most accurate biomarkers in predicting sepsis in neonates. Abbreviations are as follows; AUC, Area Under Curve; Sens(%), Sensitivity; Spec(%), Specificity.
Figure 17:
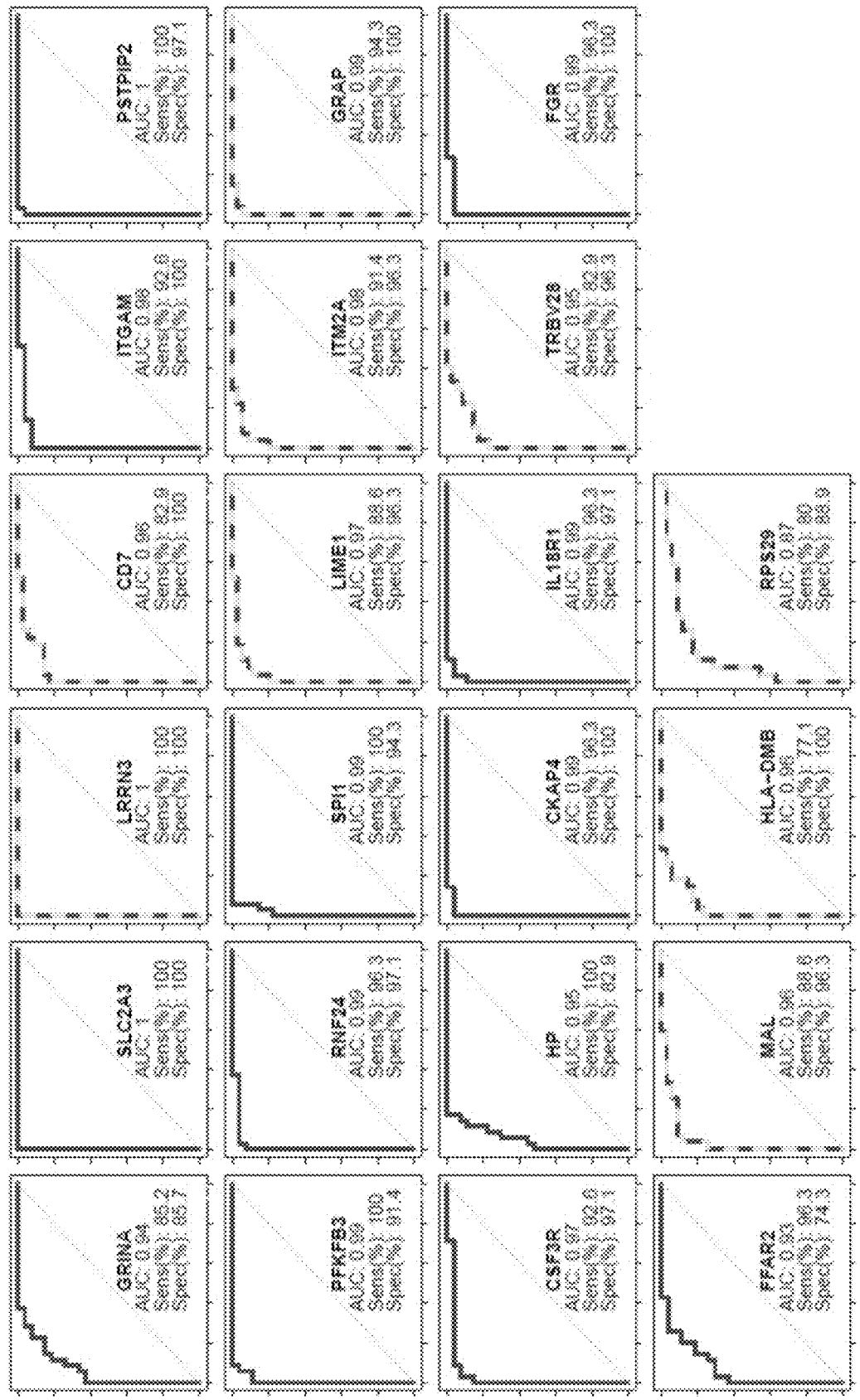

Combinations of biomarkers of the 52-gene dual-node network, within and between pathways were analysed for their detection accuracy in predicting sepsis in neonates in two steps. (1) Starting with the 62 samples referred to as the 'training set' (all processed and log2 transformed data), we applied a ROC analysis for each individual gene. (1a) For the given gene, the lowest expression value was taken from amongst its 62 measurements, and referred to as the current threshold delta. (1b) All samples for which this gene's expression measurement falls below delta were classed as "non-sepsis" (for the minimum value this would be zero), and all that fall above delta as "sepsis" (for the minimum expression value, all samples would be classed as sepsis cases). (1c) Assigned classes were compared against the actual known class, i.e. sensitivity and specificity for the current delta were obtained. The preceding steps (1a-1c) were repeated with the next lowest expression value from amongst the given gene's measurements until the maximum expression value for the gene was arrived at. Finally, from the sensitivity and specificity data collected for each delta, ROC curves for each gene were constructed (FIG. 17).

Figure 18:
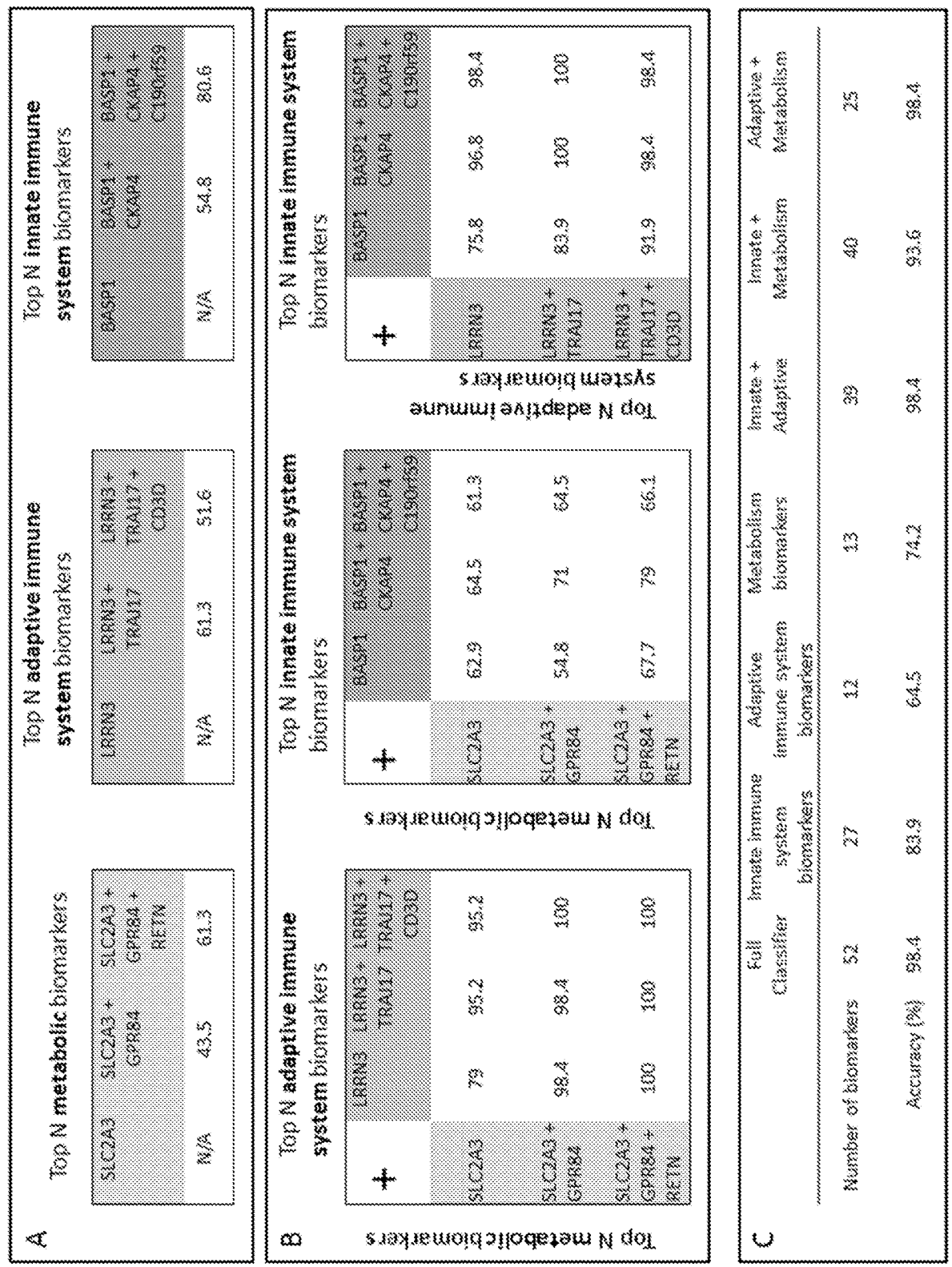
FIG. 18 shows the identification of the top 3 biomarkers for each pathway based on their individual ROC performance as measured by area under the curve AUC (i.e. how well the individual gene distinguishes between control and infected neonates). Only those genes where the prediction is for bacterial infection (rather than viral infection) were retained for subsequent analyses. All tables in the figure show classification accuracy (%) of the classifier in a leave-one-out cross-validation (LOOCV) test. Panel A gives the classification accuracy for the top 2 and top 3 genes of each pathway (classification with data scaling to the mean). Panel B shows the results of a combinatorial ROC analysis indicating the classification accuracy when genes from different pathways are combined. For example when the top two metabolic pathway genes (SLC2A3 and GPR84) are analysed in combination with the top two adaptive immunity pathway genes (LRRN3 and TRAJ17), those 4 genes in concert provide a sepsis classification accuracy of 98.4%. Panel C gives the classification accuracy for the full classifier gene set of 52 genes, as well as full pathways and combinations of full pathways.

In a second step, biomarkers of the 52 marker set which were found to be differentially expressed relative to controls during influenza infection were removed from the analysis and only those genes where the prediction was for bacterial infection (rather than viral infection) were retained for subsequent analyses. FIG. 18 shows the identification of the top 3 biomarkers for each pathway based on their individual ROC performance as measured by area under the curve AUC (i.e. how well the individual gene distinguishes between control and infected neonates).

Classification accuracy (%)(shown in all panels) of the classifier was determined by a leave-one-out cross-validation (LOOCV) test. Panel A gives the classification accuracy for the top 2 and top 3 genes of each pathway (classification with data scaling to the mean). Panel B shows the results of a combinatorial ROC analysis indicating the detection accuracy when genes from different pathways are combined. When the top two metabolic pathway genes (SLC2A3 and GPR84) are analysed in combination with the top two adaptive immunity pathway genes (LRRN3 and TRAJ17), those 4 genes in concert provide a sepsis classification accuracy of 98.4%. When the top two metabolic pathway genes (SLC2A3 and GPR84) are analysed in combination with the top three adaptive immunity pathway genes (LRRN3, TRAJ17 and CD3D), those 5 genes in concert provide a sepsis classification accuracy of 100%. Additionally, when the top three metabolic pathway genes (SLC2A3, GPR84 and RETN) are analysed in combination with the top two adaptive immunity pathway genes (LRRN3 and TRAJ17), those 5 genes in concert provide a sepsis classification accuracy of 100%.

A combination of the top two innate immunity pathway genes (BASP1 and CKAP4) with the top two adaptive immunity pathway genes (LRRN3 and TRAJ17), provides a sepsis classification accuracy of 100%. Furthermore when the top two innate immunity pathway genes (BASP1 and CKAP4) are analysed in combination with the top three adaptive immunity pathway genes (LRRN3, TRAJ17 and CD3D), those 5 genes in concert provide a sepsis classification accuracy of 98.4%. Additionally, when the top three innate immunity pathway genes (BASP1, CKAP4 and C19orf59) are analysed in combination with the top two adaptive immunity pathway genes (LRRN3 and TRAJ17), those 5 genes in concert provide a sepsis classification accuracy of 100%.

Panel C gives the classification accuracy for the full classifier gene set of 52 genes, as well as full pathways and combinations of full pathways. Use of biomarkers from any of the pathways in combination gives a classification accuracy of over 93.6%. The results support the possibility of using combinations of biomarkers from the 3 pathways as classifiers for bacterial infection.

Tables 7-11 show clinical criteria assessed in study samples.

TABLE 7

| Study no. | Study Category | Same Baby | Maternal risk factor(s) present | Mode of delivery | Gestation at birth (completed weeks) | Postnatal age at sample (completed days) | Sex | Ethnicity |
|---|---|---|---|---|---|---|---|---|
| csb002 | possible | . | O | vaginal | 41 | 1 | girl | asian |
| csb005 | possible | . | O | vaginal | 25 | 68 | boy | caucasian |
| csb008 | possible | . | O | section | 33 | 0 | girl | caucasian |
| csb009 | infected | . | O | section | 28 | 33 | girl | caucasian |
| csb010 | possible | . | O | section | 38 | 0 | boy | caucasian |
| csb011 | possible | . | X | vaginal | 35 | 0 | girl | caucasian |
| csb012 | infected | . | O | section | 34 | 6 | girl | caucasian |
| csb013 | possible | . | O | section | 40 | 0 | boy | mixed |
| csb019 | possible | . | X | section | 29 | 0 | girl | caucasian |
| csb020 | possible | . | X | section | 34 | 0 | girl | caucasian |
| csb024 | possible | . | O | section | 34 | 0 | boy | caucasian |
| csb025 | possible | . | O | section | 34 | 0 | boy | caucasian |
| csb026 | possible | . | X | vaginal | 35 | 0 | boy | caucasian |
| csb027 | possible | . | O | section | 41 | 0 | boy | asian |
| csb032 | infected | . | O | vaginal | 40 | 8 | girl | caucasian |
| csb033 | possible | . | O | section | 35 | 0 | boy | caucasian |
| csb034 | possible | . | O | vaginal | 29 | 0 | girl | caucasian |
| csb035 | possible | . | O | vaginal | 41 | 1 | boy | caucasian |
| csb036 | possible | . | X | vaginal | 41 | 0 | girl | caucasian |
| csb037 | possible | . | O | section | 26 | 32 | boy | caucasian |
| csb038 | possible | . | X | section | 29 | 0 | boy | caucasian |
| csb039 | possible | . | X | section | 29 | 0 | boy | caucasian |
| csb041 | possible | . | O | vaginal | 29 | 4 | boy | caucasian |
| csb044 | possible | . | O | section | 36 | 0 | boy | caucasian |
| csb047 | infected | . | O | vaginal | 29 | 12 | boy | caucasian |
| csb053 | possible | . | X | vaginal | 35 | 0 | girl | hispanic |
| csb054 | possible | . | O | vaginal | 37 | 0 | girl | caucasian |
| csb055 | possible | . | X | vaginal | 41 | 1 | girl | caucasian |
| csb057 | possible | . | O | vaginal | 37 | 0 | girl | afrocaribbean |
| csb059 | possible | . | X | section | 41 | 1 | boy | not stated |
| csb061 | possible | . | X | vaginal | 30 | 9 | girl | not stated |
| csb064 | possible | . | X | vaginal | 26 | 4 | girl | not stated |
| csb068 | possible | . | O | section | 40 | 1 | boy | not stated |
| csb074 | possible | . | X | section | 34 | 0 | girl | not stated |
| csb075 | infected | 70 | X | vaginal | 26 | 74 | girl | caucasian |
| csb082 | infected | | O | section | 29 | 8 | boy | caucasian |
| csb083 | infected | | O | vaginal | 29 | 36 | girl | not stated |
| csb084 | infected | 116 | O | section | 28 | 10 | boy | caucasian |
| csb089 | infected | | X | section | 27 | 9 | boy | not stated |
| csb091 | infected | | X | vaginal | 38 | 1 | girl | caucasian |
| csb102 | infected | 103 | O | section | 27 | 31 | girl | not stated |
| csb107 | infected | 108, 110 | O | vaginal | 23 | 8 | boy | not stated |
| csb111 | infected | 115 | X | section | 28 | 14 | boy | caucasian |
| csb112 | infected | 124, 129, 130 | X | vaginal | 24 | 10 | girl | Oriental |
| csb114 | infected | 99 | X | vaginal | 26 | 9 | girl | caucasian |
| csb116 | infected* | 84 | O | section | 28 | 14 | boy | caucasian |
| csb118 | infected | 120, 122 | O | section | 29 | 59 | boy | caucasian |
| csb119 | infected | 125 | O | section | 28 | 16 | girl | not stated |
| csb125 | infected | 119 | O | section | 28 | 12 | girl | not stated |
| csb132 | infected | 131, 145 | O | vaginal | 27 | 16 | boy | not stated |
| csb133 | infected | | X | vaginal | 27 | 4 | boy | not stated |
| csb137 | infected | | X | section | 29 | 43 | boy | caucasian |
| csb138 | infected | | O | vaginal | 16 | 16 | girl | caucasian |
| csb145 | infected | 131, 132 | O | vaginal | 27 | 12 | boy | not stated |
| csb149 | infected | 148, 151, 155 | O | section | 27 | 16 | girl | caucasian |
| csb152 | infected | | O | section | 28 | 21 | boy | caucasian |
| csb155 | infected | 148, 149, 151 | O | section | 27 | 10 | girl | caucasian |
| csb157 | infected | 158, 164, 167 | O | section | 28 | 24 | girl | caucasian |
| csb159 | infected | | O | section | 30 | 9 | boy | caucasian |

TABLE 7-continued

| Study no. | Study Category | Same Baby | Maternal risk factor(s) present | Mode of delivery | Gestation at birth (completed weeks) | Postnatal age at sample (completed days) | Sex | Ethnicity |
|---|---|---|---|---|---|---|---|---|
| csb161 | infected | | ○ | section | 28 | 9 | boy | caucasian |
| csb162 | infected | 156 | X | section | 27 | 6 | boy | asian |
| csb164 | infected | 157, 158, 167 | ○ | section | 28 | 26 | girl | caucasian |
| csb191 | infected | | X | vaginal | 37 | 0 | boy | caucasian |
| csb198 | infected | 175, 185, 203 | X | section | 32 | 8 | boy | caucasian |
| csb203 | infected | 175, 185, 198 | X | section | 32 | 35 | boy | not stated |
| csb216 | infected | | ○ | vaginal | 25 | 66 | girl | not stated |
| csb226 | infected | | ○ | section | 29 | 30 | boy | not stated |
| csb239 | infected | | ○ | section | 27 | 5 | boy | not stated |
| csb253 | infected (timing) | | ○ | section | 30 | 44 | girl | not stated |
| csb262 | infected | | ○ | vaginal | 24 | 111 | girl | caucasian |
| csb267 | infected | 271 | ○ | section | 29 | 50 | boy | not stated |
| csb269 | infected | | ○ | section | 35 | 5 | boy | not stated |
| csb271 | infected | 267 | ○ | section | 29 | 48 | boy | not stated |
| csb275 | infected | | ○ | section | 28 | 77 | boy | not stated |
| csb278 | infected | 279 | ○ | vaginal | 24 | 58 | boy | not stated |
| csb283 | infected* | 297, 299, 286 | ○ | section | 30 | 12 | boy | not stated |
| csb287 | infected | | X | vaginal | 26 | 62 | girl | not stated |
| csb297 | infected | 283, 299 | ○ | section | 30 | 39 | boy | not stated |
| csb299 | infected | 283, 296 | ○ | section | 30 | 44 | boy | not stated |

TABLE 8

| Study no. | Organism | Site | Other | Early or late onset infection | Sample in relation to blood culture | Duration of Antibiotics (days) | Respiratory distress | Apnoeas, Increased oxygen requirement or increased ventilatory support |
|---|---|---|---|---|---|---|---|---|
| csb002 | | | | | 0 | 3 | ○ | ○ |
| csb005 | | | | | 0 | 6 | X | X |
| csb008 | | | | | 0 | 5 | X | X |
| csb009 | coagulase negative staphylococcus | blood | | late | 0 | 14 | X | X |
| csb010 | | | | | 0 | 5 | X | X |
| csb011 | | | | | 0 | 5 | X | ○ |
| csb012 | enterovirus | csf | | late | 0 | 10 | X | ○ |
| csb013 | | | | | 0 | 2 | X | ○ |
| csb019 | | | | | 0 | 3 | ○ | ○ |
| csb020 | | | | | 0 | 3 | ○ | ○ |
| csb024 | | | | | 0 | 2 | X | ○ |
| csb025 | | | | | 0 | 2 | X | ○ |
| csb026 | | | | | 0 | 5 | X | X |
| csb027 | | | | | 0 | 5 | ○ | ○ |
| csb032 | listeria monocytogenes | csf | | late | 0 | 14 | ○ | ○ |
| csb033 | | | | | 0 | 5 | X | ○ |
| csb034 | | | | | 0 | 5 | X | ○ |
| csb035 | | | | | 0 | 4 | X | ○ |
| csb036 | | | | | 0 | 0 | ○ | ○ |
| csb037 | | | | | 0 | 0 | X | X |
| csb038 | | | | | 0 | 0 | ○ | ○ |
| csb039 | | | | | 0 | 0 | ○ | ○ |
| csb041 | | | | | 0 | 2 | ○ | ○ |
| csb044 | | | | | 0 | 2 | X | ○ |
| csb047 | candida | blood | also klebsiella in peritoneal fluid | late | 0 | 7 | X | ○ |
| csb053 | | | | | 0 | 5 | X | X |
| csb054 | | | | | 0 | 2 | X | ○ |
| csb055 | | | | | 0 | 5 | X | ○ |
| csb057 | | | | | 0 | 2 | X | ○ |
| csb059 | | | | | 12 hours after | 5 | X | ○ |
| csb061 | | | | | 0 | 10 | ○ | ○ |
| csb064 | | | | | 0 | 12 | ○ | X |
| csb068 | | | | | 0 | 0 | ○ | ○ |
| csb074 | | | | | 0 | 5 | X | ○ |
| csb075 | CMV | blood, urine | | late | 0 | 3 | ○ | X |
| csb082 | enterobacter cloacae | | | late | 0 | 14 | ○ | X |

TABLE 8-continued

| Study no. | Organism | Site | Other | Early or late onset infection | Sample in relation to blood culture | Duration of Antibiotics (days) | Respiratory distress | Apnoeas, Increased oxygen requirement or increased ventilatory support |
|---|---|---|---|---|---|---|---|---|
| csb083 | enterococcus faecalis | blood | | late | 0 | 10 | ○ | X |
| csb084 | coagulase negative staphylococcus | blood | 2 cultures | late | 0 | 14 | ○ | ○ |
| csb089 | coagulase negative staphylococcus | blood | | late | 0 | 3 | ○ | X |
| csb091 | group B streptococcus | blood | | early | 0 | 5 | ○ | ○ |
| csb102 | pseudomonas aeuruginosa | blood | | late | 0 | 14 | ○ | ○ |
| csb107 | coagulase negative staphylococcus | blood | 2 cultures | late | 0 | 7 | ○ | ○ |
| csb111 | coagulase negative staphylococcus | | | late | 0 | 9 | ○ | X |
| csb112 | group B streptococcus | blood | | late | 0 | 11 | ○ | X |
| csb114 | coagulase negative staphylococcus | blood | | late | 0 | 11 | ○ | ○ |
| csb116 | coagulase negative staphylococcus | abscess | blood culture next day positive for coagulase negative staphlococcus | late | 0 | 14 | ○ | ○ |
| csb118 | coagulase negative staphylococcus | blood | | late | 0 | 10 | X | X |
| csb119 | coagulase negative staphylococcus | blood | | late | 0 | 18 | ○ | X |
| csb125 | coagulase negative staphylococcus | blood | | late | 0 | 18 | ○ | X |
| csb132 | enterococcus faecalis | blood | | late | 0 | 21 | ○ | X |
| csb133 | coagulase negative staphylococcus | blood | | late | 0 | 5 | ○ | X |
| csb137 | coagulase negative staphylococcus | blood | | late | 0 | 18 | ○ | X |
| csb138 | coagulase negative staphylococcus | blood | | late | 0 | 10 | ○ | X |
| csb145 | enterococcus faecalis | blood | | late | 0 | 21 | X | X |
| csb149 | Klebsiella | csf | | late | 0 | 25 | ○ | X |
| csb152 | coagulase negative staphylococcus | blood | | late | 0 | 15 | ○ | X |
| csb155 | Klebsiella pneumoniae | blood | | late | 0 | 25 | X | X |
| csb157 | coagulase negative staphylococcus | blood | | late | 8 | 16 | ○ | ○ |
| csb159 | enterococcus | blood | | late | 0 | 11 | X | ○ |
| csb161 | klebsiella oxytoca | blood and csf | | late | 0 | 23 | X | X |
| csb162 | coagulase negative staphylococcus | blood | 2 cultures | late | 0 | 5 | ○ | X |
| csb164 | klebsiella oxytoca | blood | | late | 0 | 16 | X | X |
| csb191 | e coli | blood | | early | 0 | 7 | X | ○ |
| csb198 | coagulase negative staphylococcus | blood | | late | 0 | 10 | X | X |
| csb203 | coagulase negative staphylococcus | blood | | late | 0 | 6 | X | X |
| csb216 | enterococcus | blood | | late | 0 | 16 | ○ | X |
| csb226 | enterococcus | blood | | late | 0 | 7 | ○ | X |
| csb239 | pseudomonas aeuruginosa | blood | | late | 0 | 2 days (until death) | ○ | X |
| csb253 | coagulase negative staphylococcus | blood | | late | 13 | 10 | ○ | ○ |
| csb262 | group B streptococcus | blood | | late | 0 | 13 | X | X |
| csb267 | candida | blood | | late | 0 | 8 | ○ | X |
| csb269 | CMV | blood, urine | | late | 4 days | 16 days antiviral therapy | ○ | ○ |
| csb271 | coagulase negative staphylococcus | blood | klebsiella 4 days previously in blood, candida 2 days later | late | 0 | 10 | ○ | X |
| csb275 | coagulase negative staphylococcus | blood | | late | 0 | 7 | ○ | ○ |

TABLE 8-continued

| Study no. | Organism | Site | Other | Early or late onset infection | Sample in relation to blood culture | Duration of Antibiotics (days) | Respiratory distress | Apnoeas, Increased oxygen requirement or increased ventilatory support |
|---|---|---|---|---|---|---|---|---|
| csb278 | rhinovirus | nasopharyngeal secretions | | late | 0 | 0 | ○ | ○ |
| csb283 | candida | peritoneal fluid | enterobacter blood 3 days earlier | late | 11 hours post op | 11 | ○ | ○ |
| csb287 | e coli | blood | | late | 0 | 13 | ○ | X |
| csb297 | serratia marcescens | blood | | late | 0 | 13 | ○ | X |
| csb299 | serratia marcescens | blood | | late | 0 | 13 | ○ | X |

TABLE 9

| Study no. | Bradycardias | Reduced perfusion, hypotension or fluid resuscitation | Temperature instability | Metabolic acidosis | Feed intolerance or abdominal concerns | Abnormal tone or irritability | Lethargy | Jaundice |
|---|---|---|---|---|---|---|---|---|
| csb002 | ○ | ○ | X | ○ | ○ | X | ○ | ○ |
| csb005 | X | ○ | ○ | ○ | ○ | ○ | ○ | ○ |
| csb008 | ○ | ○ | ○ | ○ | ○ | ○ | ○ | ○ |
| csb009 | ○ | ○ | X | ○ | ○ | ○ | ○ | ○ |
| csb010 | ○ | ○ | ○ | ○ | ○ | X | X | ○ |
| csb011 | ○ | X | ○ | ○ | ○ | X | ○ | ○ |
| csb012 | ○ | X | X | ○ | ○ | ○ | X | X |
| csb013 | ○ | ○ | ○ | ○ | ○ | X | ○ | ○ |
| csb019 | ○ | ○ | ○ | ○ | ○ | ○ | ○ | ○ |
| csb020 | ○ | ○ | ○ | ○ | ○ | X | ○ | ○ |
| csb024 | ○ | ○ | ○ | ○ | ○ | ○ | ○ | ○ |
| csb025 | ○ | ○ | ○ | ○ | ○ | ○ | ○ | ○ |
| csb026 | ○ | ○ | ○ | ○ | ○ | ○ | ○ | ○ |
| csb027 | ○ | ○ | ○ | ○ | ○ | X | X | ○ |
| csb032 | ○ | ○ | X | ○ | ○ | X | X | X |
| csb033 | ○ | ○ | ○ | ○ | ○ | ○ | ○ | ○ |
| csb034 | ○ | ○ | ○ | ○ | ○ | ○ | ○ | ○ |
| csb035 | ○ | ○ | ○ | ○ | ○ | X | ○ | ○ |
| csb036 | ○ | ○ | X | ○ | ○ | ○ | X | ○ |
| csb037 | X | ○ | ○ | ○ | ○ | ○ | ○ | ○ |
| csb038 | ○ | ○ | ○ | ○ | ○ | ○ | ○ | ○ |
| csb039 | ○ | ○ | ○ | ○ | ○ | ○ | ○ | ○ |
| csb041 | ○ | ○ | ○ | ○ | ○ | ○ | ○ | ○ |
| csb044 | ○ | ○ | ○ | ○ | ○ | ○ | ○ | ○ |
| csb047 | ○ | ○ | X | ○ | X | ○ | ○ | ○ |
| csb053 | ○ | ○ | X | ○ | ○ | ○ | X | ○ |
| csb054 | ○ | ○ | X | ○ | ○ | ○ | ○ | ○ |
| csb055 | ○ | ○ | ○ | ○ | ○ | ○ | ○ | ○ |
| csb057 | ○ | ○ | ○ | ○ | ○ | ○ | ○ | ○ |
| csb059 | ○ | ○ | ○ | ○ | X | ○ | X | X |
| csb061 | ○ | ○ | X | ○ | X | ○ | ○ | ○ |
| csb064 | X | ○ | ○ | ○ | ○ | ○ | X | ○ |
| csb068 | ○ | ○ | X | ○ | ○ | ○ | ○ | ○ |
| csb074 | ○ | ○ | ○ | ○ | ○ | ○ | ○ | ○ |
| csb075 | X | ○ | ○ | ○ | ○ | ○ | ○ | ○ |
| csb082 | X | ○ | X | ○ | ○ | ○ | ○ | ○ |
| csb083 | X | ○ | ○ | ○ | ○ | ○ | ○ | ○ |
| csb084 | X | ○ | X | ○ | ○ | ○ | X | ○ |
| csb089 | X | X | X | ○ | X | ○ | X | X |
| csb091 | ○ | ○ | X | ○ | X | X | ○ | ○ |
| csb102 | ○ | ○ | ○ | X | X | ○ | X | ○ |
| csb107 | ○ | X | ○ | ○ | X | ○ | ○ | ○ |
| csb111 | X | X | ○ | ○ | X | ○ | X | ○ |
| csb112 | X | ○ | X | ○ | X | ○ | X | X |
| csb114 | X | ○ | ○ | ○ | ○ | ○ | X | ○ |
| csb116 | ○ | ○ | ○ | ○ | X | ○ | ○ | ○ |
| csb118 | X | ○ | ○ | ○ | ○ | ○ | X | ○ |
| csb119 | X | ○ | X | ○ | X | ○ | X | ○ |
| csb125 | X | ○ | ○ | ○ | X | ○ | X | ○ |
| csb132 | X | ○ | ○ | ○ | X | ○ | ○ | ○ |
| csb133 | X | ○ | ○ | ○ | ○ | ○ | ○ | X |
| csb137 | X | X | X | ○ | ○ | ○ | X | ○ |
| csb138 | X | ○ | X | ○ | ○ | ○ | X | ○ |
| csb145 | X | ○ | ○ | ○ | X | ○ | X | ○ |
| csb149 | X | X | X | ○ | X | ○ | X | ○ |

TABLE 9-continued

| Study no. | Bradycardias | Reduced perfusion, hypotension or fluid resuscitation | Temperature instability | Metabolic acidosis | Feed intolerance or abdominal concerns | Abnormal tone or irritability | Lethargy | Jaundice |
|---|---|---|---|---|---|---|---|---|
| csb152 | ○ | X | ○ | ○ | ○ | ○ | ○ | ○ |
| csb155 | X | ○ | ○ | ○ | X | ○ | X | ○ |
| csb157 | ○ | ○ | ○ | ○ | ○ | ○ | X | ○ |
| csb159 | X | ○ | X | ○ | ○ | ○ | ○ | X |
| csb161 | X | ○ | ○ | ○ | X | ○ | X | X |
| csb162 | X | ○ | X | ○ | ○ | ○ | X | ○ |
| csb164 | X | X | X | ○ | ○ | ○ | X | ○ |
| csb191 | ○ | ○ | ○ | ○ | ○ | ○ | X | ○ |
| csb198 | X | X | X | ○ | ○ | ○ | X | ○ |
| csb203 | X | X | X | ○ | ○ | ○ | X | ○ |
| csb216 | ○ | ○ | ○ | ○ | X | ○ | ○ | ○ |
| csb226 | ○ | X | X | ○ | ○ | ○ | ○ | ○ |
| csb239 | ○ | ○ | ○ | ○ | X | ○ | ○ | ○ |
| csb253 | ○ | ○ | ○ | ○ | X | ○ | ○ | ○ |
| csb262 | ○ | X | X | X | ○ | ○ | ○ | ○ |
| csb267 | X | ○ | ○ | ○ | ○ | ○ | X | ○ |
| csb269 | ○ | ○ | ○ | ○ | ○ | ○ | ○ | X |
| csb271 | ○ | ○ | ○ | ○ | ○ | ○ | ○ | ○ |
| csb275 | ○ | ○ | X | ○ | ○ | ○ | X | ○ |
| csb278 | ○ | ○ | X | ○ | ○ | ○ | ○ | ○ |
| csb283 | ○ | ○ | ○ | ○ | ○ | ○ | ○ | ○ |
| csb287 | ○ | X | ○ | ○ | X | X | ○ | ○ |
| csb297 | X | X | X | ○ | ○ | ○ | ○ | ○ |
| csb299 | X | X | X | ○ | X | ○ | X | ○ |

TABLE 10

| Study no. | Poor colour or looks unwell | Other | Abnormal lab parameters | Death | Timing of death (days post sample) | Hb g/l | White cell count ($10^6$/ml) | Neutrophil count ($10^6$/ml) |
|---|---|---|---|---|---|---|---|---|
| csb002 | ○ | rash | | ○ | | 156 | 15.9 | 11.28 |
| csb005 | X | rash, oedema | | ○ | | 105 | 6.2 | 2.7 |
| csb008 | ○ | IUGR | | ○ | | 193 | 10.4 | 3.49 |
| csb009 | ○ | | neutrophilia, low platelets | ○ | | 115 | 16.4 | 15.03 |
| csb010 | X | | | ○ | | 164 | 14.3 | 9.91 |
| csb011 | ○ | sticky eye | neutrophilia | ○ | | 174 | 29.6 | 23.29 |
| csb012 | X | ○ | low platelets | ○ | | 184 | 18.1 | 5.44 |
| csb013 | ○ | | | ○ | | 181 | 17.2 | 9.59 |
| csb019 | ○ | | | ○ | | 174 | 15.7 | 8.16 |
| csb020 | ○ | no respiratory effort at birth | | ○ | | 188 | 6 | 2.78 |
| csb024 | ○ | | | ○ | | 186 | 11.1 | 2.92 |
| csb025 | ○ | rash | | ○ | | 183 | 12.5 | 5.08 |
| csb026 | ○ | rash | | ○ | | 163 | 14.2 | 7.83 |
| csb027 | ○ | poor suck | | ○ | | 184 | 21.8 | 11.99 |
| csb032 | ○ | red groin | elevated white cell count | ○ | | 168 | 29.4 | 23.81 |
| csb033 | ○ | rash | | ○ | | 162 | 11.5 | 10.22 |
| csb034 | ○ | | | ○ | | 210 | 9.3 | 9.3 |
| csb035 | ○ | | | ○ | | 196 | 20.1 | 12.66 |
| csb036 | ○ | | | ○ | | 185 | 20 | 13.53 |
| csb037 | X | quiet | | ○ | | 96 | 8.6 | 2.06 |
| csb038 | ○ | plethoric | neutropenia | ○ | | 182 | 6.2 | 0.97 |
| csb039 | ○ | plethoric | neutropenia | ○ | | 195 | 5.4 | 1.43 |
| csb041 | X | hypertension, 2 days post op diaphragmatic hernia repair | | ○ | | 119 | 10.6 | 6.7 |
| csb044 | ○ | hypoglycaemia | | ○ | | 179 | 10 | 2.62 |
| csb047 | X | known NEC, central line | low platelets | X | 7 | 91 | 9.9 | 6.34 |
| csb053 | X | | | ○ | | 147 | 6.4 | 3.72 |
| csb054 | ○ | poor feeding | | ○ | | 173 | 21.6 | 16.2 |
| csb055 | ○ | rash | | ○ | | 231 | 7.7 | 5.11 |
| csb057 | ○ | starry eyed | | ○ | | 201 | 18.4 | 11.91 |
| csb059 | ○ | pale, fine creps in chest, spleen tipable | neutrophilia | ○ | | 201 | 21.6 | 17.05 |
| csb061 | ○ | ?NEC, quiet | high white counr, neutrophilia | ○ | | 155 | 42.4 | 36.46 |
| csb064 | ○ | pale | neutrophilia | ○ | | 112 | 29 | 20.33 |

TABLE 10-continued

| Study no. | Poor colour or looks unwell | Other | Abnormal lab parameters | Death | Timing of death (days post sample) | Hb g/l | White cell count (10⁶/ml) | Neutrophil count (10⁶/ml) |
|---|---|---|---|---|---|---|---|---|
| csb068 | ○ | offensive liquor | | ○ | | 179 | 10.9 | 4.78 |
| csb074 | ○ | | | ○ | | 182 | 16.5 | 9.05 |
| csb075 | X | | | ○ | | 81 | 5.8 | 1.18 |
| csb082 | ○ | quiet, intubated the next day | low platelets | ○ | | 143 | 16.2 | 12.01 |
| csb083 | ○ | | low platelets | ○ | | 89 | 9.8 | 3.6 |
| csb084 | ○ | | low platelets | ○ | | 98 | 13.7 | 4.8 |
| csb089 | ○ | loose stool | neutrophilia | ○ | | 83 | 23.9 | 20.08 |
| csb091 | X | quiet | | ○ | | 173 | 10 | 7.8 |
| csb102 | ○ | central line, blood sugar instability | low platelets | X | >30 | 102 | 6.9 | 3.86 |
| csb107 | ○ | hyperglycaemia | low platelets, high white cell count | X | 7 | 118 | 31 | 24 |
| csb111 | X | | neutrophilia | ○ | | 112 | 24 | 22 |
| csb112 | X | hyperglycaemia | high white cell count, neutrophilia | ○ | | 109 | 49.7 | 44.7 |
| csb114 | X | | | ○ | | 130 | 13 | 6 |
| csb116 | ○ | red hot fluctuant swelling forearm | low platelets | ○ | | 111 | 15.1 | 6.8 |
| csb118 | X | | low platelets | ○ | | 88 | 3.1 | 2 |
| csb119 | X | | low platelets | ○ | | 109 | 17.1 | 4.8 |
| csb125 | X | | high white cell count | ○ | | 85 | 85 | 10.86 |
| csb132 | ○ | | low platelets | ○ | | 94 | 14 | 7.4 |
| csb133 | ○ | hyperglycaemia | | ○ | | 138 | 7.5 | 6.6 |
| csb137 | X | | low platelets | ○ | | 126 | 16.4 | 13.6 |
| csb138 | ○ | quiet | | ○ | | 108 | 13.9 | 8.3 |
| csb145 | ○ | | low platelets | ○ | | 131 | 6.3 | 3.8 |
| csb149 | X | quiet | low platelets | ○ | | 116 | 7.6 | 3.2 |
| csb152 | ○ | trisomy 21 | low platelets | X | 12 | 158 | 18.3 | 13.4 |
| csb155 | ○ | | | ○ | | 143 | 9 | 5.2 |
| csb157 | ○ | surgical wound abscess/granuloma, central line | low platelets | ○ | | 148 | 5.6 | 2.2 |
| csb159 | ○ | | elevated white cell count, bordeline platelets | ○ | | 171 | 22.7 | 17.3 |
| csb161 | X | | low platelets | ○ | | 117 | 7 | 2.7 |
| csb162 | ○ | | | ○ | | 103 | 11.1 | 7.5 |
| csb164 | ○ | quiet, previous NEC | low platelets | ○ | | 127 | 10.9 | 9.2 |
| csb191 | ○ | | neutrophilia | ○ | | 189 | 16 | 14.12 |
| csb198 | X | quiet, tachycardic | | ○ | | 116 | 6.8 | 4.73 |
| csb203 | X | quiet | low platelets | ○ | | 124 | 7.4 | 3.94 |
| csb216 | ○ | glucose instability | low platelets | ○ | | 131 | 11.8 | 5.23 |
| csb226 | ○ | central line | | ○ | | . | . | . |
| csb239 | X | central line | low platelets | X | 2 | 94 | 11.7 | 5.5 |
| csb253 | ○ | rash, sore | neutrophilia | ○ | | 127 | 27.5 | 21.1 |
| csb262 | ○ | raised lactate, stoma | bordeline platelets | ○ | | 114 | 6.6 | 3.8 |
| csb267 | ○ | lump and extravasation on arm | bordeline platelets | ○ | | 111 | 5.7 | 3.5 |
| csb269 | ○ | rash, IUGR, brain cyst, splenomegally | low platelets | ○ | | 179 | 4.9 | 2.21 |
| csb271 | ○ | extravasation | low platelets | ○ | | 113 | 10 | 3.4 |
| csb275 | ○ | central line, previous NEC | | ○ | | 102 | 19 | 13.66 |
| csb278 | ○ | tachycardic, nasal secretions | | ○ | | 98 | 10.7 | 2.5 |
| csb283 | ○ | <12 hours post-op NEC | low platelets | ○ | | 165 | 16.1 | 12.2 |
| csb287 | X | | | ○ | | 110 | 7.9 | 3.9 |
| csb297 | ○ | | low white cells, low platelets | ○ | | 110 | 2.7 | 1.6 |
| csb299 | X | central line, blood sugar instability | low platelets | ○ | | 85 | 2.8 | 1.8 |

TABLE 11

| Study no. | Platelets | pH | Sugar | Expert opinion on likelihood of infection in "possibles" | Other diagnoses |
|---|---|---|---|---|---|
| csb002 | 248 | 7.425 | | low | |
| csb005 | 190 | 7.248 | 5.7 | high | patent ductus arteriosus ligated 4 days later |
| csb008 | 208 | | | medium | |
| csb009 | 14 | 7.29 | 3.7 | | |
| csb010 | 199 | 7.26 | 4.7 | high | |
| csb011 | 200 | 7.26 | 2 | medium | |
| csb012 | 7 | 7.26 | 3.44 | | |
| csb013 | 244 | 7.339 | 2.3 | low | |
| csb019 | 241 | 7.273 | 1.9 | low | |
| csb020 | 243 | 7.364 | 1.47 | low | |
| csb024 | 274 | 7.31 | 3.64 | low | |
| csb025 | 282 | 7.22 | | low | |
| csb026 | 246 | 7.122 | 2.1 | medium | |
| csb027 | 306 | 7.192 | 3.3 | medium | |
| csb032 | 320 | 7.402 | 5.9 | | |
| csb033 | 278 | 7.274 | 3.5 | medium | |
| csb034 | 241 | 7.268 | 0.3 | medium | |
| csb035 | 293 | | | low | |
| csb036 | 208 | | 3.9 | low | |
| csb037 | 171 | 7.262 | 4.2 | low | |
| csb038 | 202 | 7.349 | | low | |
| csb039 | 214 | 7.338 | 1.6 | low | |
| csb041 | 198 | 7.186 | 4.4 | medium | post-op diaphragmatic hernia |
| csb044 | 286 | | 1.17 | low | |
| csb047 | 53 | 7.278 | 4.2 | | |
| csb053 | 261 | 7.161 | 5.2 | high | |
| csb054 | 259 | 7.31 | 4.4 | medium | |
| csb055 | 164 | 7.387 | 3 | low | |
| csb057 | 189 | 7.354 | 3.6 | low | |
| csb059 | 310 | | | high | |
| csb061 | 392 | 7.368 | 4.3 | high | |
| csb064 | 288 | 7.09 | 6.5 | high | |
| csb068 | 235 | | | low | |
| csb074 | 337 | 7.193 | 2 | medium | |
| csb075 | 250 | | | | |
| csb082 | 0 | | | | |
| csb083 | 31 | | | | |
| csb084 | 40 | | 2.36 | | |
| csb089 | 453 | 7.235 | 6.3 | | |
| csb091 | 200 | 7.384 | 3.87 | | |
| csb102 | clumped | 7.2 | 2.3 | | |
| csb107 | 88 | 7.14 | 10.4 | | |
| csb111 | 205 | 7.22 | 5.7 | | |
| csb112 | 317 | 7.18 | 14.9 | | |
| csb114 | 287 | 7.25 | 8.46 | | |
| csb116 | 101 | | | | |
| csb118 | 108 | 7.26 | | | |
| csb119 | 78 | 7.2 | 3.33 | | |
| csb125 | 324 | 7.29 | 3.82 | | |
| csb132 | 60 | | | | |
| csb133 | 241 | 7.26 | 9.9 | | |
| csb137 | 79 | | | | |
| csb138 | 177 | 7.37 | 10.4 | | |
| csb145 | 66 | | | | |
| csb149 | 10 | 7.22 | 2.4 | | |
| csb152 | 92 | 7.19 | 2 | | |
| csb155 | 224 | 7.28 | 5.1 | | |
| csb157 | 104 | 7.37 | | | |
| csb159 | 142 | 7.29 | | | |
| csb161 | 47 | 7.19 | 6.8 | | |
| csb162 | 237 | 7.25 | 11 | | |
| csb164 | 84 | 7.21 | | | |
| csb191 | 223 | 7.39 | 6.3 | | |
| csb198 | 287 | 7.2 | 4.5 | | |
| csb203 | 67 | 7.38 | 3.8 | | |
| csb216 | 15 | 7.39 | 3.1 | | |
| csb226 | . | . | . | | |
| csb239 | 33 | | 11.5 | | |
| csb253 | 339 | | | | |
| csb262 | 125 | 7.18 | 5.4 | | |
| csb267 | 122 | 7.37 | 3.8 | | |
| csb269 | 33 | | 3.3 | | |
| csb271 | 85 | 7.38 | 4.2 | | |
| csb275 | 196 | | | | |
| csb278 | 472 | 7.34 | 5.4 | | |

TABLE 11-continued

| Study no. | Platelets | pH | Expert opinion on likelihood of infection Sugar in "possibles" | Other diagnoses |
|---|---|---|---|---|
| csb283 | 62 | 7.43 | 4 | |
| csb287 | 231 | 7.38 | 4.7 | |
| csb297 | 104 | 7.31 | | |
| csb299 | 55 | 7.23 | 4.8 | |

Further Experimental and Analytical Work

Additional studies have been undertaken to further validate the initial results discussed in Examples 1 to 11. In particular, further studies have focused on a population from outside of the UK with a different ethnic composition, an adult population and an additional neonatal population. This work supports the findings in the earlier studies discussed above, and provides evidence that the biomarkers of the present invention provide for robust and accurate detection of sepsis.

Additionally, further statistical analysis has been performed to identify preferred biomarkers for adult sepsis, but these findings may also be highly relevant for paediatric and neonatal patients.

EXAMPLE 12

Gambian Samples

Figure 19:
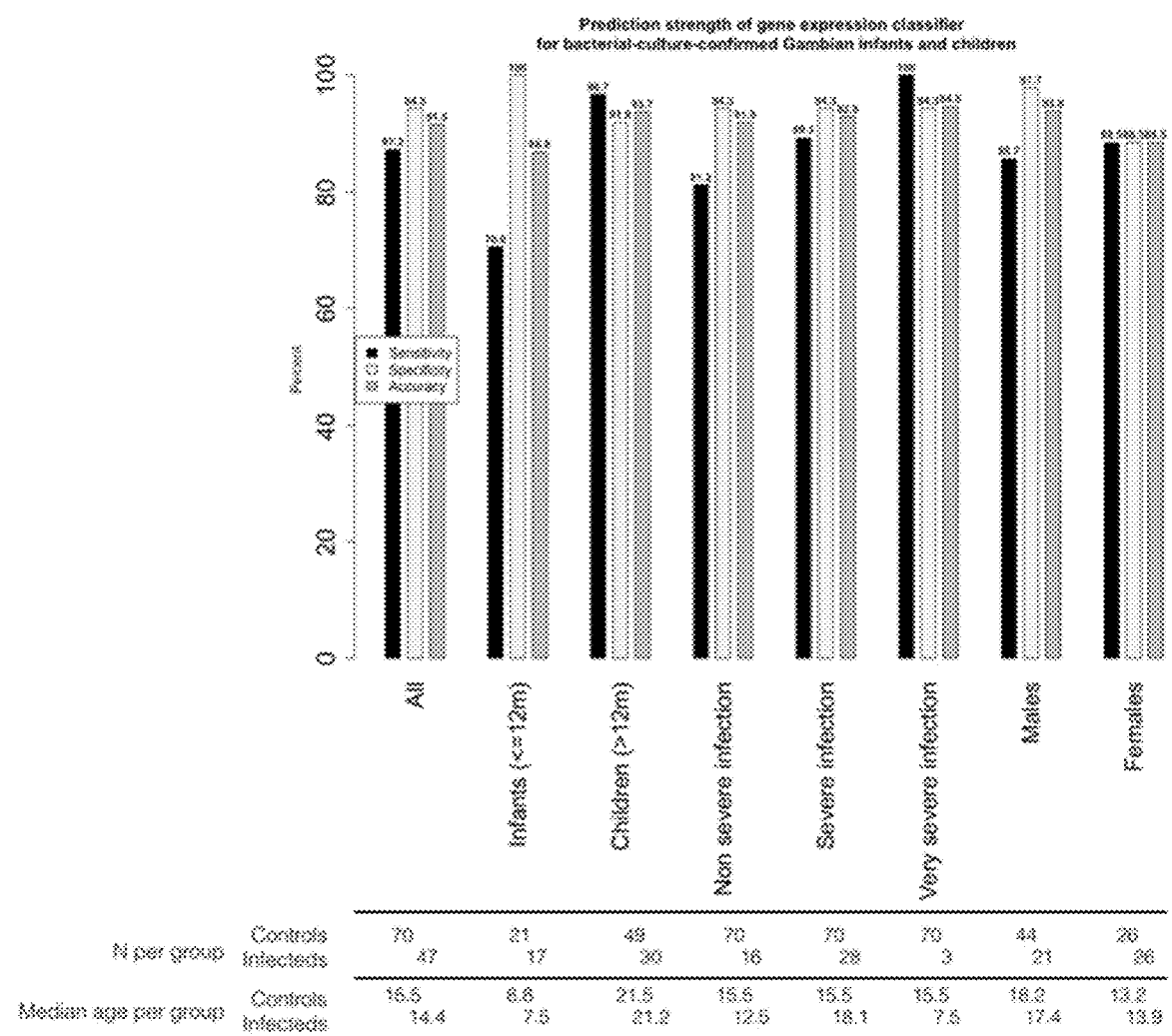
FIG. 19 shows a bar graph of prediction strength of gene expression classifier for bacterial culture confirmed Gambian infants and children.

We have now analysed the performance of the classifier using whole blood RNA from 117 African infants and children with blood culture positive sepsis—this study was conducted in the Gambia. This is a much older group than was analysed in the previous neonatal pre-term infant study and is in a very different ethnic setting. Overall a 92% accuracy for predicting sepsis was detected, which is a remarkably good result. The results are shown in FIG. 19, along with details of the patient group. The results are stratified so it can be seen how this breaks down in terms of demographics of age, sex and clinical severity of disease. This analysis was conducted with 47 of the 52 biomarkers as some of the biomarkers were absent from the platform used in the Gambian studies. The Affymetrix Human Genome U219.5 system was used. Biomarkers omitted for technical reasons (i.e. either not present on the array at all or missing/incorrect annotation) were LIME1, SLC2A3, TRAJ17, TRBV28, "LOC729021//LOC729010".

EXAMPLE 13

Adult Samples

Figure 20:
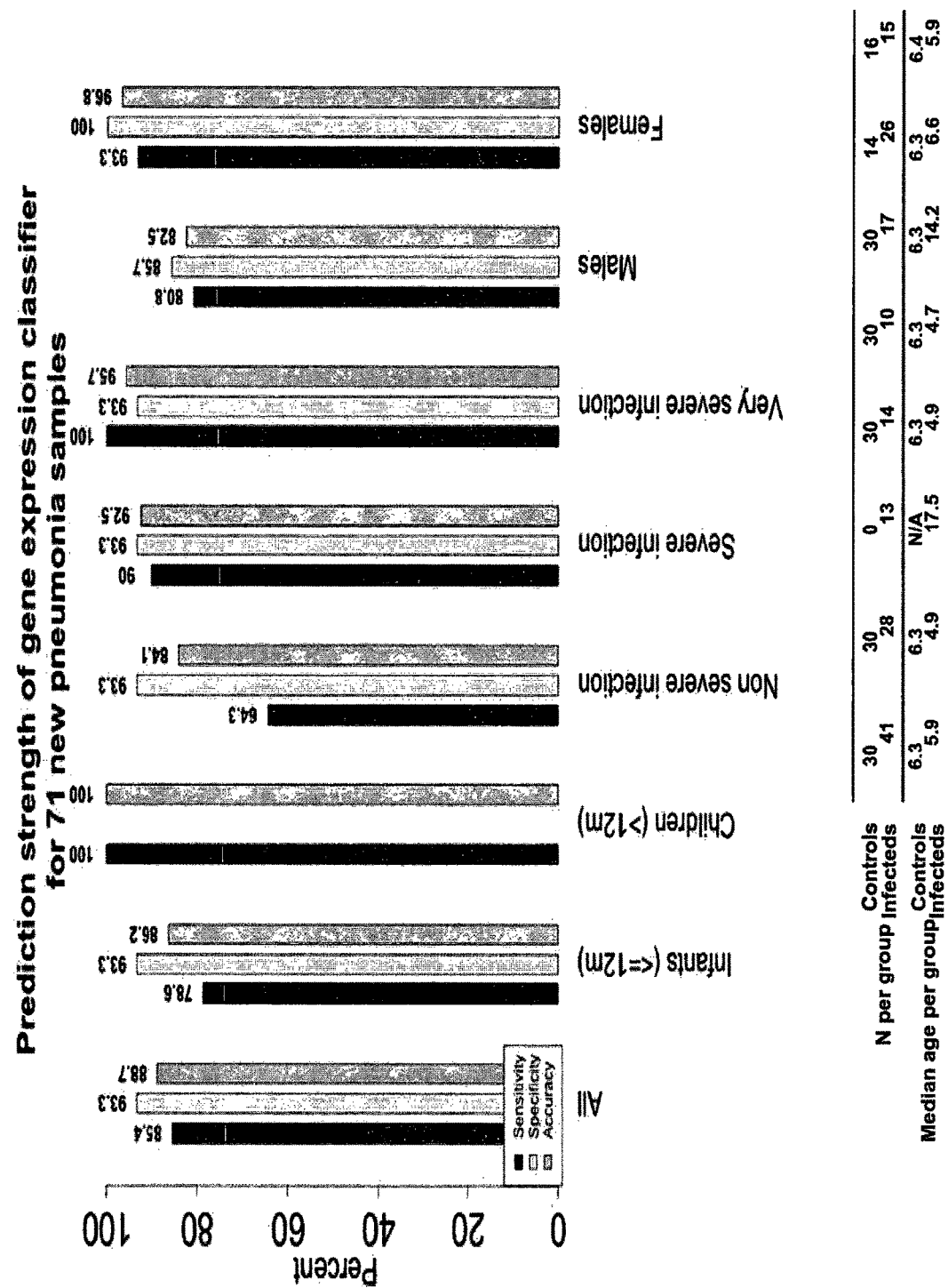
FIG. 20—A shows the demographics of the test group and controls, B shows the shows a bar graph of prediction strength of gene expression classifier for adult bacterial pneumonia samples.

The performance of the 52 marker classifier using adult data for sepsis have now analysed. The observed results were very positive. A 91% accuracy was observed in adults, which is only a few (8%) percent down in performance in comparison with the neonatal population. There is no gender bias. Also this data set had samples taken at different days post diagnosis of sepsis (days 1-5) and therefore this allows us to score for the sensitivity over different sampling times. This works out at 100% and as we have matched controls for the day 5 samples we can also calculate accuracy, which in this case is 85%. Accordingly the performance is maintained at different times of sampling. FIG. 20B shows the result in graphic form and FIG. 20A shows the demographics of the study group.

EXAMPLE 14

Further Neonatal Samples

Figure 21:
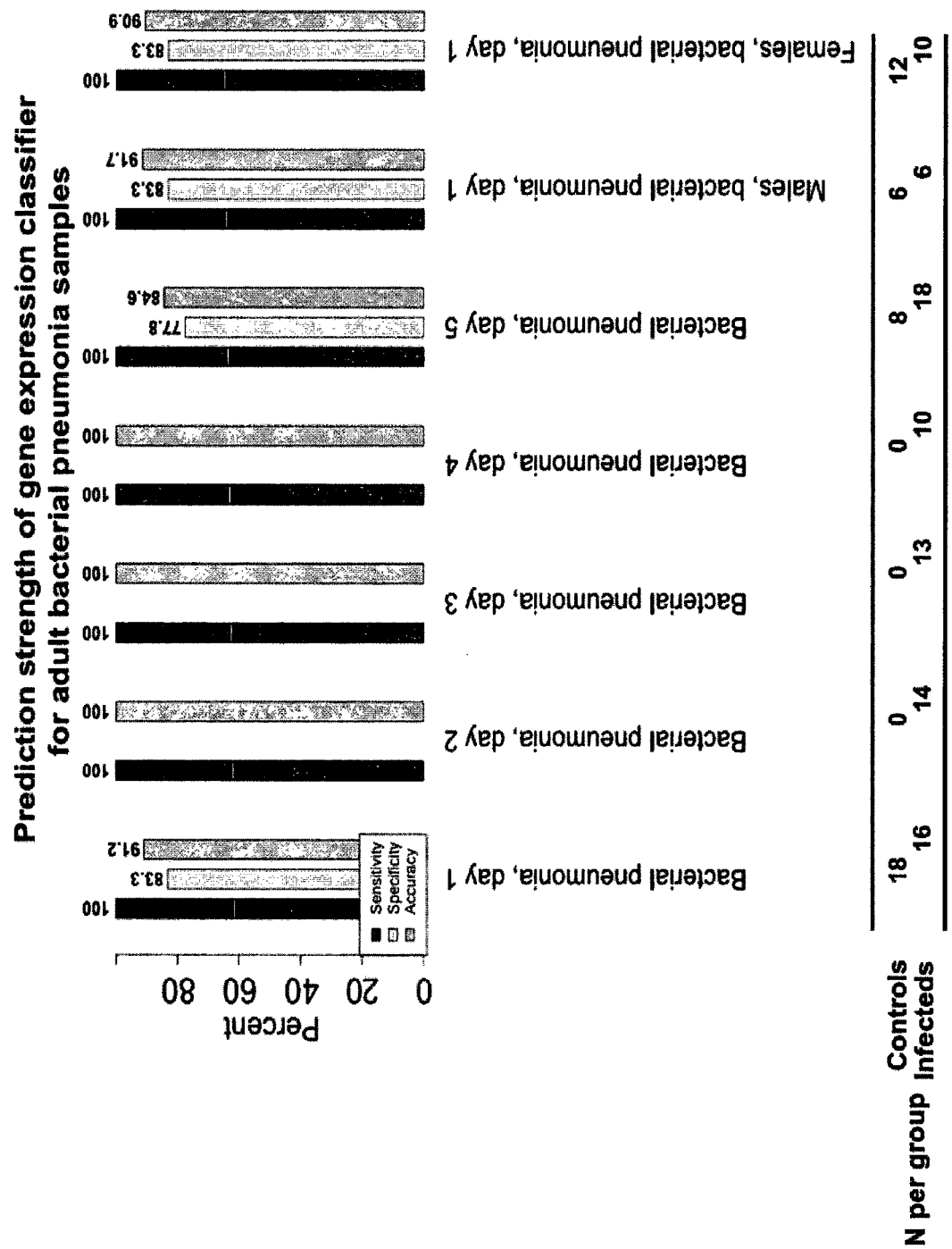
FIG. 21 shows a bar graph of prediction strength of gene expression classifier for 71 neonate samples.

The 52 marker classified has now been applied to neonates using a completely different set of samples. The performance in this set shows an accuracy ranging from 83%-100%. This provides strong evidence for repeated high performance in three completely independent populations, again further supporting the promise of the present invention. The results are shown in FIG. 21.

It is interesting to note that in the mildly sick cases sensitivity goes down slightly. This therefore support the use of the biomarkers of the present invention as a prognostic indicator and for determining antibiotic therapeutic response.

EXAMPLE 15

Further Statistical Analysis

Figure 28:
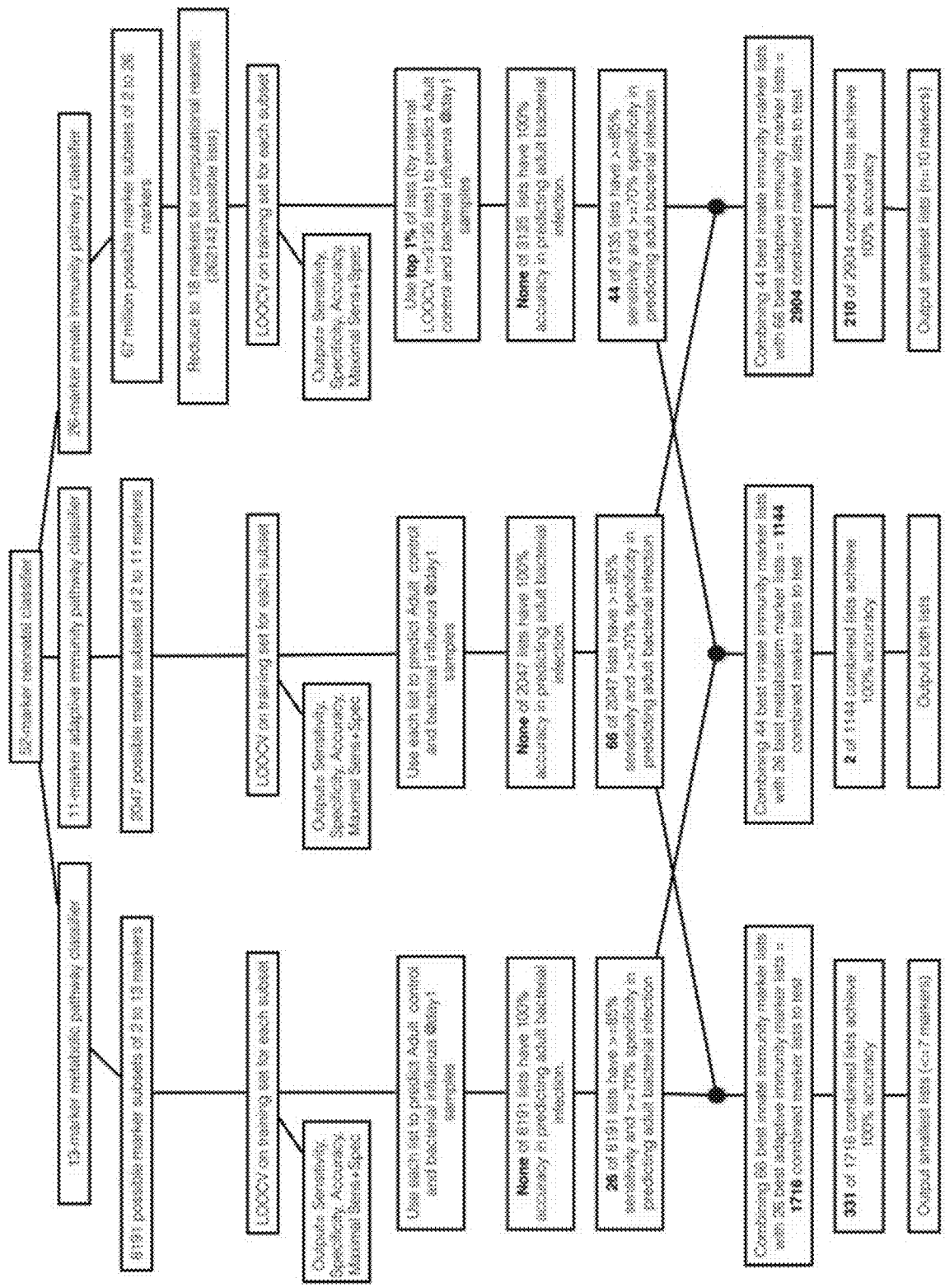
FIG. 28 shows a flow chart illustrating part of the statistical analysis performed to analyse and rank the performance of various combinatorial marker lists.

Further statistical analysis has been performed using the 52 biomarkers and various data sets, including the new adult data discussed above. The aim was both to identify combinations of biomarkers from two of the metabolic, innate and adaptive immune marker group (i.e. A, B and C) that provide a very accurate test, and also to identify which biomarkers most frequently appear in the best performing lists when large numbers of possible combinations are examined. Large numbers of combinatorial possibilities between pathway lists were therefore examined with the aim of optimising the accuracy of detecting adult sepsis and determining key biomarkers more generally. FIG. 28 schematically illustrates this work The results are summarised in the Tables 12 to 14 below. They show it is possible to achieve 100% accuracy by combining biomarkers selected from two pathways. Combining biomarkers from metabolic and innate immunity pathways gives 2 combined lists which achieve 100% accuracy (100% accuracy is 100% sensitivity with 100% specificity). Combining biomarkers from metabolic with adaptive immunity pathways gives 331 combined lists which achieve 100% accuracy, but only the 5 with less than or equal to 7 genes have been shown in the table below. Combining innate and adaptive immunity pathways yields 210 combined lists which achieve 100% accuracy, but only the 6 with less than 10 genes.

All of these combined lists demonstrate 100% accuracy on the test data. It will be apparent that 100% accuracy is a very rigorous standard, and such accuracy may not be required for a clinically useful test. Thus using fewer biomarkers, or a less optimal marker set, can nonetheless provide for a very useful result.

The smallest set of biomarkers comes from combining metabolic with adaptive immunity (Table 13)—here the smallest number of combined genes is 6 that have 100% accuracy for detecting adult sepsis.

TABLE 12

Combined lists of biomarkers able to achieve 100% accuracy
Innate Immunity Marker Lists PLUS Metabolism Marker Lists

|  | List 1 | List 2 |
|---|---|---|
| Innate immunity marker list | MMP9<br>IL1R2<br>DYSF<br>PGLYRP1<br>BASP1<br>CKAP4<br>FGR<br>& | MMP9<br>IL1R2<br>DYSF<br>BASP1<br>CEBPD<br>CKAP4<br>FGR<br>& |
| Metabolism marker list | RETN<br>GPR84<br>STXBP2<br>HK3<br>MPO<br>GYG1<br>FPR2<br>FFAR2 | RETN<br>HK3<br>MPO<br>ALPL<br>GYG1<br>GRINA |

TABLE 13

Combined lists of biomarkers able to achieve 100% accuracy
Adaptive Immunity Marker Lists PLUS Metabolism Marker Lists

|  | List 1 | List 2 | List 3 | List 4 | List 5 |
|---|---|---|---|---|---|
| Adaptive immunity marker list | CD247<br>TRAJ17<br>CD3D | CD247<br>TRAJ17<br>CD3D | CD247<br>TRAJ17<br>CD3D<br>MAL | CD247<br>TRAJ17<br>TRBV28<br>MAL | CD247<br>TRAJ17<br>TRBV28<br>HLA-DMB |
|  | & | & | & | & | & |
| Metabolism marker list | HK3<br>MPO<br>SLC2A3 | HK3<br>MPO<br>GYG1<br>SLC2A3 | HK3<br>MPO<br>SLC2A3 | HK3<br>MPO<br>SLC2A3 | HK3<br>MPO<br>SLC2A3 |

TABLE 14

Combined lists of biomarkers able to achieve 100% accuracy
Innate Immunity Marker Lists PLUS Adaptive Immunity Marker Lists

|  | List 1 | List 2 | List 3 | List 4 | List 5 | List 6 |
|---|---|---|---|---|---|---|
| Innate immunity marker list | MMP9<br>IL1R2<br>DYSF<br>PGLYRP1<br>CEBPD<br>CKAP4<br>& | MMP9<br>IL1R2<br>DYSF<br>BASP1<br>CKAP4<br>FGR<br>& | MMP9<br>IL1R2<br>DYSF<br>CEBPD<br>CKAP4<br>IL18R1<br>& | MMP9<br>IL1R2<br>DYSF<br>CEBPD<br>CKAP4<br>FGR<br>& | MMP9<br>IL1R2<br>DYSF<br>CEBPD<br>CKAP4<br>FGR<br>& | MMP9<br>IL1R2<br>DYSF<br>CEBPD<br>CKAP4<br>FGR<br>& |
| Adaptive immunity marker list | CD247<br>TRAJ17<br>TRBV28<br>HLA-DMB | CD247<br>TRAJ17<br>TRBV28<br>HLA-DMB | CD247<br>TRAJ17<br>TRBV28<br>HLA-DMB | CD247<br>TRAJ17<br>CD3D<br>MAL | CD247<br>TRAJ17<br>TRBV28<br>MAL | CD247<br>TRAJ17<br>TRBV28<br>HLA-DMB |

This work further underpins the diagnostic power of the biomarkers of the present invention. Moreover it shows that there are a multitude of potential selections from the biomarkers of groups A, B and C, which can be combined to form the basis of a suitable diagnostic/prognostic assay.

Figure 22:
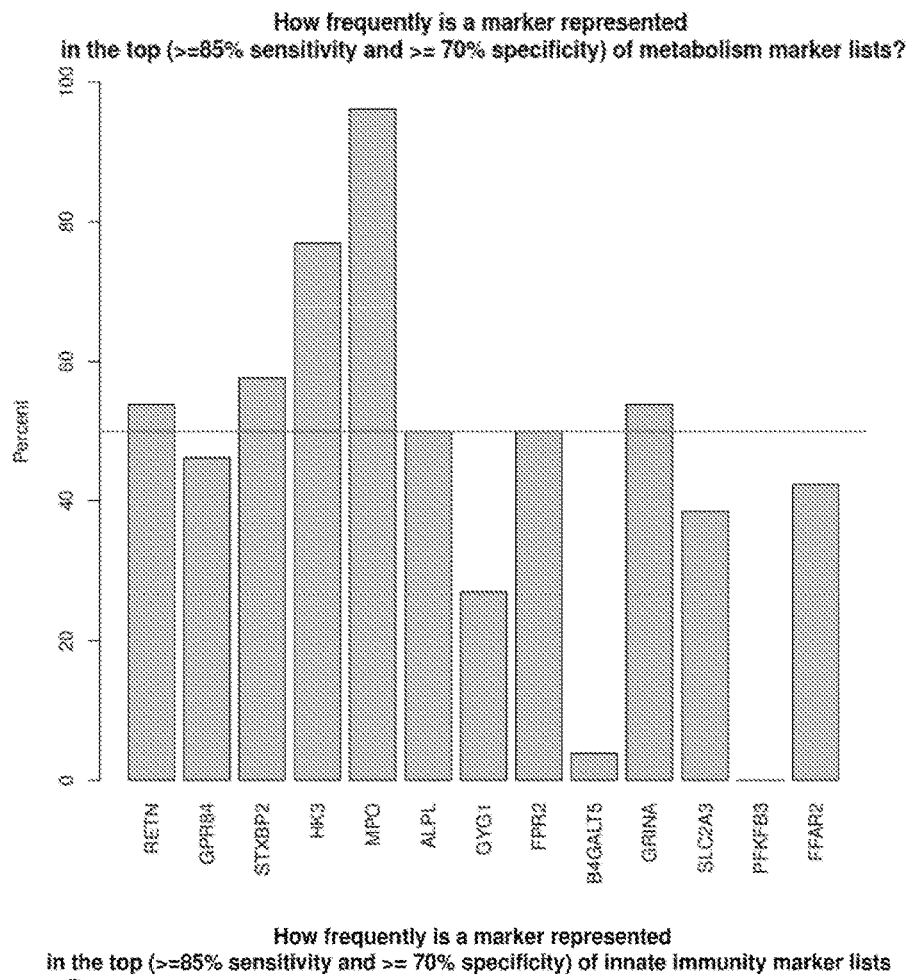
FIG. 22 shows a bar graph of how frequently is a given marker is represented in the top (>=85% sensitivity and >=70% specificity) of metabolism marker combination lists.
Figure 23:
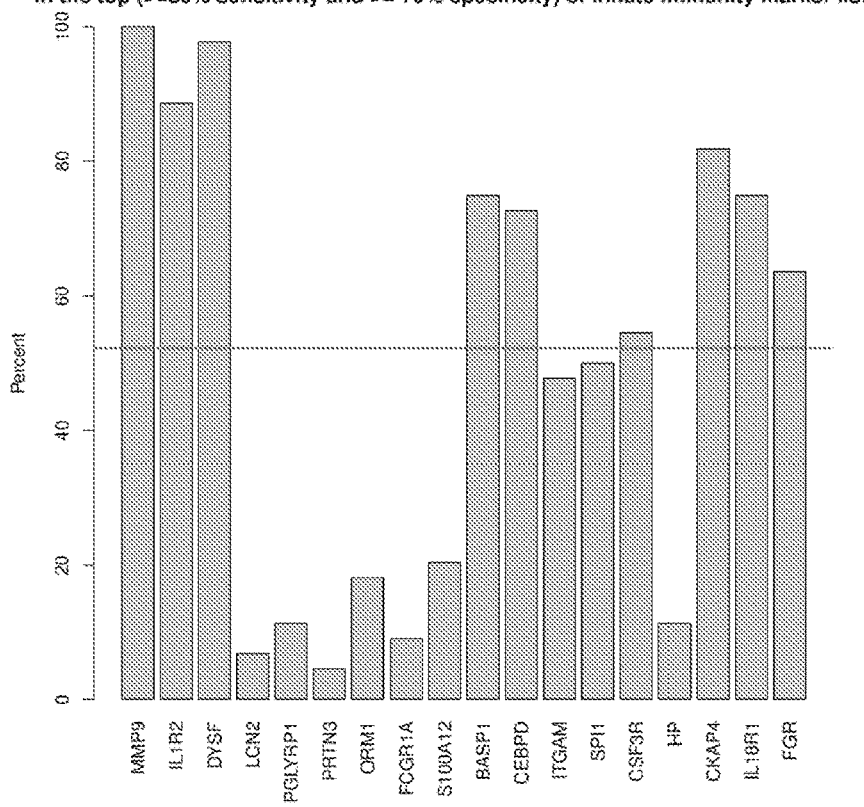
FIG. 23 shows a bar graph of how frequently is a given marker is represented in the top (>=85% sensitivity and >=70% specificity) of innate immunity marker combination lists.
Figure 24:
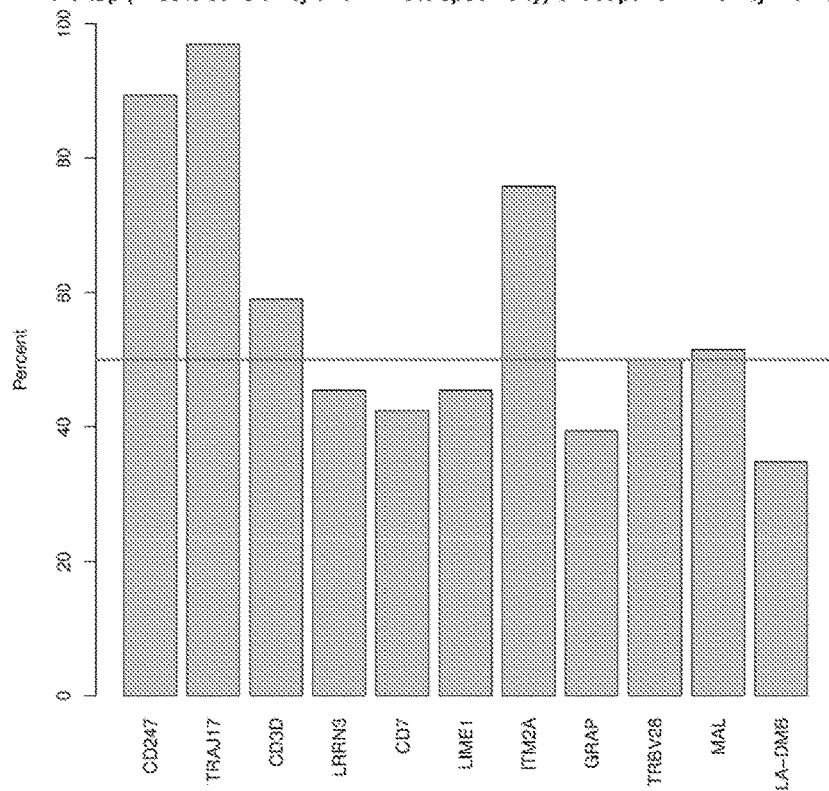
FIG. 24 shows a bar graph of how frequently is a given marker is represented in the top (>=85% sensitivity and >=70% specificity) of adaptive immunity marker combination lists?

FIGS. 22 to 24 show the results of an analysis to determine how frequently various biomarkers from groups A, B and C appear in the combinations of biomarkers for diagnosing adult sepsis which achieve a sensitivity of at least 85% and specificity of at least 70%—these values correlate with a powerful and robust diagnostic test, and thus represent a suitable cut off point for this statistical analysis (however, higher or lower sensitivity/specificity values may of course be appropriate depending on the context). Biomarkers that appear more frequently can be taken to be particularly highly diagnostically useful in typical clinical contexts.

It can be seen that, for group A (metabolic), the biomarkers which consistently perform best are: MPO, HK3, STXBP2, RETN, GRNA, FPR2, and ALPL.

It can be seen that, for group B (innate immunity), the biomarkers which consistently perform best are: MMP9, DYSF, IL1R2, CKAP4, IL18R1, BASP1, CEBPD, FGR, and CSF3R.

It can be seen that, for group C (adaptive immunity), the biomarkers which consistently perform best are: TRAJ17, CD247, ITM2A, CD3D, MAL and TRBV28.

All of these biomarkers are present in at least 50% of combinations of biomarkers for diagnosing sepsis that achieve a sensitivity of at least 85% and specificity of at least 70%. The biomarkers are listed in terms of preference based upon how frequently they appear in the highest performing combinations of biomarkers.

Figure 25:
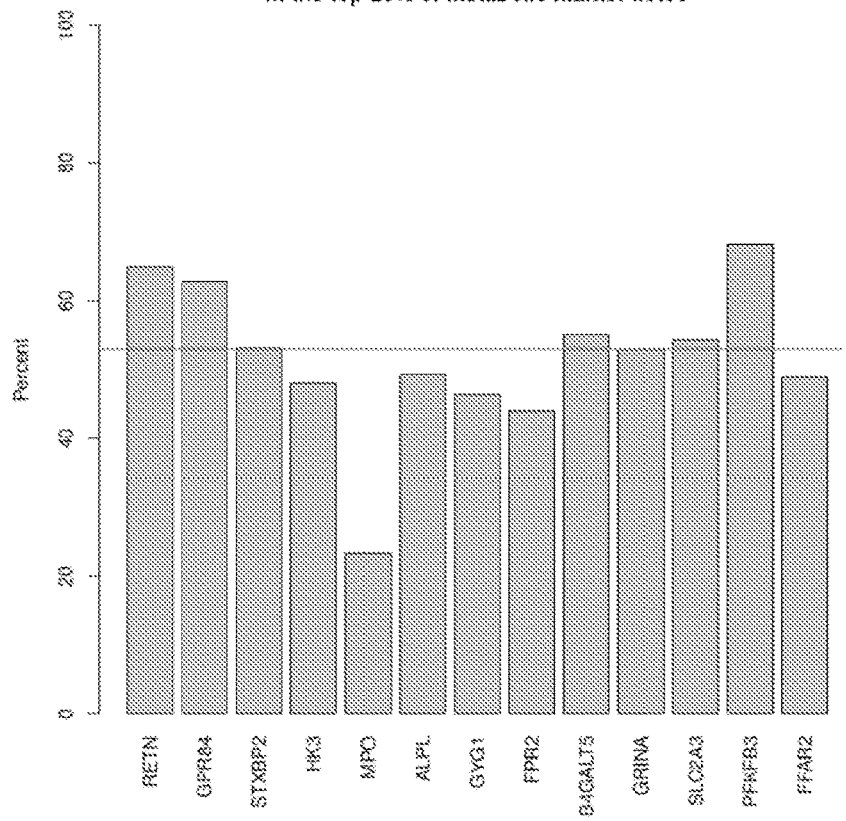
FIG. 25 shows a bar graph of how frequently is a given marker is represented in the top 20% (i.e. the 20% showing highest accuracy) of innate immunity marker combination lists?
Figure 26:
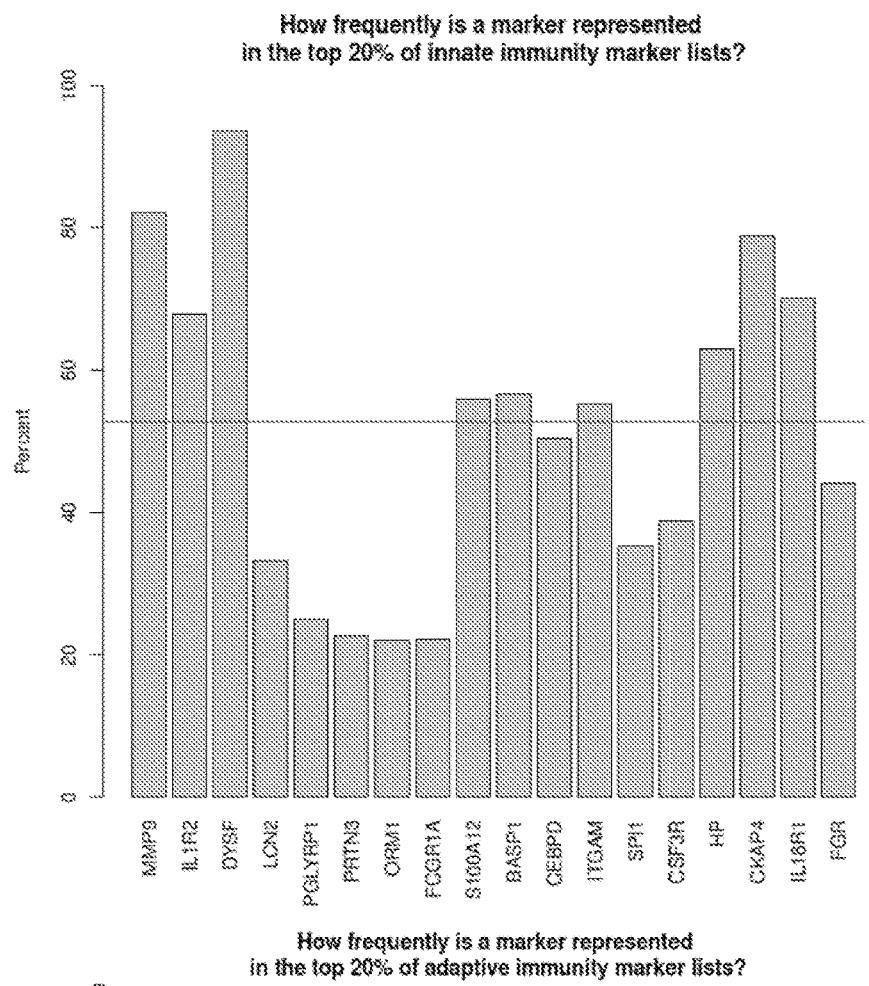
FIG. 26 shows a bar graph of how frequently is a given marker is represented in the top 20% of adaptive immunity marker combination lists?
Figure 27:
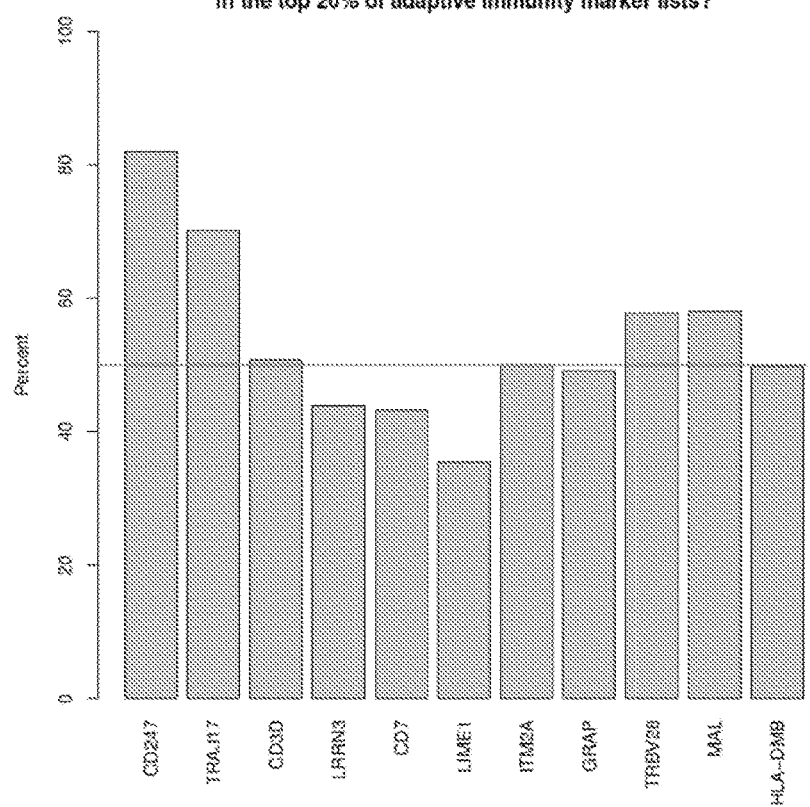
FIG. 27 shows a bar graph of how frequently is a given marker is represented in the top 20% of metabolic marker combination lists?

FIGS. 25 to 27 show the results of an analysis to determine how frequently various biomarkers from groups A, B and C appear in the top 20% of combinations of biomarkers for diagnosing adult sepsis, i.e. the 20% which achieve the highest sensitivity and specificity. These results show which biomarkers are more frequently found in extremely high performance marker sets. This data shows that all biomarkers can have a role in very high performance biomarker lists, and this is evidence that all of the biomarkers in groups A, B and C are diagnostically useful.

The invention claimed is:

1. A method of diagnosing and treating sepsis in a human subject, the method comprising the steps of:
   a) analysing a blood sample obtained from the human subject to determine the levels of three or more biomarkers, the biomarkers comprising SLC2A3, BASP1, and LRRN3, and optionally one or more further biomarkers selected from any of group A consisting of: GYG1, B4GALT5, HK3, GPR84, PFKFB3, RETN, STXBP2, FPR2, ALPL, GRINA, FFAR2, and MPO;

group B consisting of: IL1RN, PSTPIP2, CKAP4, DYSF, C19orf59, IL18R1, MMP9, FGR, SPI1, PGLYRP1, RNF24, ANKRD22, CEBPD, IL1R2, LOC729021 (SRCAP-like helicase), S100A12, ITGAM, FCGR1A, IFITM3, CSF3R, LCN2, TNFAIP6, HP, ORM1, CEACAM1 and PRTN3; and group C consisting of: GRAP, TRAJ17, CD3D, CD247, ITM2A, LIME1, HLA-DMB, CD7, MAL, TRBV28, and RPS29; and wherein each biomarker comprises a biomarker nucleic acid molecule encoding a biomarker protein;

b) identifying the human subject as having sepsis by comparing the levels of the biomarkers determined in step (a) with one or more reference values and determining from the comparison whether there is a difference in the expression levels of the three or more biomarkers relative to the one or more reference values, wherein a difference in the expression levels of the three or more biomarkers in the blood sample from the human subject compared to the one or more reference values is indicative of sepsis; and c) treating in the human subject the sepsis as identified in step (b) by administering to the human subject one or more antibiotics.

2. The method of claim 1, wherein in step a) the biomarkers are SLC2A3, GPR84, RETN, LRRN3, TRAJ17, CD3D, BASP1, CKAP4 and C19orf59.

3. The method of claim 1, wherein in step a) the biomarkers are SLC2A3, BASP1, LRRN3, at least one biomarker selected from group A, and at least one other biomarker selected from any of groups A, B or C.

4. The method of claim 1, wherein in step a) the biomarkers are SLC2A3, BASP1, LRRN3, at least one biomarker selected from group B, and at least one other biomarker selected from any of groups A, B, or C.

5. The method of claim 1, wherein in step a) the biomarkers are SLC2A3, BASP1, LRRN3, and at least one biomarker selected from each of groups A, B and C.

6. The method of claim 1, wherein in step a) the biomarkers are SLC2A3, BASP1, LRRN3, at least one biomarker selected from group A, and at least one biomarker selected from group B.

7. The method of claim 1, wherein in step a) the biomarkers are SLC2A3, BASP1, LRRN3, at least one biomarker selected from group A, and at least one other biomarker selected from group C.

8. The method of claim 1, wherein in step a) the biomarkers are SLC2A3, BASP1, LRRN3, at least one biomarker selected from group B, and at least biomarker selected from group C.

9. The method of claim 1, wherein in step a) the one or more further biomarkers comprise a selection from within sub-group of the biomarkers set out in groups A, B and C, wherein: sub-group A consists of: MPO, HK3, STXBP2, RETN, GRNA, FPR2, and ALPL; sub-group B consists of: MMP9, DYSF, IL1 R2, CKAP4, IL18R1, BASP1, CEBPD, FGR, and CSF3R; and sub-group C consists of: TRAJ17, CD247, ITM2A, CD3D, MAL and TRBV28.

10. The method of claim 9, wherein biomarkers from at least two sub-groups are selected.

11. The method of claim 9, wherein at least one biomarker from sub-group A is selected in combination with at least two biomarkers from sub-group B and/or C.

12. The method of claim 9, wherein at least two biomarkers from sub-group A are used in combination with at least two biomarkers from sub-group B and/or C.

13. The method of claim 1, wherein the human subject is a human neonate or child.

14. The method of claim 1, wherein the human subject is a human adult, child or neonate.

15. The method of claim 1, which further involves investigating physiological measurements selected from heart rate, temperature, respiratory rate and blood pressure or conducting a blood culture.

* * * * *

SEQUENCE LISTING

<160> NUMBER OF SEQ ID NOS: 52

<210> SEQ ID NO 1
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 1
tcacactcct gggctctgaa cacacacgcc agctcctctc tgaagcgact           50

<210> SEQ ID NO 2
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 2
agacttttgg tctgtgggcc atttaacctg gatgccacca ttttatgggg           50

<210> SEQ ID NO 3
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 3
cctcttgtca gagatcctct accacagaca ttaatagctg agcaggagcc           50

<210> SEQ ID NO 4
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 4
cagacagagc ccacttagct tgtccacatg gatctcaatg ccaatcctcc           50

<210> SEQ ID NO 5
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 5
ctccgtacat gtgggtgtcg ccatgtgtgc cctgtcacta tctgtggctg           50

<210> SEQ ID NO 6
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 6
actgctgcgt cattacaggg cacaggccat ggatggaaaa cgctctctgc           50

<210> SEQ ID NO 7
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 7
gctttgggag tcttctgctt tgctggacat gagactggaa ggctgtctgg           50

<210> SEQ ID NO 8
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 8
acgggaggag accagtcccc cacccagccg taccagaaat aaaggcttct           50

<210> SEQ ID NO 9
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 9
ggttttctaa ccctgacacg gactgtgcat actttccctc atccatgctg           50

<210> SEQ ID NO 10
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 10
cgccgggtgc ccgctgcagt ttcttgggac ataggagcgc aaagaagcta           50

<210> SEQ ID NO 11
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 11
ctgcctccct catggtgtgc gtgtcgttct cttcctgacg catctgtgat           50

<210> SEQ ID NO 12
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 12
aagctcacag tgctggagga ggatgaaaag aagccggtgc cctgggagtc           50

<210> SEQ ID NO 13
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 13
gggccatcat cctcttcatc atcctcttca tcctgctgct gttcctggcc           50

<210> SEQ ID NO 14
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 14
gcagcctcca tgggtcagcg tgttccaaga ggaaaccgta accttgcact       50

<210> SEQ ID NO 15
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 15
gggctggctg tggtgacgct gctcaatttc ctggtgtgct tcggacctta       50

<210> SEQ ID NO 16
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 16
aggaaaagtc ttggctggac ccctttcctg ctgggtggat gcagtggtcc       50

<210> SEQ ID NO 17
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 17
cctaccctaa tgccagttcc agcttcatct acccttgagt catattgagg       50

<210> SEQ ID NO 18
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 18
gcatcaaccc tgtgctctat gcagccatga accgccaatt ccgccaagca       50

<210> SEQ ID NO 19
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 19
gctggcccaa gaccct taga accctgagtg ctggcaaatc tcactgctcc       50

<210> SEQ ID NO 20
<211> LENGTH: 50
<212> TYPE: DNA
<213> ORGANISM: Artificial Sequence
<220> FEATURE:
<223> OTHER INFORMATION: Synthetic probe sequence

```
<400> SEQUENCE: 20
gtgccacctc ctgtctactc attgttgcat gagccctgtc tgccagccca            50

<210> SEQ ID NO 21
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 21
ctgcagagcc tggttcaaaa tcagtcactc ccttcagaag cagacatggc            50

<210> SEQ ID NO 22
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 22
tcaccgctgt tgcctgccgc cttgcgcagt tgactcgtgt ctgaggaaac            50

<210> SEQ ID NO 23
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 23
ctcctggggc tctcagtgtg ccatagagga cagcaactgg tgattgtttc            50

<210> SEQ ID NO 24
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 24
ggcattatga aggcagcaca gtccccgaaa agaagacacc gaagagccct            50

<210> SEQ ID NO 25
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 25
gatcttccag gcctatggat agatcaggag gcatcactga ggccaggagc            50

<210> SEQ ID NO 26
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 26
gactgtgaaa ccgtcagttc ggaaggctgg ttagaacatg tgggagcaac            50

<210> SEQ ID NO 27
```

```
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 27
gggcattgtg ctggccccac tttcactggc cttcttggtt ttgggggaa              50

<210> SEQ ID NO 28
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 28
ggcacttgga gacttgtatg aaagatggct gtgcctctgc ctgtctcccc              50

<210> SEQ ID NO 29
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 29
ggtttccttc agacagattc caggcgatgt gcaagtgtat gcacgtgtgc              50

<210> SEQ ID NO 30
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 30
ccgccttcgt cgcagagacc tcttgctggg tttcaacaaa cgtgccattg              50

<210> SEQ ID NO 31
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 31
ccacatcgtc ttccctgtcc caatcgacca gtgtatcgac ggctgagtgc              50

<210> SEQ ID NO 32
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 32
gggctccaga gaaggcccgc gtctaaataa agcgccagcg caggatgaaa              50

<210> SEQ ID NO 33
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 33
```
ctctccgggt gcaaaagttc ctcgagtcag cctctccagg cccagctcct    50

<210> SEQ ID NO 34
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 34
gctgcctctc tccagaaatg aactgtgatg gtggacacag ctatgtgagg    50

<210> SEQ ID NO 35
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 35
ctcacccaac agatctttcc agaggtccat ggtggaagac gataaccctg    50

<210> SEQ ID NO 36
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 36
gcttctactg gcgcgtgagt tcccggagtg agttgaacca ggtggaccaa    50

<210> SEQ ID NO 37
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 37
cctgggttcc aatcctggct ctgtggcttg ctagctatgt gaccttgagc    50

<210> SEQ ID NO 38
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 38
acgtgggagg ccaagagcat ttcgctcact tgctgatcct cagggacacc    50

<210> SEQ ID NO 39
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 39
tgggtgagtt tcccccctcc ttattctgtc ctgagaccac gggcaaagct    50

<210> SEQ ID NO 40
<211> LENGTH: 50
<212> TYPE: DNA

<213> ORGANISM: Artificial Sequence
<220> FEATURE:
<223> OTHER INFORMATION: Synthetic probe sequence

<400> SEQUENCE: 40
gcgtacactc tctccaggca accagctcta ccacctcatc cagaattggc    50

<210> SEQ ID NO 41
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 41
ccttcgtgat ctggggatgt gccacccgcc ttttccctga cttcttcacg    50

<210> SEQ ID NO 42
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 42
tttgcaaagg gccaaatttc cccaaactga acgggctcag gaaatgttcc    50

<210> SEQ ID NO 43
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 43
tatttagggc aataagcagc attggcctgg agtgccagag cgtcacctcc    50

<210> SEQ ID NO 44
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 44
atcatttccc tctcctatgc accagtaagg cccgtccaga gccccagcag    50

<210> SEQ ID NO 45
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 45
cctcgttgca ctgctgagag caagatgggt caccagcagc tgtactggag    50

<210> SEQ ID NO 46
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 46
tccaaggcct ggatgctaat caagatgaac aggtcgactt tcaagaattc    50

```
<210> SEQ ID NO 47
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 47
ctttctggct cctcaaacag taggttggca gtaaggcagg gtcccatttc          50

<210> SEQ ID NO 48
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 48
gagtctcaag tccgtatgta aatcagatct cccctctcac ccctcccacc          50

<210> SEQ ID NO 49
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 49
ggcccccggc tcatcgtgta tgtcatgggc ggtgtggcca tgtcagagat          50

<210> SEQ ID NO 50
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 50
cgatgatgtc catggctttg tgggaagata ctgtggagat gagcttccag          50

<210> SEQ ID NO 51
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 51
agtaaaccca tatatccaga accctgaccc tgccgtgtac cagctgagag          50

<210> SEQ ID NO 52
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 52 aaaccgtca cccagatcgt cagcgccgag gcctggggta gagcaggtga           50
```